(12) United States Patent
Kinsho et al.

(10) Patent No.: US 7,531,289 B2
(45) Date of Patent: *May 12, 2009

(54) FLUORINATED MONOMER HAVING CYCLIC STRUCTURE, MANUFACTURING METHOD, POLYMER, PHOTORESIST COMPOSITION AND PATTERNING PROCESS

(75) Inventors: Takeshi Kinsho, Joetsu (JP); Takeru Watanabe, Joetsu (JP); Masaki Ohashi, Joetsu (JP); Koji Hasegawa, Joetsu (JP); Seiichiro Tachibana, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 379 days.

This patent is subject to a terminal disclaimer.

(21) Appl. No.: 11/258,894

(22) Filed: Oct. 27, 2005

(65) Prior Publication Data
US 2006/0093960 A1 May 4, 2006

(30) Foreign Application Priority Data
Oct. 28, 2004 (JP) .............................. 2004-313762

(51) Int. Cl.
G03F 7/039 (2006.01)
C08F 18/20 (2006.01)
C07D 315/00 (2006.01)

(52) U.S. Cl. ................... 430/270.1; 549/416; 549/417; 549/504; 526/246; 430/326

(58) Field of Classification Search ............... 430/270.1; 526/245, 247, 249, 250, 255, 260, 266, 270, 526/246; 549/416, 417, 423, 504, 429, 513
See application file for complete search history.

(56) References Cited

U.S. PATENT DOCUMENTS

| | | | | |
|---|---|---|---|---|
| 4,284,567 A * | 8/1981 | Prevedello et al. | .......... | 549/426 |
| 5,900,346 A * | 5/1999 | Sinta et al. | ............... | 430/270.1 |
| 6,602,646 B1 * | 8/2003 | Sato et al. | ................. | 430/270.1 |
| 6,784,312 B2 | 8/2004 | Miyazawa et al. | | |
| 6,800,414 B2 | 10/2004 | Nishimura et al. | | |
| 6,800,418 B2 | 10/2004 | Yoon et al. | | |
| 2003/0139613 A1 * | 7/2003 | Ishikawa et al. | ............. | 549/427 |
| 2003/0157430 A1 | 8/2003 | Yoon et al. | | |
| 2004/0175644 A1 * | 9/2004 | Abdourazak et al. | ..... | 430/270.1 |
| 2004/0236046 A1 | 11/2004 | Miyazawa et al. | | |
| 2004/0241580 A1 | 12/2004 | Nishimura et al. | | |
| 2005/0202351 A1 * | 9/2005 | Houlihan et al. | ........... | 430/322 |
| 2006/0094817 A1 * | 5/2006 | Harada et al. | ................ | 524/544 |
| 2008/0090173 A1 * | 4/2008 | Harada et al. | ............. | 430/270.1 |

FOREIGN PATENT DOCUMENTS

| | | |
|---|---|---|
| EP | 0 496415 A1 | 7/1992 |
| EP | 1 652 846 | 5/2006 |
| JP | 2002-72484 A | 3/2002 |
| JP | 2003-40840 A | 2/2003 |
| JP | 2003-192729 A | 7/2003 |

OTHER PUBLICATIONS

T. Nakai et al., Tetrahedron Letters, vol. 29, p. 4119, 1998.
T. Nakai et al., Organic Syntheses, vol. 76, p. 151, 1998.
T. Hiyama, Organofluorine Compounds Chemistry and Applications, pp. 25-29, 2000.
Jakubek V. et al: "Hexafluoroisopropyl and trifluoromethyl carbinols in an acrylate platform for 157 nm chemically amplified resists." Proceedings of the SPIE, SPIE, Bellingham, VA, US, vol. 5376, May 2004 pp. 554-564.

* cited by examiner

*Primary Examiner*—Cynthia H Kelly
*Assistant Examiner*—Anca Eoff
(74) *Attorney, Agent, or Firm*—Birch, Stewart, Kolasch & Birch, LLP

(57) ABSTRACT

Cyclic structure-bearing fluorinated monomers having formula (1) wherein Z is a divalent organic group containing a polymerizable unsaturated group are useful to produce polymers for the manufacture of radiation-sensitive resist compositions which are fully transparent to radiation having a wavelength of up to 300 nm and have improved development properties.

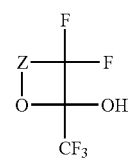

(1)

13 Claims, No Drawings

FLUORINATED MONOMER HAVING CYCLIC STRUCTURE, MANUFACTURING METHOD, POLYMER, PHOTORESIST COMPOSITION AND PATTERNING PROCESS

CROSS-REFERENCE TO RELATED APPLICATION

This non-provisional application claims priority under 35 U.S.C. §119(a) on Patent Application No. 2004-313762 filed in Japan on Oct. 28, 2004, the entire contents of which are hereby incorporated by reference.

TECHNICAL FIELD

This invention relates to novel fluorinated monomers (polymerizable compounds) having a cyclic structure. The fluorinated monomers having a cyclic structure are useful as raw materials for the synthesis of functional materials, pharmaceutical and agricultural chemicals, and most useful as monomers to produce polymers for the manufacture of radiation-sensitive resist compositions which are fully transparent to radiation having a wavelength of up to 500 nm, especially up to 300 nm, typically KrF, ArF and $F_2$ laser beams, and have improved development properties.

The invention also relates to a method for preparing the fluorinated monomers having a cyclic structure, polymers comprising recurring units derived from the fluorinated monomers having a cyclic structure, photoresist compositions comprising the polymers, and a patterning process using the photoresist compositions.

BACKGROUND ART

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF, ArF or $F_2$ laser as the light source is strongly desired to reach the practical level as the micropatterning technique capable of achieving a feature size of 0.3 µm or less. Various alkali-soluble resins are used as the base resin in such resists.

For KrF laser resists, a polyhydroxystyrene resin having phenolic hydroxyl groups as the alkali-soluble functional group is, in fact, a standard base resin. For ArF laser resists, poly(meth)acrylate resins using carboxyl groups as the alkali-soluble group and resins comprising polymerized units of cycloaliphatic olefin such as norbornene are under investigation. Of these, the poly(meth)acrylate resins are regarded, due to ease of polymerization, as a promising candidate that will find practical use. For these resist resins using as the alkali-soluble functional group carboxyl groups having a higher acidity than phenolic hydroxyl groups, however, an outstanding issue is difficulty of dissolution control, often leading to pattern collapse caused by swelling or the like.

Functional groups having an acidity comparable to phenolic hydroxyl groups are desired. It was proposed to use an alcohol having a plurality of fluorine atoms substituted at α- and α'-positions (e.g., having a partial structure: —$C(CF_3)_2$OH) as the alkali-soluble functional group, as described in G. Wallraff et al., Active Fluororesists for 157 nm lithography in 2nd International Symposium on 157 nm Lithography. Styrene and norbornene derivatives having fluoroalcohol —$C(CF_3)_2$OH incorporated therein are proposed as monomers used in the manufacture of base resins. Similar examples of fluoroalcohol-substituted norbornene are found in JP-A 2003-192729 and JP-A 2002-72484. For the polymerization of norbornene monomers, however, radical polymerization between monomers of the same type is difficult, and instead, special polymerization technique such as coordinate polymerization or ring-opening metathesis polymerization using unique transition metal catalysts is necessary. Although alternating copolymerization between a norbornene monomer and a comonomer such as maleic anhydride or maleimide can be implemented by radical polymerization, the presence of comonomer imposes a substantial limit on the freedom of resin design.

JP-A 2003-040840 describes fluoroalcohol-substituted acrylate monomers. Although the method of preparing these monomers is not definite, the starting reactant used is hexafluoroacetone (boiling point −27° C.) which is awkward to handle because it is gaseous at room temperature. The synthesis of polymerizable compound must follow long steps, leaving the problem that commercial preparation is difficult.

There is a strong demand to develop a polymerizable compound or monomer which is industrially amenable and which has both a polymerizable unsaturated group such as a (meth) acrylate structure that facilitates the preparation or polymerization of a resist resin and a functional group that has an acidity comparable to phenolic hydroxyl.

DISCLOSURE OF THE INVENTION

An object of the present invention is to provide novel fluorinated monomers having a cyclic structure which are useful for the preparation of polymers to be formulated in resist compositions having high transparency to laser radiation with a wavelength of up to 500 nm, especially up to 300 nm, and an excellent development behavior, and which monomers can be prepared from reactants that are readily available and easily manageable.

Other objects are to provide a method for preparing the fluorinated monomers having a cyclic structure, polymers comprising recurring units derived from the fluorinated monomers having a cyclic structure, photoresist compositions comprising the polymers, and a patterning process using the photoresist compositions.

The inventor has found that fluorinated monomers with a cyclic structure having the general formulae (1), (2), (3) and (4), shown below, can be prepared from readily available reactants by the method, described later, in high yields and in a simple manner; that these monomers are polymerizable by industrially easily implementable polymerization techniques such as radical polymerization; and that using a polymer resulting from the polymerization as a base resin, a radiation-sensitive resist composition having high transparency to radiation with a wavelength of up to 300 nm and excellent development behavior is obtainable.

Thus the present invention provides fluorinated monomers having a cyclic structure, manufacturing methods, polymers, photoresist compositions, and a patterning process, as defined below.

In a first aspect, the present invention provides a fluorinated monomer having a cyclic structure represented by the general formula (1):

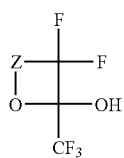

wherein Z is a divalent organic group containing a polymerizable unsaturated group.

Typically, the ring represented by

is a 5 or 6-membered ring.

Other embodiments are fluorinated monomers having a cyclic structure represented by the general formulae (2), (3) and (4).

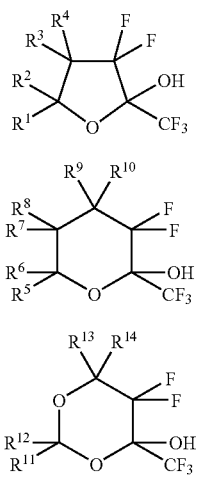

Herein $R^1$, $R^2$, $R^3$, and $R^4$ are each independently selected from among hydrogen, hydroxyl, halogen, and straight, branched or cyclic monovalent organic groups of 1 to 15 carbon atoms, at least one of $R^1$, $R^2$, $R^3$ and $R^4$ is a monovalent organic group containing a polymerizable unsaturated group, a combination of any, at least two of $R^1$, $R^2$, $R^3$ and $R^4$ may bond together to form a ring with the carbon atom or atoms to which they are attached, the ring contains a polymerizable unsaturated group unless the remaining group or groups which do not relate to the ring formation contain a polymerizable unsaturated group; $R^5$, $R^6$, $R^7$, $R^8$, $R^9$, and $R^{10}$ are each independently selected from among hydrogen, hydroxyl, halogen, and straight, branched or cyclic monovalent organic group of 1 to 15 carbon atoms, at least one of $R^5$, $R^6$, $R^7$, $R^8$, $R^9$, and $R^{10}$ is a monovalent organic group containing a polymerizable unsaturated group, a combination of any, at least two of $R^5$, $R^6$, $R^7$, $R^8$, $R^9$, and $R^{10}$ may bond together to form a ring with the carbon atom or atoms to which they are attached, the ring contains a polymerizable unsaturated group unless the remaining group or groups which do not relate to the ring formation contain a polymerizable unsaturated group; $R^{11}$, $R^{12}$, $R^{13}$, and $R^{14}$ are each independently selected from among hydrogen, hydroxyl, halogen, and straight, branched or cyclic monovalent organic groups of 1 to 15 carbon atoms, at least one of $R^{11}$, $R^{12}$, $R^{13}$ and $R^{14}$ is a monovalent organic group containing a polymerizable unsaturated group, a combination of any, at least two of $R^{11}$, $R^{12}$, $R^{13}$ and $R^{14}$ may bond together to form a ring with the carbon atom or atoms to which they are attached, the ring contains a polymerizable unsaturated group unless the remaining group or groups which do not relate to the ring formation contain a polymerizable unsaturated group.

In a preferred embodiment, the polymerizable unsaturated group is a group of acrylate, methacrylate or a-trifluoromethylacrylate structure having the general formula (5):

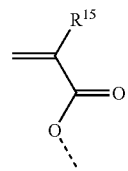

wherein $R^{15}$ is hydrogen, methyl or trifluoromethyl, and the broken line denotes a valence bond.

In another preferred embodiment, the polymerizable unsaturated group is a group of unsaturated hydrocarbon structure having the general formula (6) or (7):

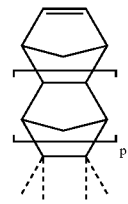

wherein p and q are each independently 1 or 0, and the broken line denotes a valence bond.

In a second aspect, the present invention provides a polymer comprising recurring units having the general formula (1a), (2a), (3a) or (4a).

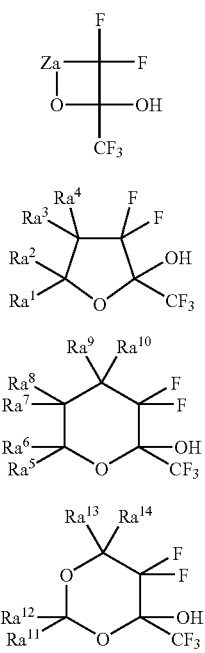

(1a)

(2a)

(3a)

(4a)

Herein Za is an organic group which is derived from a divalent organic group containing a polymerizable unsaturated group, represented by Z in formula (1) in claim 1, and which contains a polymeric main chain of recurring units in a polymer obtained through polymerization of said polymerizable unsaturated group; $Ra^1$, $Ra^2$, $Ra^3$, and $Ra^4$ are each independently selected from among hydrogen, hydroxyl, halogen, and straight, branched or cyclic monovalent organic groups of 1 to 15 carbon atoms, at least one of $Ra^1$, $Ra^2$, $Ra^3$, and $Ra^4$ is an organic group which is derived from a monovalent organic group containing a polymerizable unsaturated group, represented by at least one of $R^1$ to $R^4$ in formula (2) in claim 3, and which contains a polymeric main chain of recurring units in a polymer obtained through polymerization of said polymerizable unsaturated group, a combination of any, at least two of $Ra^1$ to $Ra^4$ may bond together to form a ring with the carbon atom or atoms to which they are attached, the ring may contain a polymeric main chain of recurring units in a polymer derived from a polymerizable unsaturated group and obtained through polymerization of said polymerizable unsaturated group; $Ra^5$, $Ra^6$, $Ra^7$, $Ra^8$, $Ra^9$ and $Ra^{10}$ are each independently selected from among hydrogen, hydroxyl, halogen, and straight, branched or cyclic monovalent organic groups of 1 to 15 carbon atoms, at least one of $Ra^5$ to $Ra^{10}$ is an organic group which is derived from a monovalent organic group containing a polymerizable unsaturated group, represented by at least one of $R^5$ to $R^{10}$ in formula (3) in claim 3, and which contains a polymeric main chain of recurring units in a polymer obtained through polymerization of said polymerizable unsaturated group, a combination of any, at least two of $Ra^5$ to $Ra^{10}$ may bond together to form a ring with the carbon atom or atoms to which they are attached, the ring may contain a polymeric main chain of recurring units in a polymer derived from a polymerizable unsaturated group and obtained through polymerization of said polymerizable unsaturated group; $Ra^{11}$, $Ra^{12}$, $Ra^{13}$, and $Ra^{14}$ are each independently selected from among hydrogen, hydroxyl, halogen, and straight, branched or cyclic monovalent organic groups of 1 to 15 carbon atoms, at least one of $Ra^{11}$, $Ra^{12}$, $Ra^3$, and $Ra^{14}$ is an organic group which is derived from a monovalent organic group containing a polymerizable unsaturated group, represented by at least one of $R^{11}$ to $R^{14}$ in formula (4) in claim 3, and which contains a polymeric main chain of recurring units in a polymer obtained through polymerization of said polymerizable unsaturated group, a combination of any, at least two of $Ra^{11}$ to $Ra^{14}$ may bond together to form a ring with the carbon atom or atoms to which they are attached, the ring may contain a polymeric main chain of recurring units in a polymer derived from a polymerizable unsaturated group and obtained through polymerization of said polymerizable unsaturated group.

In a preferred embodiment, the polymeric main chain of recurring units in a polymer obtained through polymerization of the polymerizable unsaturated group has an acrylate, methacrylate or α-trifluoromethylacrylate structure having the general formula (5a):

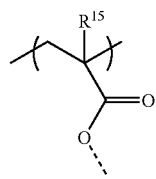

(5a)

wherein $R^{15}$ is hydrogen, methyl or trifluoromethyl, and the broken line denotes a valence bond.

In a preferred embodiment, the polymer may further comprise recurring units having the general formula (8a):

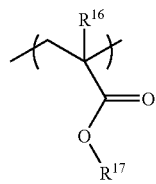

(8a)

wherein $R^{16}$ is hydrogen, methyl or trifluoromethyl, and $R^{17}$ is an acid labile group. The polymer should preferably have a weight average molecular weight in the range of 2,000 to 100,000.

In a third aspect, the present invention provides a photoresist composition comprising (A) the polymer defined above, (B) a photoacid generator, and (C) an organic solvent.

In a fourth aspect, the present invention provides a process for forming a pattern, comprising the steps of (1) applying the resist composition onto a substrate to form a coating, (2) heat treating the coating and exposing it to high-energy radiation with a wavelength of up to 300 nm or electron beam through a photomask, and (3) optionally heat treating the coating and developing it with a developer; or a process for forming a pattern, comprising the steps of (1) applying the resist composition onto a substrate to form a coating, (2) heat treating the coated substrate, introducing a liquid between the coated substrate and a projection lens, and exposing the coating to high-energy radiation with a wavelength of up to 300 nm through a photomask, and (3) optionally heat treating the coating and developing it with a developer.

In a fifth aspect, the present invention provides a method for preparing a fluorinated monomer, comprising cyclizing a keto-alcohol compound having the general formula (9), (10), (11) or (12) to form a hemiacetal compound having the general formula (13), (14), (15) or (16).

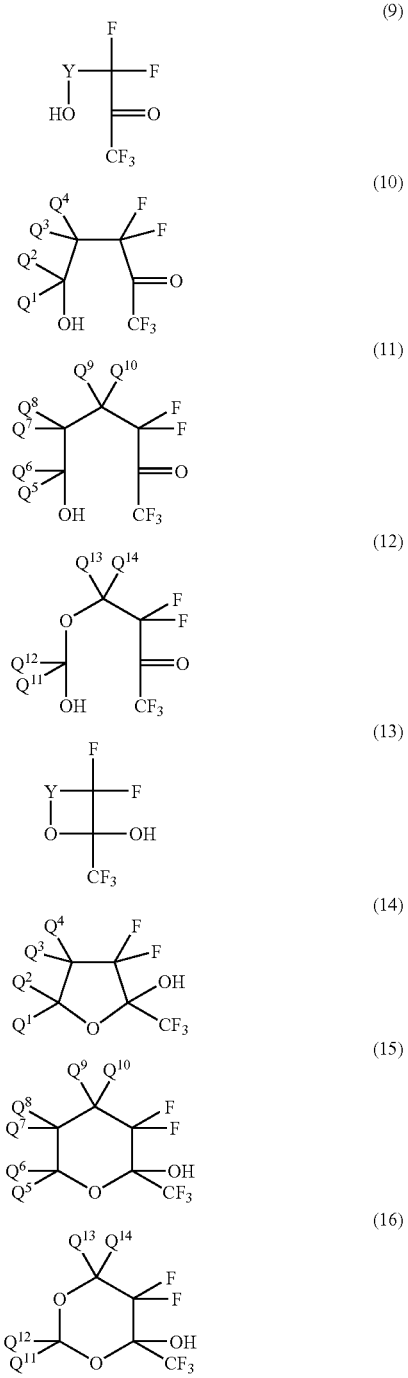

Herein Y is a divalent organic group containing a polymerizable unsaturated group or a divalent organic group having a functional group which can be converted to a polymerizable unsaturated group; $Q^1$, $Q^2$, $Q^3$, and $Q^4$ are each independently selected from among hydrogen, hydroxyl, halogen, and straight, branched or cyclic monovalent organic groups of 1 to 15 carbon atoms, at least one of $Q^1$, $Q^2$, $Q^3$, and $Q^4$ is a monovalent organic group containing a polymerizable unsaturated group or a monovalent organic group having a functional group which can be converted to a polymerizable unsaturated group, a combination of any, at least two of $Q^1$ to $Q^4$ may bond together to form a ring with the carbon atom or atoms to which they are attached, the ring contains a polymerizable unsaturated group or a functional group which can be converted to a polymerizable unsaturated group unless the remaining group or groups which do not relate to the ring formation contain a polymerizable unsaturated group or a functional group which can be converted to a polymerizable unsaturated group; $Q^5$, $Q^6$, $Q^7$, $Q^8$, $Q^9$ and $Q^{10}$ are each independently selected from among hydrogen, hydroxyl, halogen, and straight, branched or cyclic monovalent organic groups of 1 to 15 carbon atoms, at least one of $Q^5$, $Q^6$, $Q^7$, $Q^8$, $Q^9$ and $Q^{10}$ is a monovalent organic group containing a polymerizable unsaturated group or a monovalent organic group having a functional group which can be converted to a polymerizable unsaturated group, a combination of any, at least two of $Q^5$ to $Q^{10}$ may bond together to form a ring with the carbon atom or atoms to which they are attached, the ring contains a polymerizable unsaturated group or a functional group which can be converted to a polymerizable unsaturated group unless the remaining group or groups which do not relate to the ring formation contain a polymerizable unsaturated group or a functional group which can be converted to a polymerizable unsaturated group; $Q^{11}$, $Q^{12}$, $Q^{13}$, and $Q^{14}$ are each independently selected from among hydrogen, hydroxyl, halogen, and straight, branched or cyclic monovalent organic groups of 1 to 15 carbon atoms, at least one of $Q^{11}$, $Q^{12}$, $Q^{13}$, and $Q^{14}$ is a monovalent organic group containing a polymerizable unsaturated group or a monovalent organic group having a functional group which can be converted to a polymerizable unsaturated group, a combination of any, at least two of $Q^{11}$ to $Q^{14}$ may bond together to form a ring with the carbon atom or atoms to which they are attached, the ring contains a polymerizable unsaturated group or a functional group which can be converted to a polymerizable unsaturated group unless the remaining group or groups which do not relate to the ring formation contain a polymerizable unsaturated group or a functional group which can be converted to a polymerizable unsaturated group.

The present invention offers fluorinated monomers having a cyclic structure which are novel. These fluorinated monomers having a cyclic structure are useful reactants for functional materials, pharmaceutical and agricultural chemicals. In particular, they are very useful in forming polymers which are formulated in radiation-sensitive resist compositions having high transparency to radiation with a wavelength of up to 500 nm, especially up to 300 nm, and an excellent development behavior owing to the inclusion of phenol-like acidic hydroxyl groups. When these polymers are used in radiation-sensitive resist compositions as a base resin, the effective utilization of hydroxyl groups having an appropriate acidity helps minimize the swelling of resist film for preventing pattern collapse and restrain the appearance of a T-top profile for improving dimensional uniformity.

DESCRIPTION OF THE PREFERRED EMBODIMENTS

Monomer

The fluorinated monomers having a cyclic structure of the invention have a fluorinated hemiacetal structure of the general formula (1).

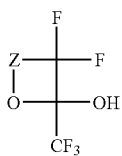

(1)

Herein Z is a divalent organic group containing a polymerizable unsaturated group.

For stability and ease of preparation, the hemiacetal structure is preferably a 5-membered or 6-membered hemiacetal structure in which the ring represented by

is 5-membered or 6-membered ring. More preferred are monomers of oxolane, oxane and dioxane hemiacetal structures having the general formulae (2), (3) and (4), respectively.

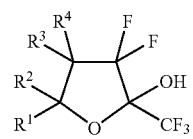

(2)

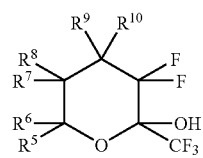

(3)

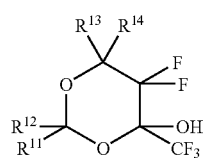

(4)

Herein $R^1$, $R^2$, $R^3$, and $R^4$ are each independently selected from among hydrogen, hydroxyl, halogen, and straight, branched or cyclic monovalent organic groups of 1 to 15 carbon atoms, at least one of $R^1$, $R^2$, $R^3$ and $R^4$ is a monovalent organic group containing a polymerizable unsaturated group. A combination of any, at least two of $R^1$, $R^2$, $R^3$ and $R^4$ may bond together to form a ring with the carbon atom or atoms to which they are attached, the ring contains a polymerizable unsaturated group unless the remaining group or groups which do not relate to the ring formation contain a polymerizable unsaturated group. $R^5$, $R^6$, $R^7$, $R^8$, $R^9$, and $R^{10}$ are each independently selected from among hydrogen, hydroxyl, halogen, and straight, branched or cyclic monovalent organic group of 1 to 15 carbon atoms, at least one of $R^5$, $R^6$, $R^7$, $R^8$, $R^9$, and $R^{10}$ is a monovalent organic group containing a polymerizable unsaturated group. A combination of any, at least two of $R^5$, $R^6$, $R^7$, $R^8$, $R^9$, and $R^{10}$ may bond together to form a ring with the carbon atom or atoms to which they are attached, the ring contains a polymerizable unsaturated group unless the remaining group or groups which do not relate to the ring formation contain a polymerizable unsaturated group. $R^{11}$, $R^{12}$, $R^{13}$, and $R^{14}$ are each independently selected from among hydrogen, hydroxyl, halogen, and straight, branched or cyclic monovalent organic groups of 1 to 15 carbon atoms, at least one of $R^{11}$, $R^{12}$, $R^{13}$ and $R^{14}$ is a monovalent organic group containing a polymerizable unsaturated group. A combination of any, at least two of $R^{11}$, $R^{12}$, $R^{13}$ and $R^{14}$ may bond together to form a ring with the carbon atom or atoms to which they are attached, the ring contains a polymerizable unsaturated group unless the remaining group or groups which do not relate to the ring formation contain a polymerizable unsaturated group.

It is generally believed that a hemiacetal structure (HA) is in-equilibrium with a open-chain keto-alcohol compound (KA). It is said that in the case of a 5- or 6-membered ring, the equilibrium is biased toward the hemiacetal side, which has higher stability. The compound of hemiacetal structure (HA) having the general formula (2), (3) or (4) becomes predominant for the following reason. A corresponding open-chain keto-alcohol structure (KA) of the general formula (2'), (3') or (4'), shown below, have five fluorine atoms substituted on carbon atoms (α-carbon and α'-carbon) adjoining the carbonyl group. Due to the strong electron-withdrawing effect of these fluorine atoms, the carbon of the carbonyl group is more susceptible to attack by a nucleophilic agent than ordinary carbonyl groups. This allows for an intramolecular nucleophilic attack by the hydroxyl group of the open-chain keto-alcohol compound (KA). Thus the compound is more likely to take a stable hemiacetal structure (HA). Particularly in the case of dioxane hemiacetal structure of formula (4), the open-chain keto-alcohol compound (4') assumes an unstable open-chain hemiacetal structure, which structure is considered not to exist stably. Inversely stated, by taking a cyclic hemiacetal structure through cyclization, the compound (4) in which an acetal structure and a hemiacetal structure are co-resent within the molecule exists stably.

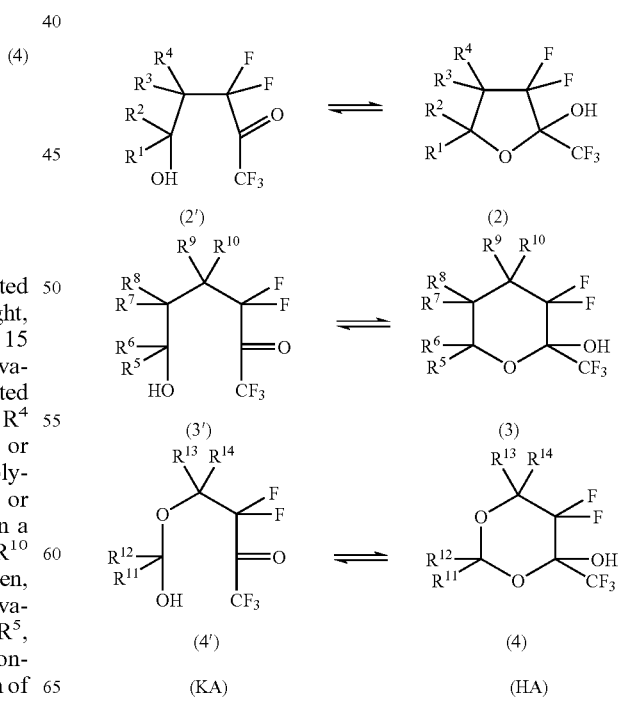

The structure of the groups represented by Z, $R^1$, $R^2$, $R^3$, and $R^4$ or $R^5$, $R^6$, $R^7$, $R^8$, $R^9$, and $R^{10}$ or $R^{11}$, $R^{12}$, $R^{13}$ and $R^{14}$ and the position of substitution of polymerizable unsaturated group are determined arbitrary, depending on many conditions including ease of preparation, the polymerizability of the target monomer, the acidity of fluoroalcohol, and physical properties of a polymer to be synthesized from the monomer.

Z is a divalent organic group containing a polymerizable unsaturated group. Specifically, Z is a straight, branched or cyclic, divalent organic group of 1 to 15 carbon atoms containing a polymerizable unsaturated group. Suitable divalent hydrocarbon groups are obtained from monovalent hydrocarbon groups by substituting a single bond for one hydrogen atom and further substituting a polymerizable unsaturated group for another hydrogen atom. Examples of the suitable monovalent hydrocarbon groups include straight, branched or cyclic alkyl groups such as methyl, ethyl, propyl, isopropyl, n-butyl, sec-butyl, tert-butyl, tert-amyl, n-pentyl, n-hexyl, n-heptyl, n-octyl, n-nonyl, n-decyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, methylcyclohexylmethyl, ethylcyclohexylmethyl, ethylcyclohexylethyl, bicyclo[2.2.1]heptyl, bicyclo[2.2.1]heptylmethyl, bicyclo[2.2.1]heptylethyl, bicyclo[2.2.1]heptylbutyl, methylbicyclo[2.2.1]heptylmethyl, ethylbicyclo[2.2.1]heptylmethyl, ethylbicyclo[2.2.1]heptylethyl, bicyclo[2.2.2]octyl, bicyclo[2.2.2]octylmethyl, bicyclo[2.2.2]octylethyl, bicyclo[2.2.2]octylbutyl, methylbicyclo[2.2.2]octylmethyl, ethylbicyclo[2.2.2]octylmethyl, ethylbicyclo[2.2.2]octylethyl, tricyclo[5.2.1.0$^{2,6}$]decyl, tricyclo[5.2.1.0$^{2,6}$]decylmethyl, tricyclo[5.2.1.0$^{2,6}$]decylethyl, tricyclo[5.2.1.0$^{2,6}$]decylbutyl, methyltricyclo[5.2.1.0$^{2,6}$]decylmethyl, ethyltricyclo[5.2.1.0$^{2,6}$]decylmethyl, ethyltricyclo[5.2.1.0$^{2,6}$]decylethyl, adamantyl, adamantylmethyl, adamantylethyl, adamantylbutyl, methyladamantylmethyl, ethyladamantylmethyl, ethyladamantylethyl, tetracyclo[4.4.0.1$^{2,5}$.1$^{7,10}$]dodecyl, tetracyclo[4.4.0.1$^{2,5}$.1$^{7,10}$]dodecylmethyl, tetracyclo[4.4.0.1$^{2,5}$.1$^{7,10}$]dodecylethyl, tetracyclo[4.4.0.1$^{2,5}$.1$^{7,10}$]dodecylbutyl, tetracyclo[4.4.0.1$^{2,5}$.1$^{7,10}$]dodecylmethyl, ethyltetracyclo[4.4.0.1$^{2,5}$.1$^{7,10}$]dodecylmethyl, and ethyltetracyclo[4.4.0.1$^{2,5}$.1$^{7,10}$]dodecylethyl; aryl groups such as phenyl, tolyl, naphthyl, anthryl, and phenanthryl; and aralkyl groups such as benzyl, diphenylmethyl and phenethyl. Some of the hydrogen atoms on the foregoing groups may be replaced by halogen atoms, alkyl, aryl, alkoxy, alkoxycarbonyl, oxo, alkoxyalkyl, acyloxy, acyloxyalkyl or alkoxyalkoxy groups.

$R^1$, $R^2$, $R^3$, and $R^4$ are each independently selected from among hydrogen, hydroxyl, halogen atoms, and straight, branched or cyclic monovalent organic groups of 1 to 15 carbon atoms, at least one of $R^1$, $R^2$, $R^3$ and $R^4$ is a monovalent organic group containing a polymerizable unsaturated group. Examples of the straight, branched or cyclic, monovalent $C_1$-$C_{15}$ organic group include monovalent hydrocarbon groups including straight, branched or cyclic alkyl groups such as methyl, ethyl, propyl, isopropyl, n-butyl, sec-butyl, tert-butyl, tert-amyl, n-pentyl, n-hexyl, n-heptyl, n-octyl, n-nonyl, n-decyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, methylcyclohexylmethyl, ethylcyclohexylmethyl, ethylcyclohexylethyl, bicyclo[2.2.1]heptyl, bicyclo[2.2.1]heptylmethyl, bicyclo[2.2.1]heptylethyl, bicyclo[2.2.1]heptylbutyl, methylbicyclo[2.2.1]heptylmethyl, ethylbicyclo[2.2.1]heptylmethyl, ethylbicyclo[2.2.1]heptylethyl, bicyclo[2.2.2]octyl, bicyclo[2.2.2]octylmethyl, bicyclo[2.2.2]octylethyl, bicyclo[2.2.2]octylbutyl, methylbicyclo[2.2.2]octylmethyl, ethylbicyclo[2.2.2]octylmethyl, ethylbicyclo[2.2.2]octylethyl, tricyclo[5.2.1.0$^{2,6}$]decyl, tricyclo[5.2.1.0$^{2,6}$]decylmethyl, tricyclo[5.2.1.0$^{2,6}$]decylethyl, tricyclo[5.2.1.0$^{2,6}$]decylbutyl, methyltricyclo[5.2.1.0$^{2,6}$]decylmethyl, ethyltricyclo[5.2.1.0$^{2,6}$]decylmethyl, ethyltricyclo[5.2.1.0$^{2,6}$]decylethyl, adamantyl, adamantylmethyl, adamantylethyl, adamantylbutyl, methyladamantylmethyl, ethyladamantylmethyl, ethyladamantylethyl, tetracyclo[4.4.0.1$^{2,5}$.1$^{7,10}$]dodecyl, tetracyclo[4.4.0.1$^{2,5}$.1$^{7,10}$]dodecylmethyl, tetracyclo[4.4.0.1$^{2,5}$.1$^{7,10}$]dodecylethyl, tetracyclo[4.4.0.1$^{2,5}$.1$^{7,10}$]dodecylbutyl, tetracyclo[4.4.0.1$^{2,5}$.1$^{7,10}$]dodecylmethyl, ethyltetracyclo[4.4.0.1$^{2,5}$.1$^{7,10}$]dodecylmethyl, and ethyltetracyclo[4.4.0.1$^{2,5}$.1$^{7,10}$]dodecylethyl; aryl groups such as phenyl, tolyl, naphthyl, anthryl, and phenanthryl; and aralkyl groups such as benzyl, diphenylmethyl and phenethyl; as well as alkoxy groups such as methoxy, ethoxy and propoxy, and acyloxy groups such as formyloxy and acetoxy. Some of the hydrogen atoms on the foregoing groups may be replaced by halogen atoms, alkyl, aryl, alkoxy, alkoxycarbonyl, oxo, alkoxyalkyl, acyloxy, acyloxyalkyl or alkoxyalkoxy groups. Of these groups, hydrogen, hydroxyl, halogen, methyl, ethyl, propyl, tert-butyl and perfluoroalkyl are preferred. The monovalent organic group containing a polymerizable unsaturated group may be a polymerizable unsaturated group as such or any of the foregoing monovalent organic groups in which one hydrogen atom is replaced by a polymerizable unsaturated group.

At least any two of $R^1$, $R^2$, $R^3$ and $R^4$ taken together may form a ring with the carbon atom or atoms to which they are attached. Exemplary combinations for the ring formation may typically include pairs of $R^1$ and $R^2$, $R^1$ and $R^3$, $R^1$ and $R^4$, $R^2$ and $R^3$, $R^2$ and $R^4$, and $R^3$ and $R^4$. Examples of the ring include alicyclic-cycloaliphatic hydrocarbon groups of 3 to 12 carbon atoms, such as cyclopropane, cyclobutane, cyclopentane, cyclohexane, bicyclo[2.2.1]heptane, bicyclo[2.2.2]octane, tricyclo[5.2.1.0$^{2,6}$]decane, adamantane, and tetracyclo[4.4.0.1$^{2,5}$.1$^{7,10}$]dodecane as well as fused rings containing any. Some hydrogen atoms on the foregoing alicyclic-cycloaliphatic hydrocarbon groups may be replaced by halogen atoms, alkyl, aryl, alkoxy, alkoxycarbonyl, oxo, alkoxyalkyl, acyloxy, acyloxyalkyl or alkoxyalkoxy groups.

The ring contains a polymerizable unsaturated group unless the remaining group or groups which do not relate to the ring formation contain a polymerizable unsaturated group. For example, when $R^1$ and $R^2$ (or $R^1$ and $R^3$) relate to a ring formation and $R^3$ and $R^4$ (or $R^2$ and $R^4$) do not relate to such a ring formation, the ring should contain a polymerizable unsaturated group if $R^3$ and $R^4$ (or $R^2$ and $R^4$) do not contain any polymerizable unsaturated groups.

For $R^5$, $R^6$, $R^7$, $R^8$, $R^9$, and $R^{10}$ and $R^{11}$, $R^{12}$, $R^{13}$ and $R^{14}$, those groups exemplified for $R^1$, $R^2$, $R^3$ and $R^4$ are similarly appropriate. Exemplary combinations for the ring formation may typically include $R^5$ and $R^6$, $R^5$ and $R^7$, $R^5$ and $R^8$, $R^6$ and $R^7$, $R^6$ and $R^8$, $R^7$ and $R^8$, $R^7$ and $R^9$, $R^7$ and $R^{10}$, $R^8$ and $R^9$, $R^8$ and $R^{10}$, $R^9$ and $R^{10}$, $R^{11}$ and $R^{12}$, and $R^{13}$ and $R^{14}$.

The polymerizable unsaturated group in formulae (1), (2), (3) and (4) may be any group having a double bond which is polymerizable by polymerization means such as radical polymerization, anionic polymerization and cationic polymerization. Suitable structures having a polymerizable unsaturated group include unsaturated hydrocarbon structures such as bicyclo[2.2.1]hept-2-ene, tricyclo[5.2.1.0$^{2,6}$]dec-8-ene, and tetracyclo[4.4.0.1$^{2,5}$.1$^{7,10}$]dodec-3-ene; unsaturated ether structures such as vinyloxy and allyloxy; α,β-unsaturated ketone structures such as vinyl ketone and isopropenyl ketone; α,β-unsaturated ester structures such as acrylates, methacrylates, and α-trifluoromethylacrylates; and unsaturated hydrocarbon ester structures such as bicyclo[2.2.1]hept-5-ene-2-carboxylic acid ester and tetracyclo[4.4.0.1$^{2,5}$.1$^{7,10}$]dodec-8-ene-3-carboxylic acid ester. Of these, those groups containing an α,β-unsaturated ester structure having the general formula (5), shown below, are more preferred. Specifically, acrylate, methacrylate and α-trifluoromethylacrylate structures are more preferred.

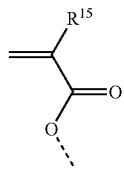
(5)

Herein $R^{15}$ is hydrogen, methyl or trifluoromethyl, and the broken line denotes a valence bond.

In another preferred embodiment, the polymerizable unsaturated group is a group of unsaturated hydrocarbon structure having the general formula (6) or (7).

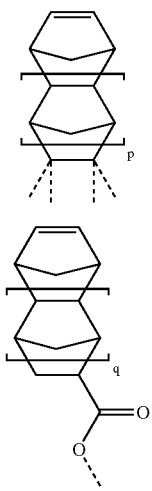
(6)

(7)

Herein p and q are each independently 1 or 0, and the broken line denotes a valence bond.

The divalent organic group Z, and the monovalent organic group containing a polymerizable unsaturated group or the ring containing a polymerizable unsaturated group among $R^1$ to $R^{14}$ preferably contain the group of formula (5), (6) or (7). In this case, the polymerizable unsaturated group of formula (5) or (7) is included in Z or the ring containing a polymerizable unsaturated group as the polymerizable unsaturated group by combining the valence bond of formula (5) or (7) with any one valence bond of a trivalent connecting group. Examples of the trivalent connecting group preferably include ones obtained from unsubstituted or hydroxy, halogen, alkoxy, alkoxyalkyl, alkoxyalkoxy, acyloxy or acyloxyalkyl group-substituted linear, branched or cyclic alkylene group having 1 to 10 carbon atoms by substituting a single bond (a valence bond) for one hydrogen atom bonded to a carbon atom of the alkylene group.

Alternatively, when the polymerizable unsaturated group of formula (5) or (7) is included in the monovalent organic group containing a polymerizable unsaturated group as the polymerizable unsaturated group, the group of formula (5) or (7) per se may be constituted as the monovalent organic group containing a polymerizable unsaturated group and directly bonded to the carbon atom or atoms (referred to carbon atom "C" hereinbelow) to which the monovalent organic group containing a polymerizable unsaturated group is to be bonded. That is, the valence bond of formula (5) or (7) is directly bonded to the carbon atom "C". The group of formula (5) or (7) may also be bonded via a divalent connecting group (preferably a linear, branched or cyclic alkylene group having 1 to 10 carbon atoms) to the above-described carbon atom "C". That is, the valence bond of formula (5) or (7) is bonded to the carbon atom "C" via the above divalent connecting group.

In formula (6), one or two valence bonds thereof may preferably act as the valence bond(s) for inclusion in Z or the monovalent organic group containing a polymerizable unsaturated group or the ring containing a polymerizable unsaturated group among $R^1$ to $R^{14}$ as the polymerizable unsaturated group. Each of the remaining valence bonds is preferably bonded to hydrogen atom, hydroxy group, halogen atom, or a linear, branched or cyclic monovalent organic group having 1 to 15 carbon atoms as exemplified above.

The way in which one of the valence bonds of formula (6) is included in Z or the monovalent organic group containing a polymerizable unsaturated group or the ring containing a polymerizable unsaturated group among $R^1$ to $R^4$ is the same as the way in which the valence bond of formula (5) or (7) is bonded.

The way in which two valence bonds among the valence bonds of formula (6) is included in Z or the ring containing a polymerizable unsaturated group is the way in which the group of formula (6) per se is constituted as R or the ring containing a polymerizable unsaturated group, or the way in which a divalent group formed by bonding one or both valence bonds of the two valence bonds with the above-described divalent connecting group is constituted as R or the ring containing a polymerizable unsaturated group. The way in which the two valence bonds among the valence bonds of formula (6) can be included in the monovalent organic group containing a polymerizable unsaturated group is the way in which a monovalent group formed by bonding each of the two valence bonds with the above-described divalent group and attaching the connecting groups to carbon atom(s) present at adequate position(s) to form a ring is constituted as the monovalent organic group containing a polymerizable unsaturated group.

For example, the two valence bonds may be bonded to formula (2) as a spiro ring shown by the following formula:

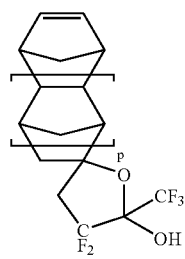

or as a condensed ring shown by the following formula:

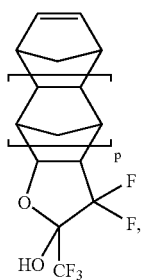

although not limited to the above way.

Examples of the connecting groups include:

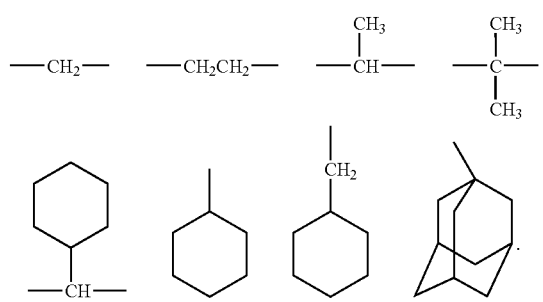

In the cyclic structure-bearing fluorinated monomers of formulae (1), (2), (3) and (4) according to the invention, depending on the type and combination of the groups represented by Z, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$, carbon atoms constituting the molecule can be asymmetric, and there can exist enantiomers and diastereomers. Each of formulae (1) to (4) collectively represents all such stereoisomers. Such stereoisomers may be used alone or in admixture.

Illustrative examples of the cyclic structure-bearing fluorinated monomers having formulae (1), (2), (3) and (4) are given below, but are not limited thereto. Note that Ac stands for acetyl.

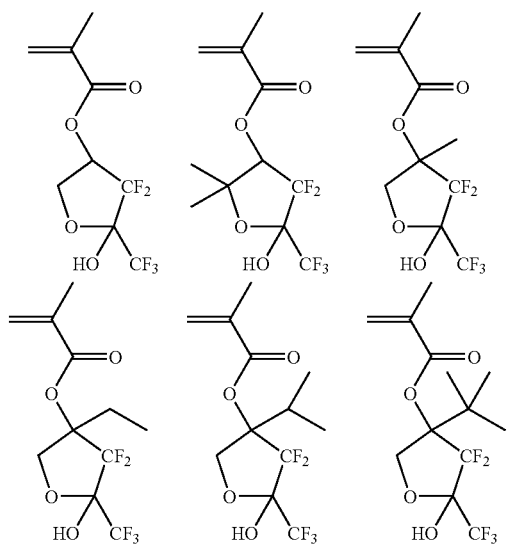

-continued

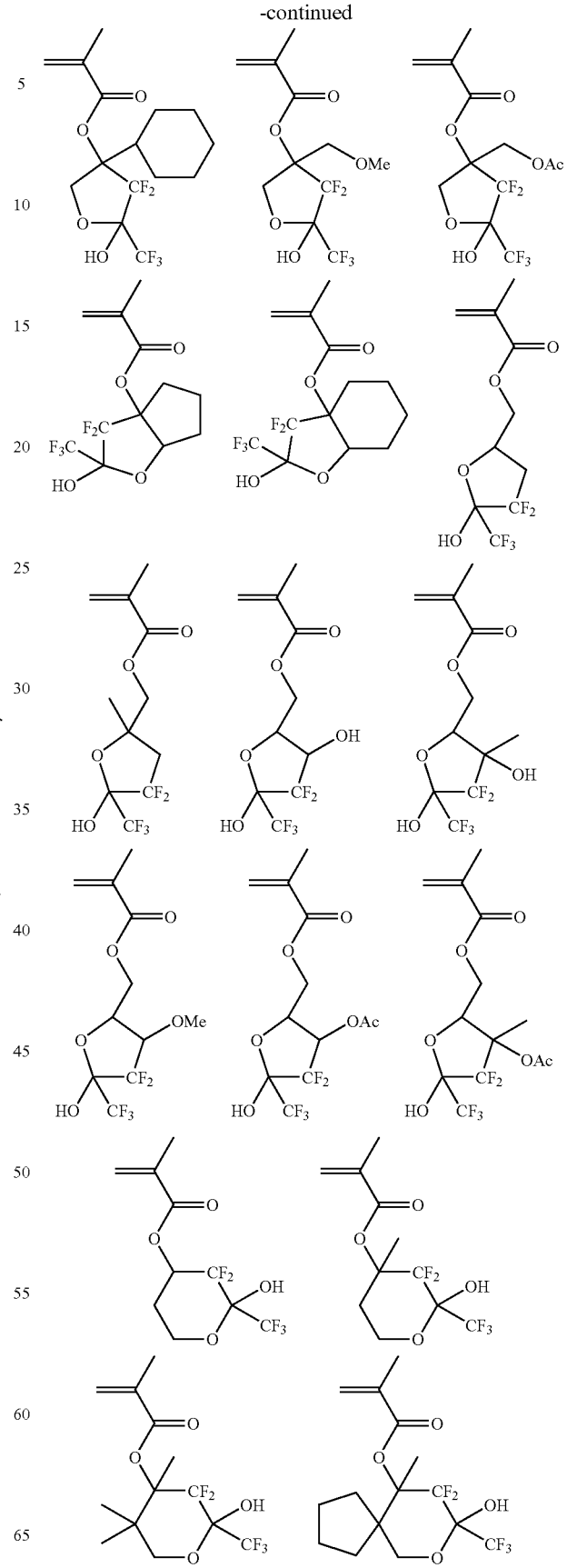

-continued
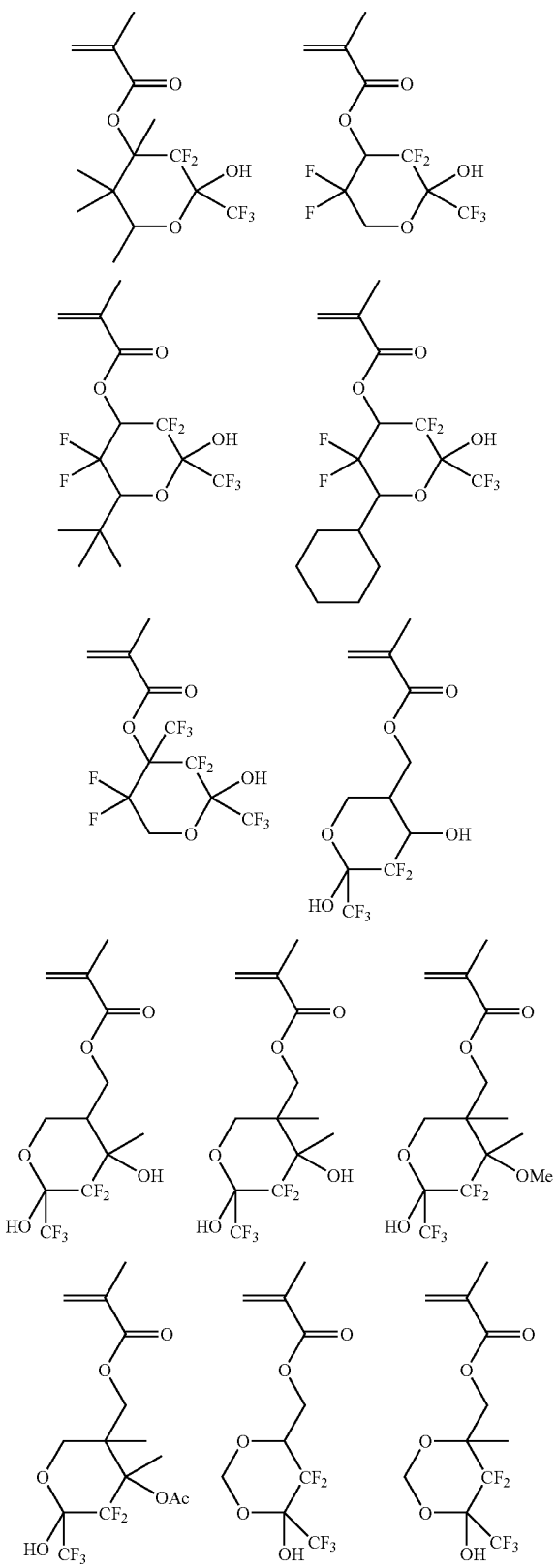
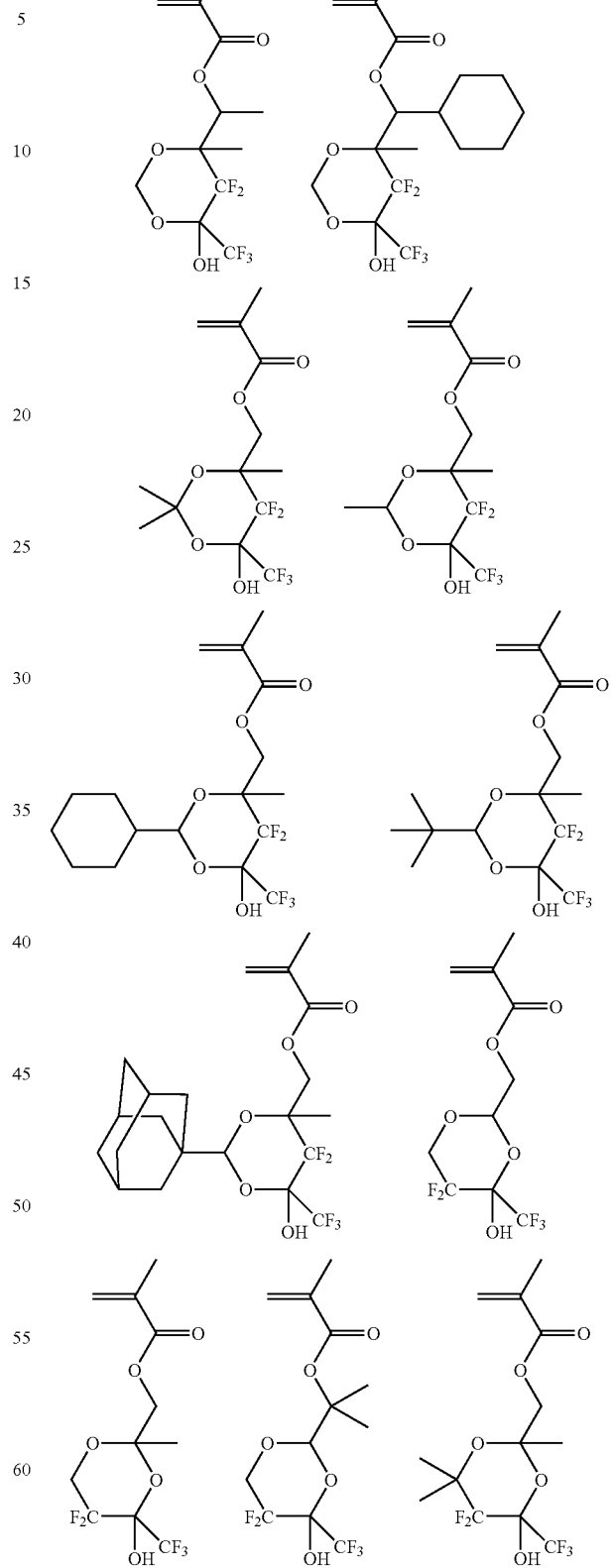

-continued
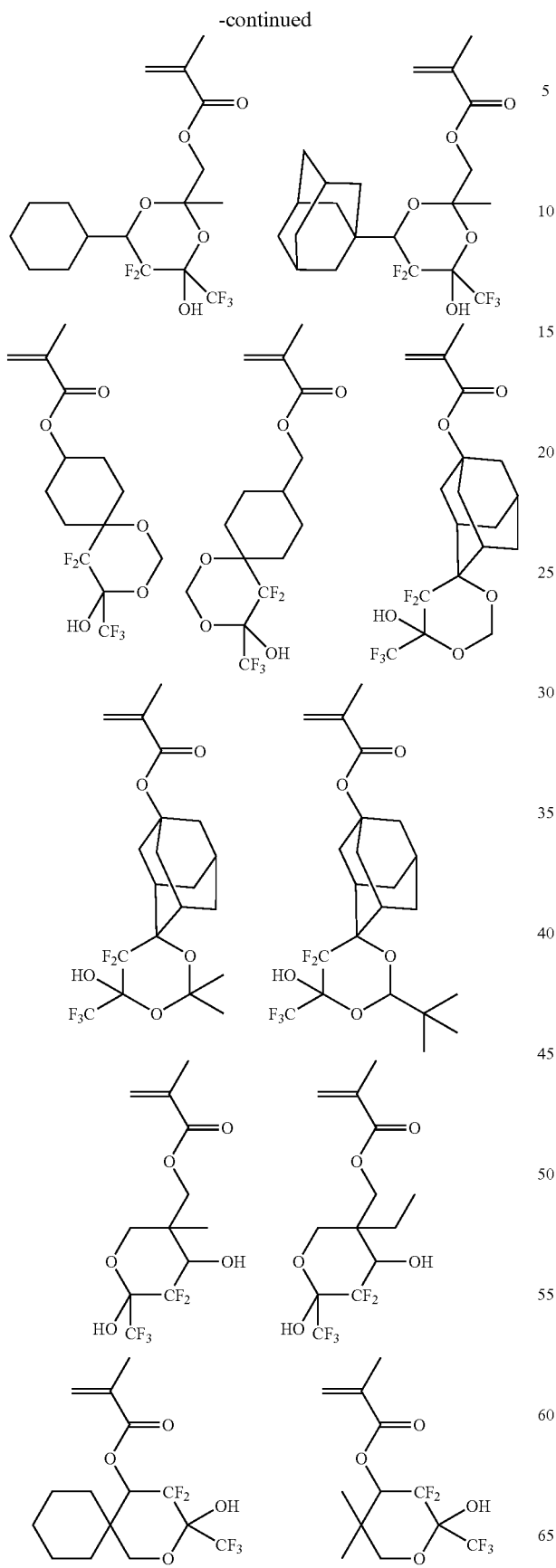
-continued
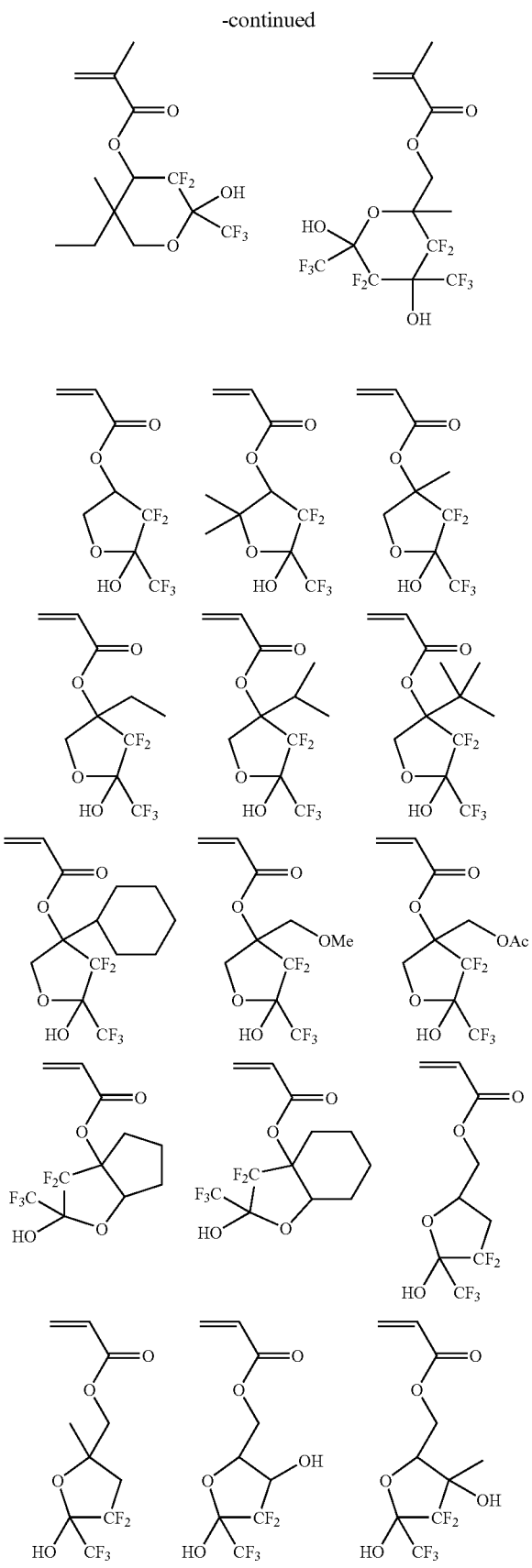

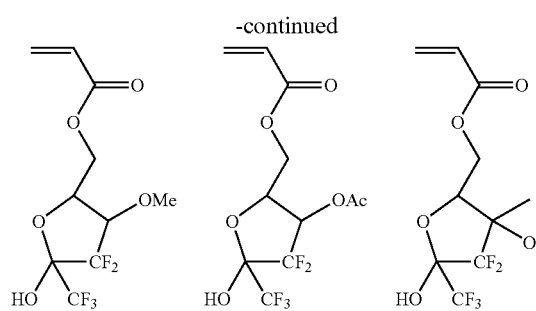
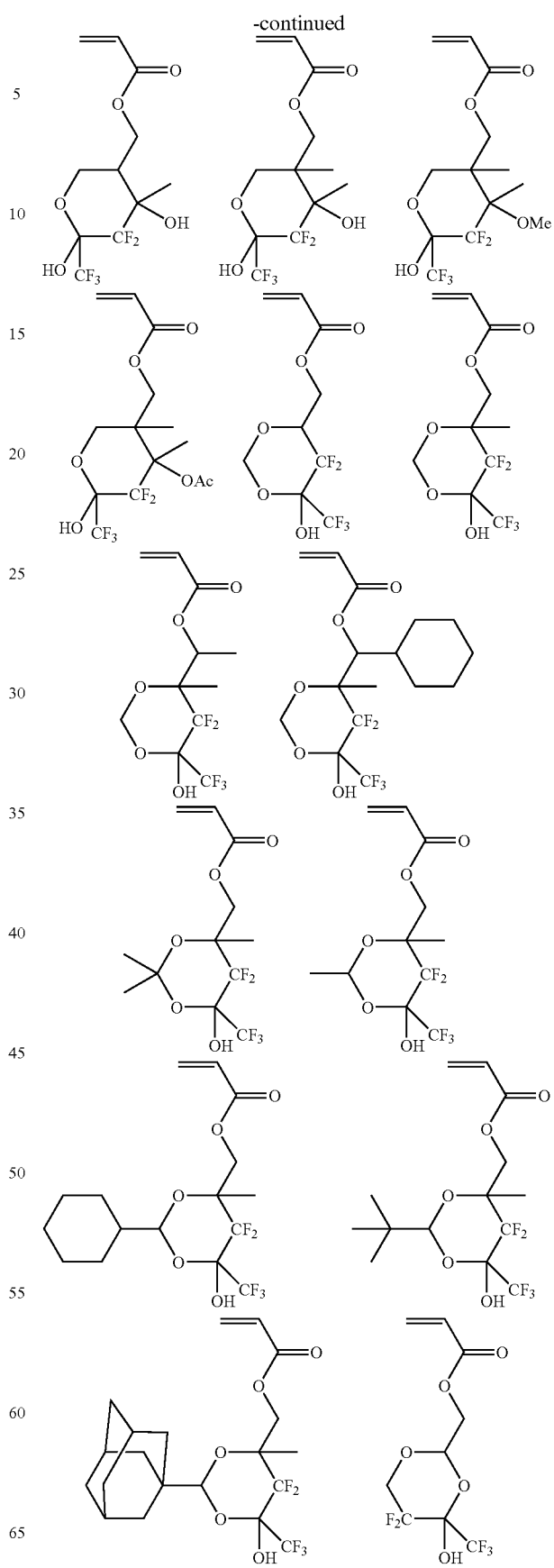

-continued
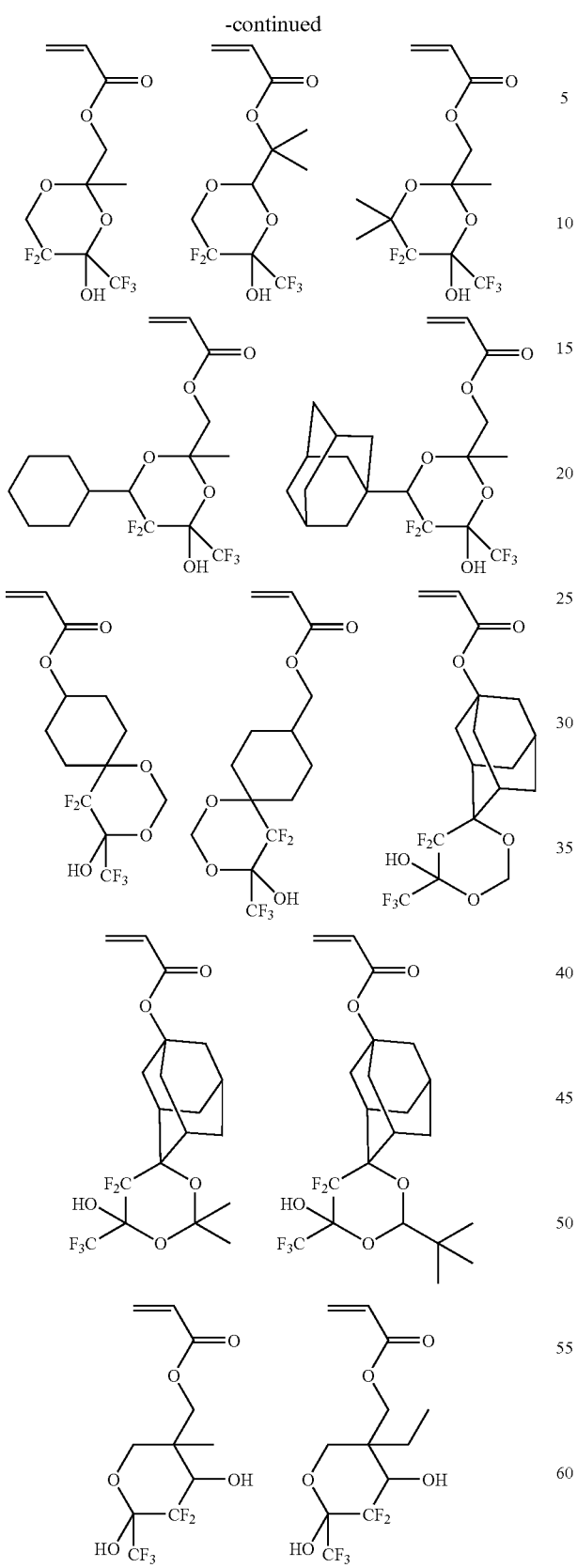
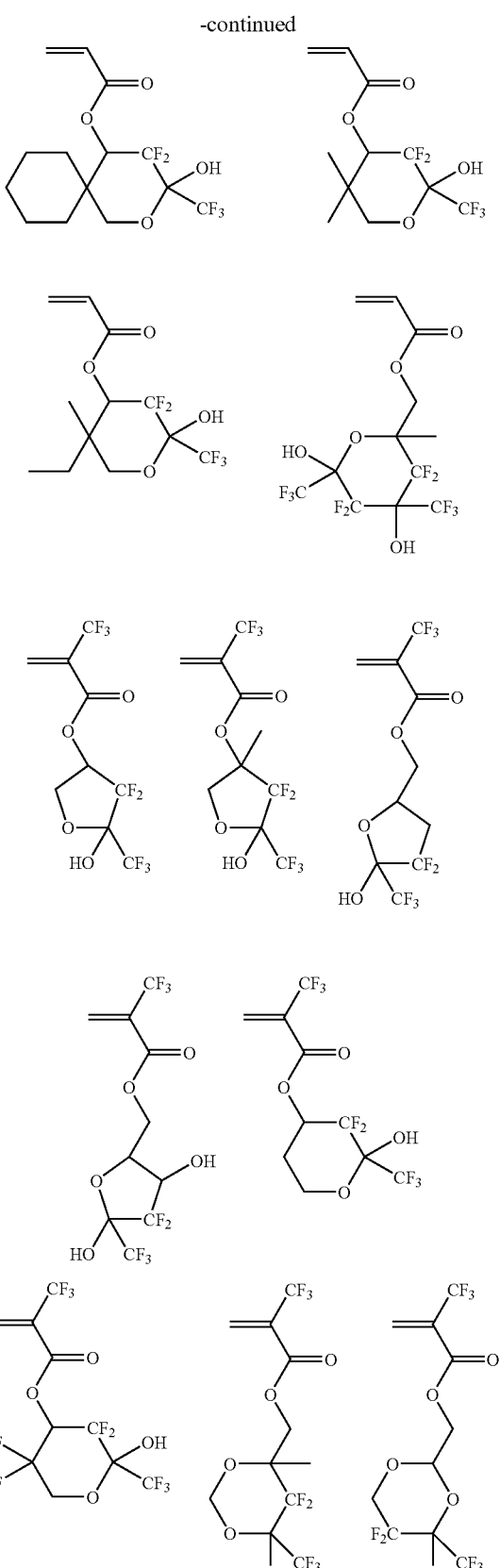

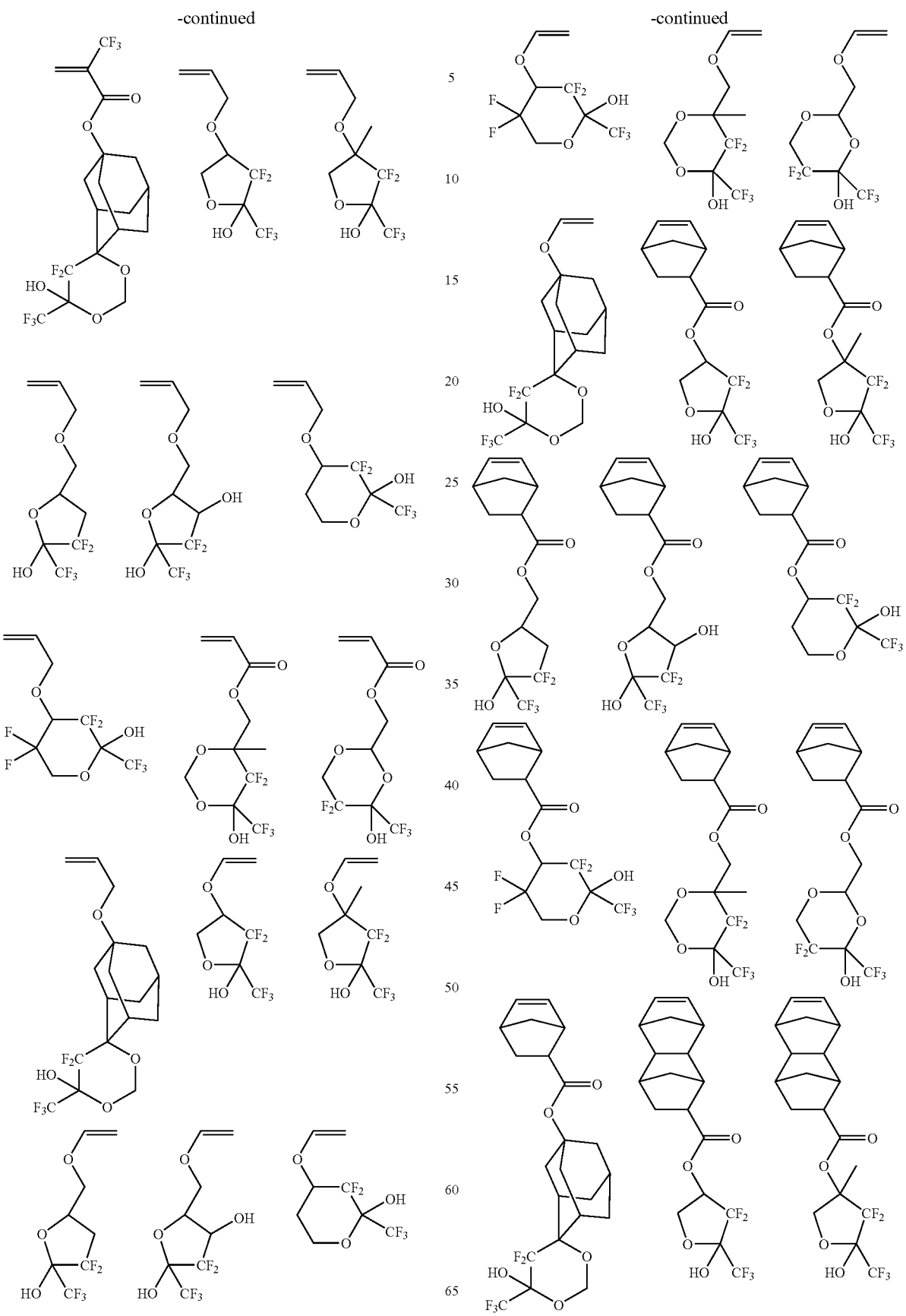

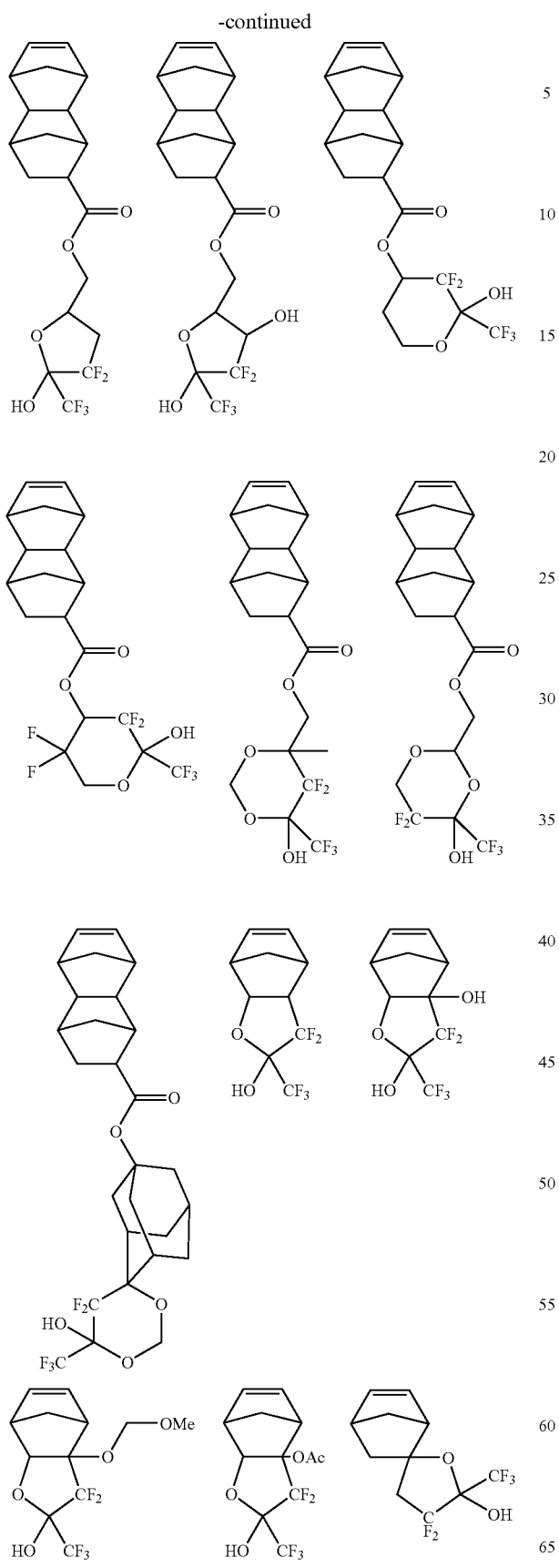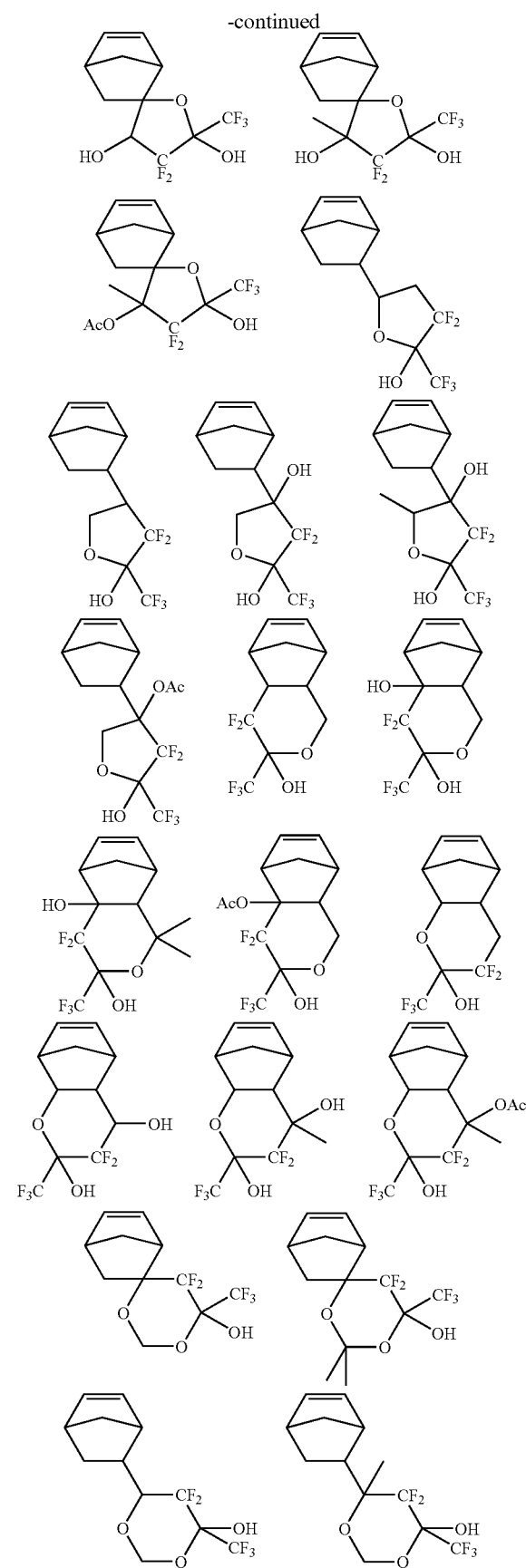

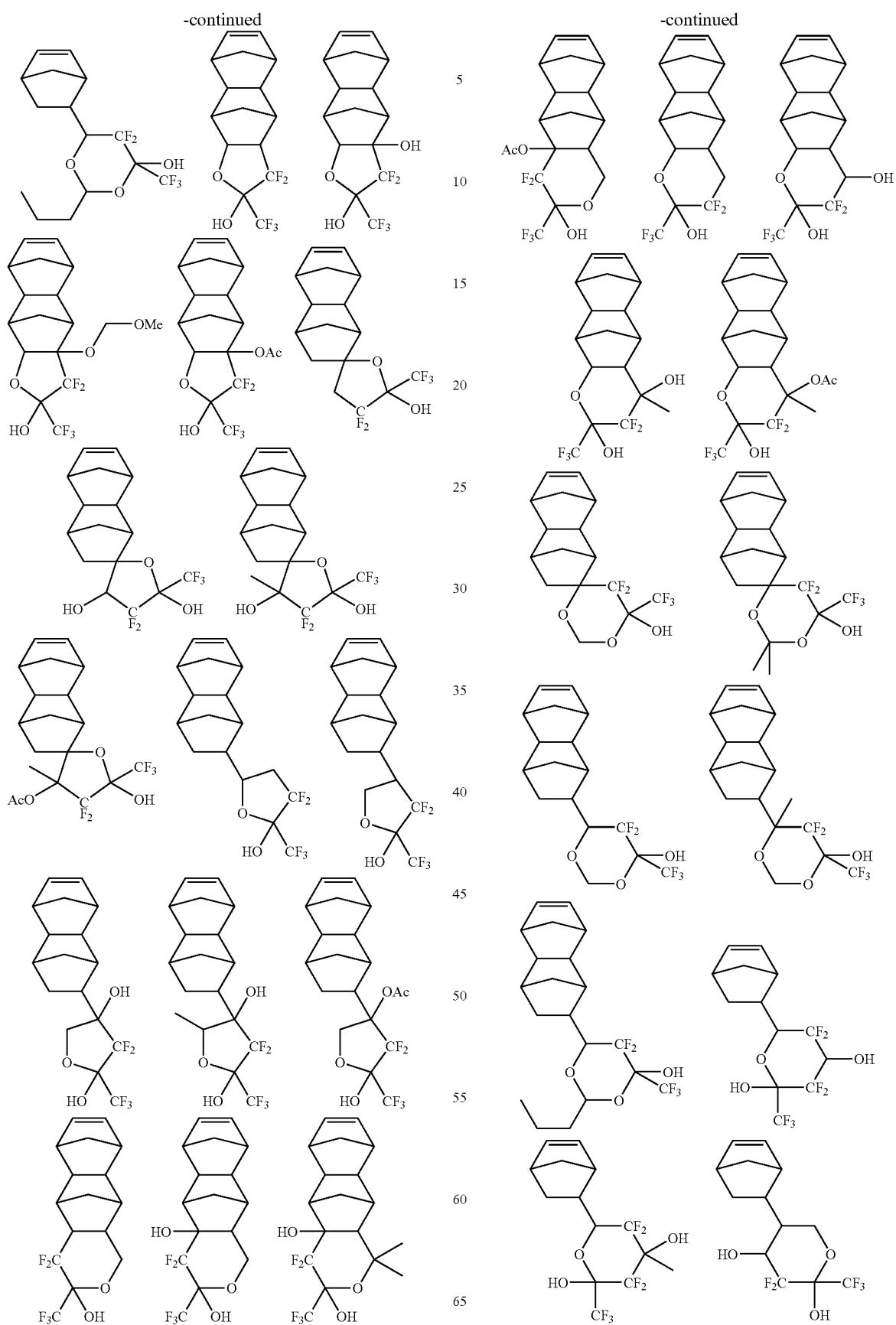

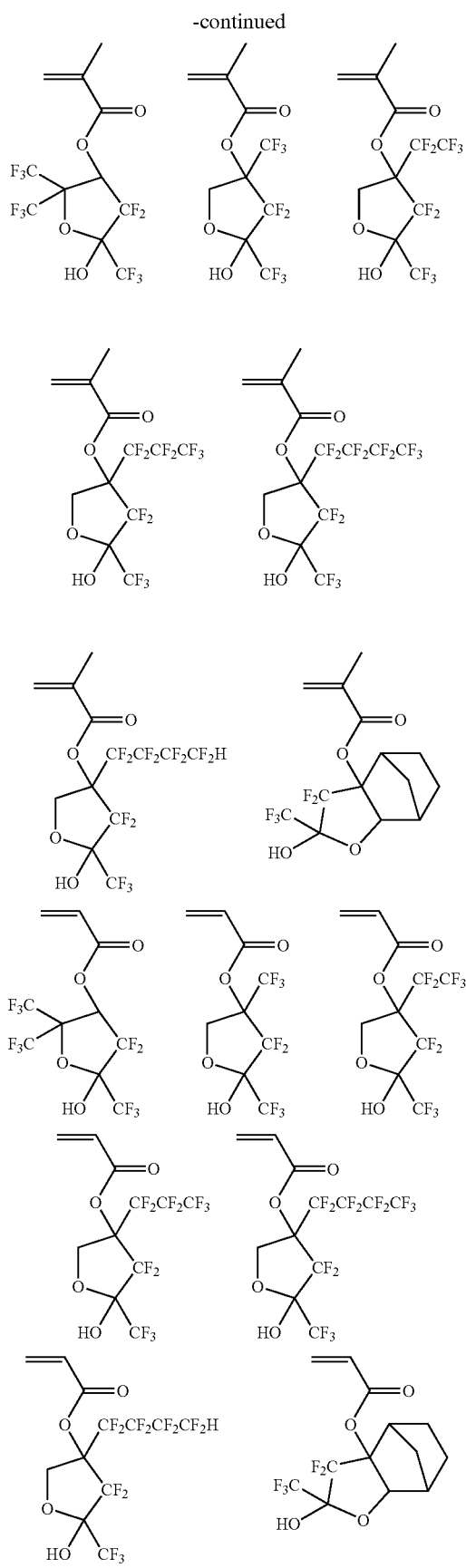

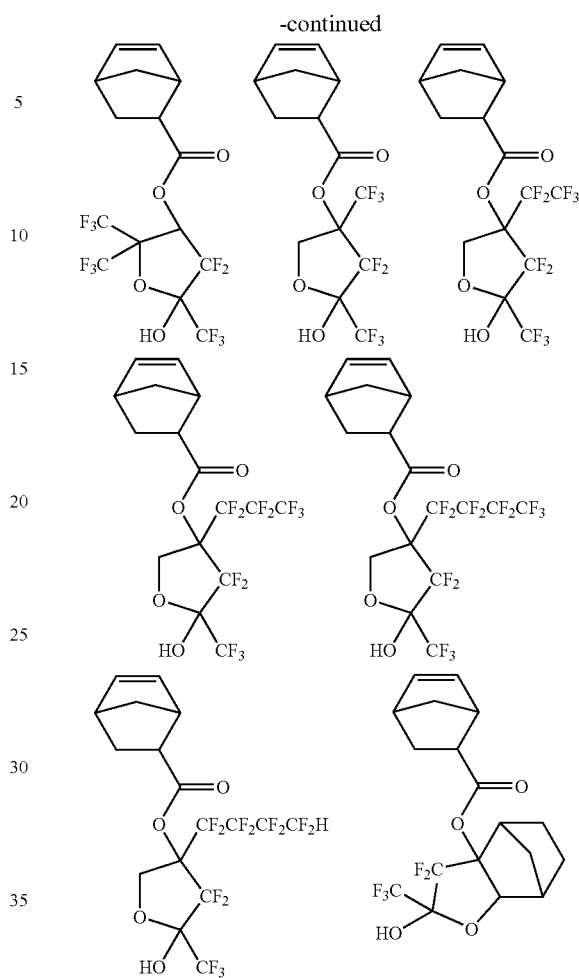

Preparation Method

The method of preparing the cyclic structure-bearing fluorinated monomers of the invention is described.

For the preparation of the cyclic structure-bearing fluorinated monomers having formulae (1), (2), (3) and (4) according to the invention, the key reaction is a reaction to form a hemiacetal ring. More specifically, the key is the step where a chain keto-alcohol compound having the general formula (9), (10), (11) or (12) undergoes cyclization into a hemiacetal compound having the general formula (13), (14), (15) or (16).

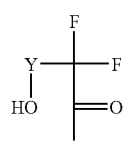

(9)

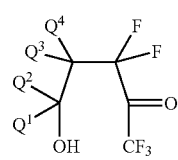

(10)

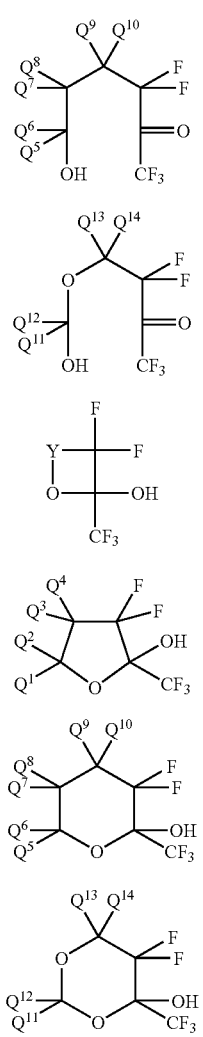

having a functional group which can be converted to a polymerizable unsaturated group. A combination of any, at least two of $Q^5$ to $Q^{10}$ may bond together to form a ring with the carbon atom or atoms to which they are attached, the ring contains a polymerizable unsaturated group or a functional group which can be converted to a polymerizable unsaturated group unless the remaining group or groups which do not relate to the ring formation contain a polymerizable unsaturated group or a functional group which can be converted to a polymerizable unsaturated group. $Q^{11}$, $Q^{12}$, $Q^{13}$, and $Q^{14}$ are each independently selected from among hydrogen, hydroxyl, halogen, and straight, branched or cyclic monovalent organic groups of 1 to 15 carbon atoms, at least one of $Q^{11}$, $Q^{12}$, $Q^{13}$, and $Q^{14}$ is a monovalent organic group containing a polymerizable unsaturated group or a monovalent organic group having a functional group which can be converted to a polymerizable unsaturated group. A combination of any, at least two of $Q^{11}$ to $Q^{14}$ may bond together to form a ring with the carbon atom or atoms to which they are attached, the ring contains a polymerizable unsaturated group or a functional group which can be converted to a polymerizable unsaturated group unless the remaining group or groups which do not relate to the ring formation contain a polymerizable unsaturated group or a functional group which can be converted to a polymerizable unsaturated group.

Herein, the general formula (9), (10), (11) or (12) represents not only keto-alcohol compounds themselves, but also corresponding alkoxide derivatives in which the hydroxyl group has been converted to an anion and triol derivatives in which the α,α,α,α',α'-pentafluorocarbonyl group has become hydrated. For convenience sake, they are generally referred to as keto-alcohol compounds. In the course of synthesis, the keto-alcohol compound having the general formula (9), (10), (11) or (12) need not necessarily be isolated. Often, the keto-alcohol compound may be formed in situ in a reaction system and a cyclized form be obtained eventually.

As discussed above, it is believed that these reactions proceed toward the formation of stable hemiacetal structure (13), (14), (15) or (16) for the reason that the open-chain keto-alcohol structure (9), (10), (11) or (12) has five electron-withdrawing fluorine atoms substituted on the carbon atoms adjacent the carbonyl group therein, allowing for an intramolecular nucleophilic attack by the hydroxyl group or alkoxide.

Where Y is a divalent organic group containing a polymerizable unsaturated group, where at least one of $Q^1$, $Q^2$, $Q^3$, and $Q^4$ is a monovalent organic group containing a polymerizable unsaturated group or the ring formed from at least two of $Q^1$ to $Q^4$ contains a polymerizable unsaturated group, where at least one of $Q^5$, $Q^6$, $Q^7$, $Q^8$, $Q^9$ and $Q^{10}$ is a monovalent organic group containing a polymerizable unsaturated group or the ring formed from at least two of $Q^5$ to $Q^{10}$ contains a polymerizable unsaturated group, or where at least one of $Q^{11}$, $Q^{12}$, $Q^{13}$, and $Q^{14}$ is a monovalent organic group containing a polymerizable unsaturated group or the ring formed from at least two of $Q^{11}$ to $Q^{14}$ contains a polymerizable unsaturated group, then the compound having the general formula (13), (14), (15) or (16) is the compound having the general formula (1), (2), (3) or (4) itself, meaning that the cyclization reaction is a method of preparing a cyclic structure-bearing fluorinated monomer of the present invention. A preparation method involving incorporating a polymerizable unsaturated group within the molecule prior to such hemiacetal cyclization reaction is effective particularly when the polymerizable unsaturated group is not affected by the hemiacetal cyclization reaction. Preferred such embodiments include as the structure having a polymerizable unsaturated group, unsaturated hydrocarbon structures such as bicyclo Herein Y is a divalent organic group containing a polymerizable unsaturated group or a divalent organic group having a functional group which can be converted to a polymerizable unsaturated group. $Q^1$, $Q^2$, $Q^3$, and $Q^4$ are each independently selected from among hydrogen, hydroxyl, halogen, and straight, branched or cyclic monovalent organic groups of 1 to 15 carbon atoms, at least one of $Q^1$, $Q^2$, $Q^3$, and $Q^4$ is a monovalent organic group containing a polymerizable unsaturated group or a monovalent organic group having a functional group which can be converted to a polymerizable unsaturated group. A combination of any, at least two of $Q^1$ to $Q^4$ may bond together to form a ring with the carbon atom or atoms to which they are attached, the ring contains a polymerizable unsaturated group or a functional group which can be converted to a polymerizable unsaturated group unless the remaining group or groups which do not relate to the ring formation contain a polymerizable unsaturated group or a functional group which can be converted to a polymerizable unsaturated group. $Q^5$, $Q^6$, $Q^7$, $Q^8$, $Q^9$ and $Q^{10}$ are each independently selected from among hydrogen, hydroxyl, halogen, and straight, branched or cyclic monovalent organic groups of 1 to 15 carbon atoms, at least one of $Q^5$, $Q^6$, $Q^7$, $Q^8$, $Q^9$ and $Q^{10}$ is a monovalent organic group containing a polymerizable unsaturated group or a monovalent organic group

[2.2.1]hept-2-ene, tricyclo[5.2.1.0$^{2,6}$]dec-8-ene, and tetracyclo[4.4.0.1$^{2,5}$.1$^{7,10}$]dodec-3-ene, and unsaturated ether structures such as vinyloxy and allyloxy. On the other hand, embodiments including as the structure having a polymerizable unsaturated group, α,β-unsaturated ketone structures such as vinyl ketone and isopropenyl ketone, α,β-unsaturated ester structures such as acrylic esters, methacrylic esters and α-trifluoromethylacrylic esters, and unsaturated hydrocarbon ester structures such as bicyclo[2.2.1]hept-5-ene-2-carboxylic esters and tetracyclo[4.4.0.1$^{2,5}$.1$^{7,10}$]dodec-8-ene-3-carboxylic esters are also applicable as long as reaction conditions are properly selected.

Where Y is a divalent organic group having a functional group which can be converted to a polymerizable unsaturated group, where at least one of $Q^1$, $Q^2$, $Q^3$, and $Q^4$ is a monovalent organic group having a functional group which can be converted to a polymerizable unsaturated group or the ring formed from at least two of $Q^1$ to $Q^4$ contains a functional group which can be converted to a polymerizable unsaturated group, where at least one of $Q^5$, $Q^6$, $Q^7$, $Q^8$, $Q^9$ and $Q^{10}$ is a monovalent organic group having a functional group which can be converted to a polymerizable unsaturated group or the ring formed from at least two of $Q^5$ to $Q^{10}$ contains a functional group which can be converted to a polymerizable unsaturated group, or where at least one of $Q^{11}$, $Q^{12}$, $Q^{13}$, and $Q^{14}$ is a monovalent organic group having a functional group which can be converted to a polymerizable unsaturated group or the ring formed from at least two of $Q^{11}$ to $Q^{14}$ contains a functional group which can be converted to a polymerizable unsaturated group, then the functional group must be converted to a polymerizable unsaturated group. The functional group which can be converted to a polymerizable unsaturated group may be selected from a variety of such groups, depending on the type of polymerizable unsaturated group. In typical embodiments wherein the structures having a polymerizable unsaturated group include unsaturated ether structures such as vinyloxy and allyloxy, α,β-unsaturated ester structures such as acrylic esters, methacrylic esters and α-trifluoromethylacrylic esters, and unsaturated hydrocarbon ester structures such as bicyclo[2.2.1]hept-5-ene-5-carboxylic esters and tetracyclo[4.4.0.1$^{2,5}$.1$^{7,10}$]dodec-8-ene-3-carboxylic esters, since these functional groups (polymerizable unsaturated group structures) can be synthesized through vinylation, allylation or acylation of hydroxyl groups, the functional groups which can be converted to a polymerizable unsaturated group are typically hydroxyl groups or those groups which can be converted to a hydroxyl group. Those groups which can be converted to a hydroxyl group include those containing a protected hydroxyl group which can be deprotected and converted to a hydroxyl group, and those containing aldehyde (formyl group) or ester (alkoxycarbonyl group) which can be converted into a hydroxyl group through chemical reduction or alkylating reaction. A choice of substituent group, reaction route and reaction conditions makes it possible to carry out such conversion at the same time.

Hemiacetal cyclization reaction is generally carried out in a solvent and preferably under basic or acidic conditions, although the exact reaction conditions vary widely with the structure of reaction substrate. Basic conditions are preferably such that a keto-alcohol compound forms an alkoxide. Suitable bases which can be used herein include organic bases such as triethylamine, diisopropylethylamine, N,N-dimethylaniline, pyridine, and 4-dimethylaminopyridine; inorganic bases such as sodium hydroxide, potassium hydroxide, barium hydroxide, sodium carbonate, sodium hydrogen carbonate, potassium carbonate, lithium hydride, sodium hydride, potassium hydride, and calcium hydride; alkyl metals such as methyllithium, n-butyllithium, methylmagnesium chloride, and ethylmagnesium bromide; and alkoxides such as sodium methoxide, sodium ethoxide, and potassium t-butoxide. In this case, although cyclization may be driven by treating an isolated keto-alcohol compound with such a base, it is preferred that the alkoxide formed in the course of synthesis of a keto-alcohol compound itself be used as such and subjected to cyclization. Suitable acids which can be used herein include mineral acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium (IV) methoxide, titanium(IV) ethoxide, titanium(IV) isopropoxide, and titanium(IV) oxide. In this case, although cyclization may be driven by treating an isolated keto-alcohol compound with such an acid, it is preferred that cyclization be incurred by acid treatment during work-up in the course of synthesis of a keto-alcohol compound itself. Suitable solvents which can be used herein include ethers such as diethyl ether, dibutyl ether, diethylene glycol diethyl ether, diethylene glycol dimethyl ether, tetrahydrofuran and 1,4-dioxane; hydrocarbons such as hexane, heptane, benzene, toluene, xylene and cumene; nitriles such as acetonitrile; and aprotic polar solvents such as N,N-dimethylformamide and hexamethylphosphoric triamide, alone or in admixture. The reaction temperature is preferably from −50° C. to approximately the boiling point of the solvent, and more preferably from −20° C. to 100° C. It is desirable from the yield standpoint to force the reaction to completion by tracing the reaction by gas chromatography (GC) or thin-layer chromatography (TLC), although the reaction time is usually about 0.1 to about 250 hours.

The method of preparing cyclization precursor keto-alcohol compounds having the general formula (9), (10), (11) or (12) differs with the structure, as will be described in subsequent Examples. Introduction of an α,α,α,α',α'-pentafluorocarbonyl group moiety may be carried out, for example, by reacting a carbonyl compound with 1,1,3,3,3-pentafluoro-2-propenyl oxide (see T. Nakai et al., Tetrahedron Letters, Vol. 29, p. 4119, 1988 and T. Nakai et al., Organic Syntheses, Vol. 76, p. 151, 1998) or by gem-fluorination reaction of an α,α, α-trifluoroketone at α',α'-positions with an electrophilic fluorinating reagent (see T. Hiyama, Organofluorine Compounds Chemistry and Applications, p. 25-39, 2000). In particular, the reaction of a carbonyl compound with 1,1,3,3, 3-pentafluoro-2-propenyl oxide is preferred because the desired pentafluoro-substituted partial structure can be introduced in a single procedure.

Described below in detail is the synthesis of the compound having a specific dioxane hemiacetal structure represented by formula (16). As discussed above, the keto-alcohol intermediate (12) is considered unstable in itself, and readily cyclizes into the dioxane hemiacetal compound (16). It is thus crucial how to synthesize the intermediate (12). The intermediate (12) can be synthesized, for example, by a synthesis route as shown below.

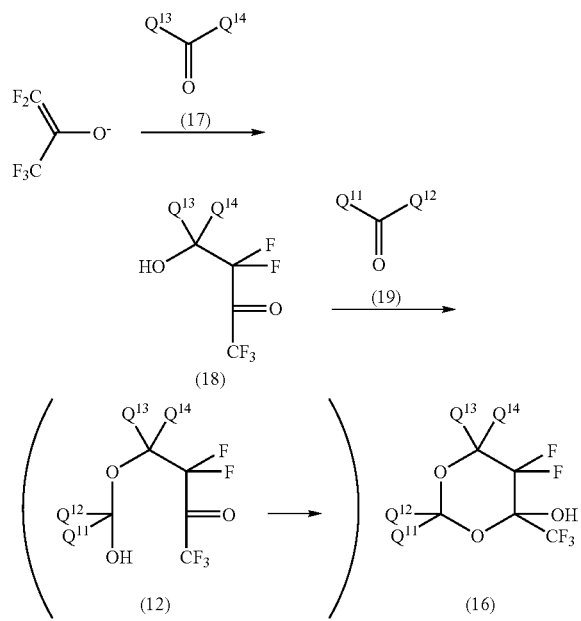

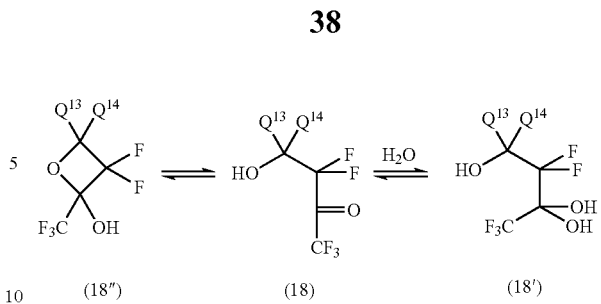

Herein, $Q^{11}$, $Q^{12}$, $Q^{13}$ and $Q^{14}$ are as defined above.

The first stage is an aldol condensation step to react 1,1,3,3,3-pentafluoro-2-propenyl oxide with a first carbonyl compound having formula (17) to form a keto-alcohol compound having formula (17). One reactant, 1,1,3,3,3-pentafluoro-2-propenyl oxide can be readily synthesized from 1,1,1,3,3,3-hexafluoro-2-propanol which is commercially available in bulk, has a melting point of −4° C. to −2° C. and a boiling point of 59-60° C., and is liquid at room temperature and easy to handle. The second stage is nucleophilic addition of the hydroxyl group in the intermediate (18) to the carbonyl group in a second carbonyl compound having formula (19) to form a keto-alcohol compound having formula (12). The intermediate (12) proceeds quick intramolecular cyclization, as discussed previously, converting to a hemiacetal compound having formula (16).

Herein, the intermediate keto-alcohol compounds having formulae (18) and (12) represent not only keto-alcohol compounds themselves, but also corresponding alkoxide derivatives in which the hydroxyl group has been converted to an anion and triol derivatives in which the α, α, α, α', α'-pentafluorocarbonyl group moiety has become hydrated. For convenience sake, they are generally referred to as keto-alcohol compounds.

Further, the compound (18) is available not only as a hydrated compound having formula (18'), shown below, as a result of addition of water to the carbonyl group by aqueous work-up, but also as an oxetane hemiacetal compound having formula (18"), shown below, as a result of the intramolecular addition of hydroxyl group to the internal carbonyl group, and also as a mixture of two or three of these species. In some cases, such a mixture may be used directly in subsequent reaction, and in some other cases, the equilibrium may be readily biased toward the keto-alcohol compound by simple dehydration operation, prior to the reaction. Therefore, these compounds are generally represented by the formula (18).

In the course of synthesis, the keto-alcohol compound does not need to be isolated. The keto-alcohol compound formed in situ in the reaction system may be used directly in the subsequent conversion. For example, one-pot reaction wherein all steps including the first step to form the alkoxide corresponding to formula (18), the second step to add a carbonyl compound (19) to the alkoxide (18), and the third step to effect cyclization via the alkoxide corresponding to formula (12) into a compound of formula (16) within the system are carried out in a common reactor is simple and of great industrial worth because extracting and purifying operations between the steps are unnecessary.

The carbonyl compound (17) used in the first step may be selected from various aldehyde and ketone compounds, depending on the structure of the final target compound. The reaction is generally carried out in a solvent and in an atmosphere of inert gas such as nitrogen or argon. The preferred solvent used herein is an ether such as diethyl ether, dibutyl ether, diethylene glycol diethyl ether, diethylene glycol dimethyl ether, tetrahydrofuran or 1,4-dioxane. Alternatively, hydrocarbons such as hexane, heptane, benzene, toluene, xylene and cumene; nitriles such as acetonitrile; and aprotic polar solvents such as N,N-dimethylformamide and hexamethylphosphoric triamide may be used alone or in admixture. The reaction temperature is preferably from −50° C. to approximately the boiling point of the solvent, and more preferably from −20° C. to 100° C. It is desirable from the yield standpoint to force the reaction to completion by tracing the reaction by gas chromatography (GC) or thin-layer chromatography (TLC), although the reaction time is usually about 0.1 to about 250 hours. After the completion of reaction, the alkoxide product may be used in the subsequent step without further purification or the compound (18) may be isolated by conventional aqueous work-up.

The carbonyl compound (19) used in the second step may be selected from various aldehyde and ketone compounds, depending on the structure of the final target compound. Preferred are relatively low molecular weight carbonyl compounds such as formaldehyde, acetaldehyde, propionaldehyde, pivalaldehyde, benzaldehyde, cyclohexanecarboxaldehyde, acetone, methyl ethyl ketone, cyclopentanone, and cyclohexanone. Also, any of carbonyl compound equivalents may be used directly or while a corresponding carbonyl compound is formed within the system, suitable carbonyl compound equivalents including acetals such as dimethoxymethane, trioxane, and acetaldehyde diethyl acetal; gem-dihalides such as dibromomethane and 1,1-dibromoethane; and α-haloethers such as chloromethyl methyl ether and chloromethyl ethyl ether. Reaction conditions widely vary depending on the type of substrate and reagent used. In one example where the alkoxide formed in the first step is directly used, the reaction is generally carried out in an atmosphere of inert gas such as nitrogen or argon and in a solvent to which the carbonyl compound (19) is added. The solvent used herein is as listed in the first step and may be the same or different from that used in the first step. In another example using the isolated keto-alcohol compound (18) and an acetal as the carbonyl compound equivalent, the desired conversion may be attained by equilibration reaction in the presence of an acid catalyst. Examples of the acid catalyst include mineral acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide; and acidic ion-exchange resins such as Amberlist® 15. If the reagent or substrate itself has acidity, the addition of another catalyst may be sometimes unnecessary. In a further example using the isolated keto-alcohol compound (18) and an α-halo ether or gem-dihalide as the carbonyl compound equivalent, conditions allowing the hydroxyl group to be alkylated in the presence of a base are preferred. A solvent is used which is selected from chlorinated solvents such as methylene chloride, chloroform and trichloroethylene, hydrocarbons such as hexane, heptane, benzene, toluene, xylene and cumene, ethers such as dibutyl ether, diethylene glycol diethyl ether, diethylene glycol dimethyl ether, tetrahydrofuran and 1,4-dioxane, nitriles such as acetonitrile, ketones such as acetone and 2-butanone, esters such as ethyl acetate and n-butyl acetate, and aprotic polar solvents such as N,N-dimethylformamide, dimethyl sulfoxide and hexamethylphosphoric triamide, alone or in admixture. The bases used herein include triethylamine, diisopropylethylamine, N,N-dimethylaniline, pyridine, and 4-dimethylaminopyridine. The reactants and the base may be sequentially or simultaneously fed to the solvent whereupon reaction takes place. The reaction temperature is preferably from −50° C. to approximately the boiling point of the solvent, and more preferably from −20° C to 100° C. It is desirable from the yield standpoint to force the-reaction to completion by tracing the reaction by gas chromatography (GC) or thin-layer chromatography (TLC), although the reaction time is usually about 0.1 to about 250 hours. After the completion of reaction, the alkoxide product may be used in the subsequent step without further purification or the dioxane hemiacetal compound (16) may be isolated by conventional aqueous work-up.

Polymer

Using the cyclic structure-bearing fluorinated monomers having formula (1), (2), (3) or (4) thus obtained, polymers comprising recurring units having the general formula (1a), (2a), (3a) or (4a), which may be homopolymers or copolymers, can be prepared by conventional techniques like radical polymerization, anionic polymerization and cationic polymerization. In forming copolymers, the fluorinated monomer is copolymerized with another polymerizable monomer of at least one type. Polymer preparation may employ well-known technique and conditions that allow polymerizable unsaturated bonds, especially polymerizable double bonds to be polymerized.

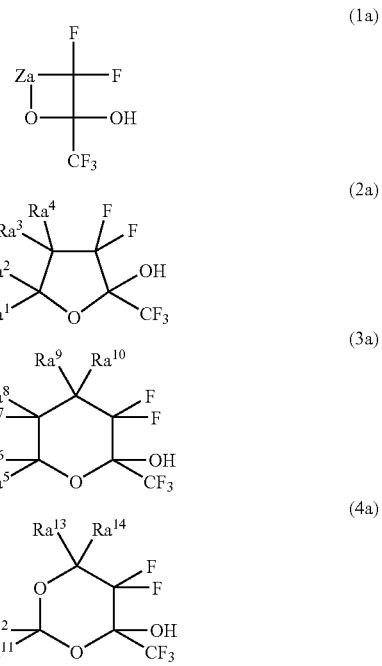

Herein Za is an organic group which is derived from a divalent organic group containing a polymerizable unsaturated group, represented by Z in formula (1), and which contains a polymeric main chain of recurring units in a polymer obtained through polymerization of said polymerizable unsaturated group. $Ra^1$, $Ra^2$, $Ra^3$, and $Ra^4$ are each independently selected from among hydrogen, hydroxyl, halogen, and straight, branched or cyclic monovalent organic groups of 1 to 15 carbon atoms, at least one of $Ra^1$, $Ra^2$, $Ra^3$, and $Ra^4$ is an organic group which is derived from a monovalent organic group containing a polymerizable unsaturated group, represented by at least one of $R^1$ to $R^4$ in formula (2), and which contains a polymeric main chain of recurring units in a polymer obtained through polymerization of said polymerizable unsaturated group. A combination of any, at least two of $Ra^1$ to $Ra^4$ may bond together to form a ring with the carbon atom or atoms to which they are attached, the ring may contain a polymeric main chain of recurring units in a polymer derived from a polymerizable unsaturated group and obtained through polymerization of said polymerizable unsaturated group. $Ra^5$, $Ra^6$, $Ra^7$, $Ra^8$, $Ra^9$ and $Ra^{10}$ are each independently selected from among hydrogen, hydroxyl, halogen, and straight, branched or cyclic monovalent organic groups of 1 to 15 carbon atoms, at least one of $Ra^5$ to $Ra^{10}$ is an organic group which is derived from a monovalent organic group containing a polymerizable unsaturated group, represented by at least one of $R^5$ to $R^{10}$ in formula (3), and which contains a polymeric main chain of recurring units in a polymer obtained through polymerization of said polymerizable unsaturated group. A combination of any, at least two of $Ra^5$ to $Ra^{10}$ may bond together to form a ring with the carbon atom or atoms to which they are attached, the ring contains a polymeric main chain of recurring units in a polymer derived from a polymerizable unsaturated group and obtained through polymerization of said polymerizable unsaturated group. $Ra^{11}$, $Ra^{12}$, $Ra^{13}$, and $Ra^{14}$ are each independently selected from among hydrogen, hydroxyl, halogen, and straight, branched or cyclic monovalent organic groups of 1 to 15 carbon atoms, at least one of $Ra^{11}$, $Ra^{12}$, $Ra^{13}$, and $Ra^{14}$ is an organic group which is derived from a monovalent organic group containing a polymerizable unsaturated group, represented by at least one of $R^{11}$ to $R^{14}$ in formula (4), and which contains a polymeric main chain of recurring units in a polymer obtained through polymerization of said polymerizable unsaturated group. A combination of any, at least two of $Ra^{11}$ to $Ra^{14}$ may bond together to form a ring with the carbon atom or atoms to which they are attached, the ring contains a polymeric main chain of recurring units in a polymer derived from a polymerizable unsaturated group and obtained through polymerization of said polymerizable unsaturated group.

The monovalent organic groups of 1 to 15 carbon atoms, the rings formed, and the polymerizable unsaturated groups are as previously exemplified.

In a preferred embodiment, a polymeric main chain of recurring units in a polymer obtained through polymerization of the polymerizable unsaturated group in formula (1a), (2a), (3a) or (4a) has an acrylic ester, methacrylic ester or α-trifluoromethylacrylic ester structure as shown by the general formula (5a):

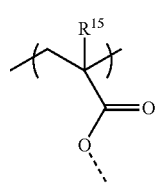

(5a)

wherein $R^{15}$ is hydrogen, methyl or trifluoromethyl, and the broken line denotes a valence bond. Such polymers are most preferred because they can be readily prepared by a radical polymerization or similar polymerization technique which can be industrially implemented and because of an increased freedom of choice of another monomer to be copolymerized therewith.

The way in which formula (5a) is included in an organic group containing a polymeric main chain of recurring units among $Ra^1$ to $Ra^{14}$ is the way in which the group of formula (5a) may be constituted as the organic group containing a polymeric main chain of recurring units among $Ra^1$ to $Ra^{14}$ and the valence bond of formula (5a) is directly bonded to the above-defined carbon atom "C", or the way in which the valence bond of formula (5a) may be bonded via the above-described divalent connecting group (preferably a linear, branched or cyclic alkylene group having 1 to 10 carbon atoms) to the carbon atom "C".

Illustrative examples of the recurring units having formula (1a), (2a), (3a) or (4a) are given below, but are not limited thereto.

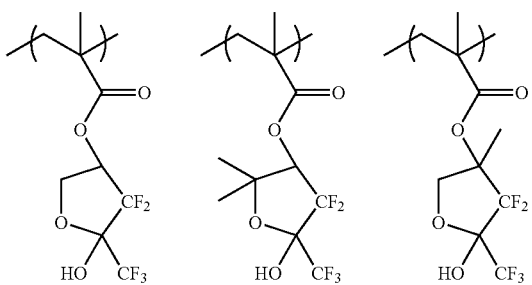

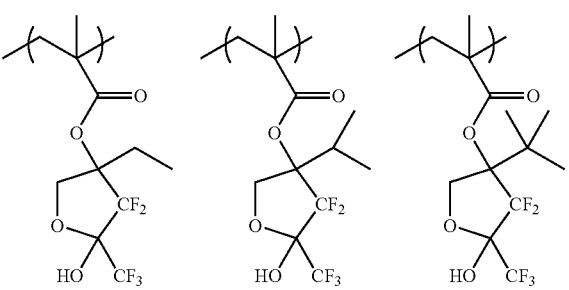

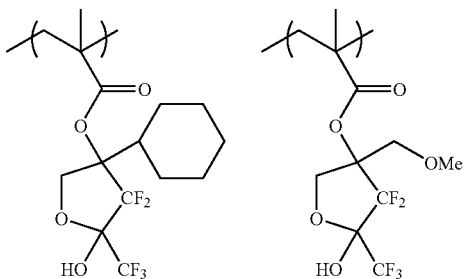

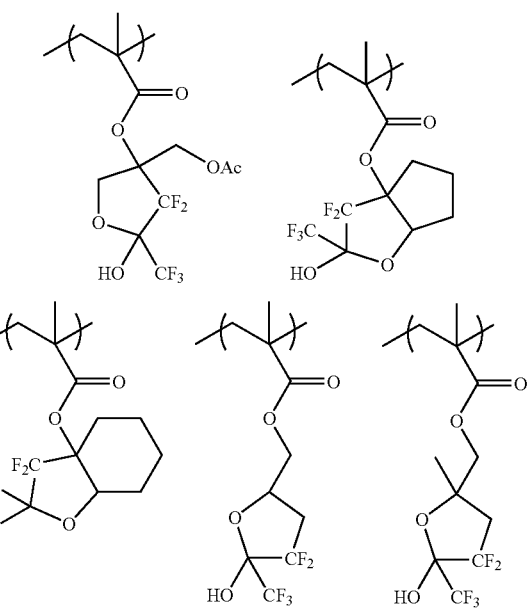

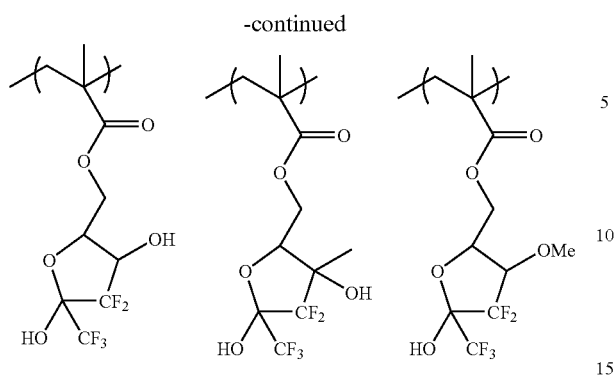
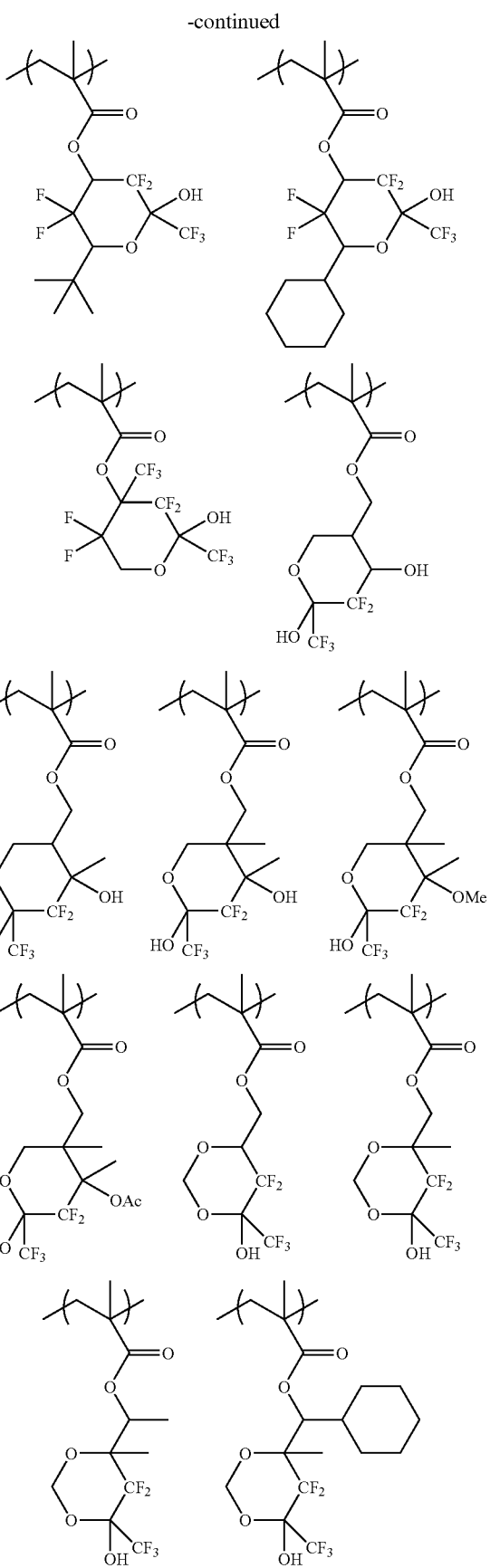

-continued
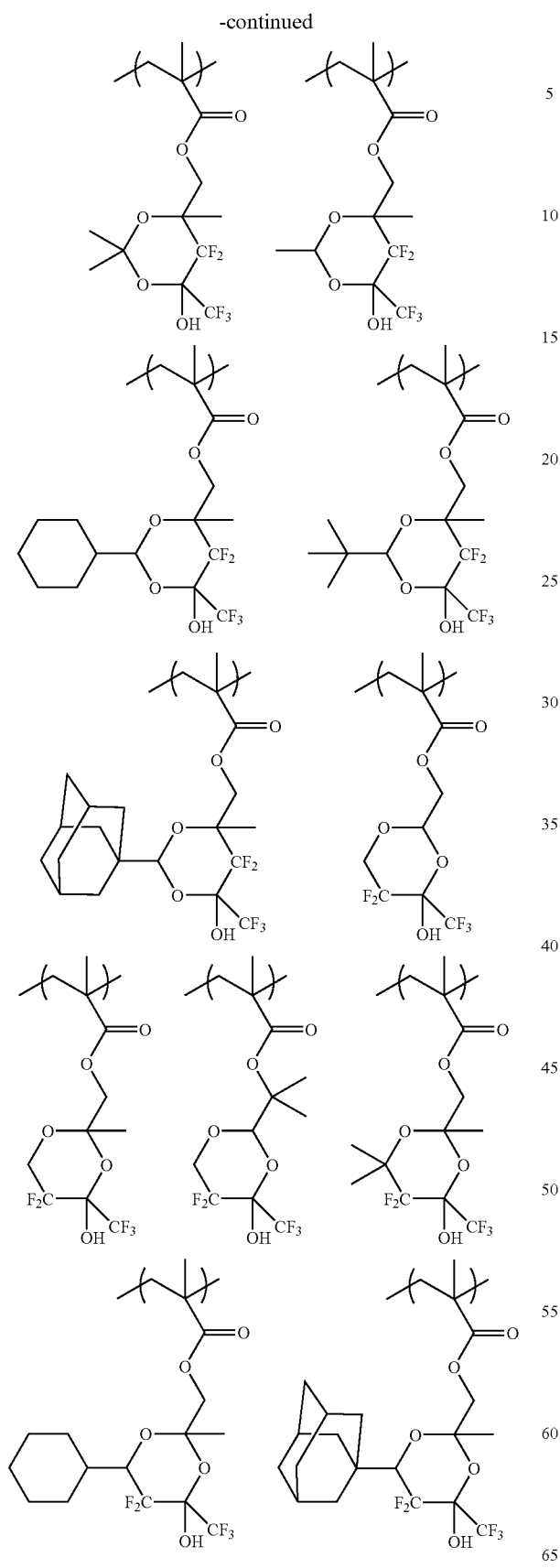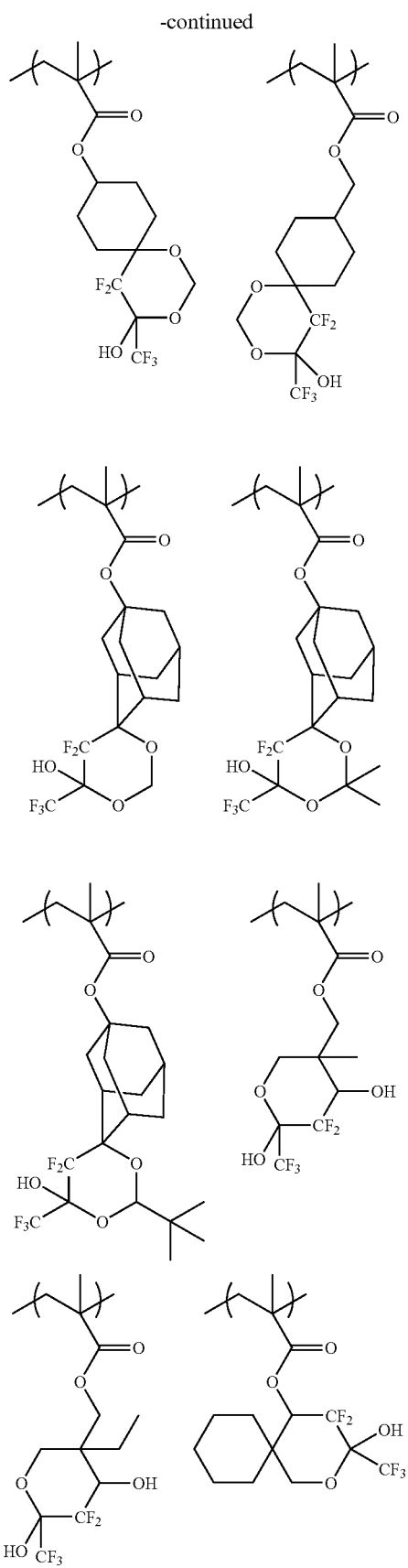

-continued
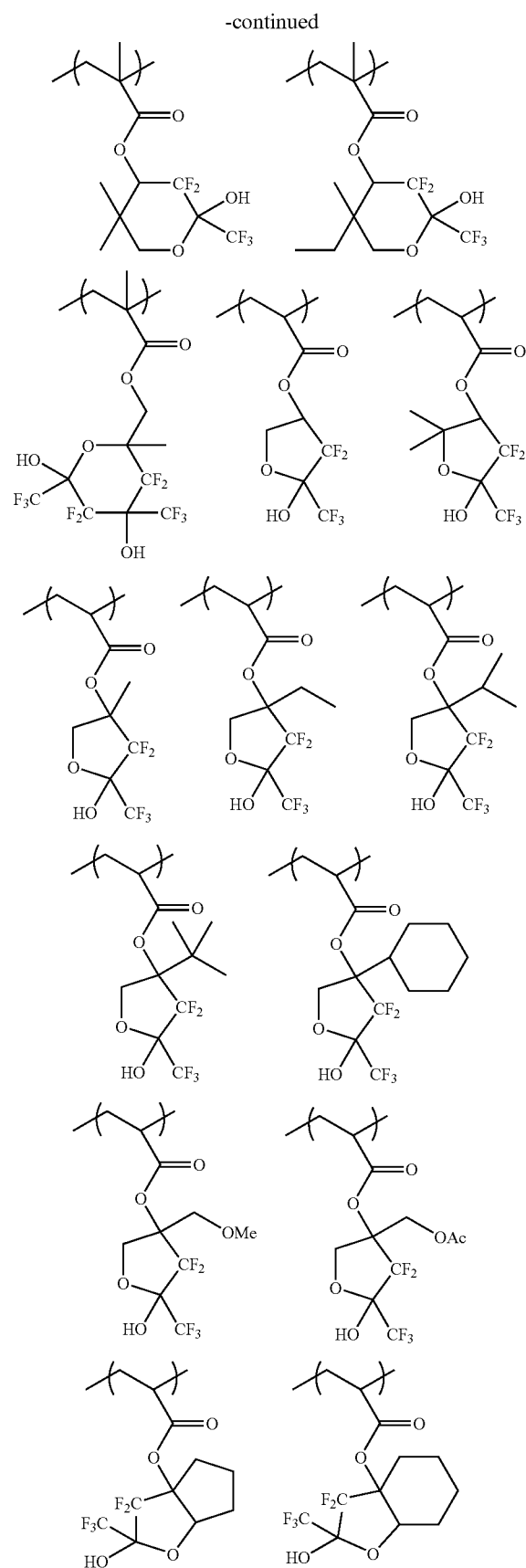
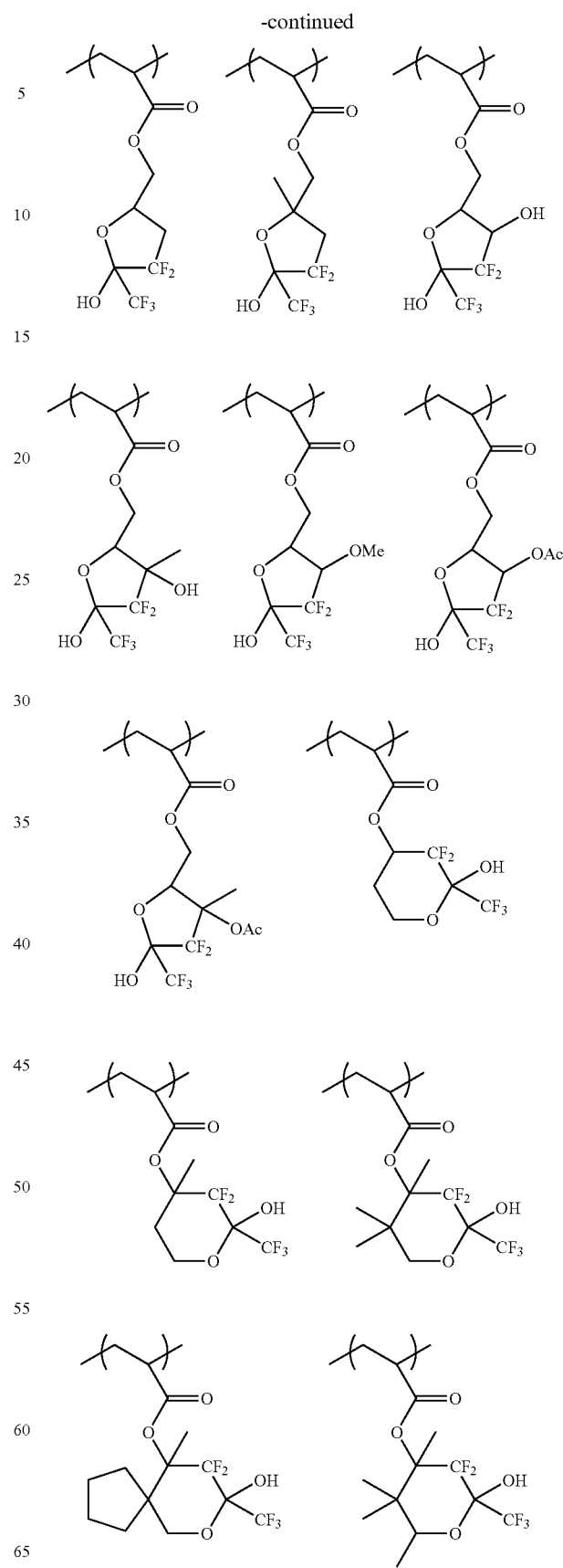

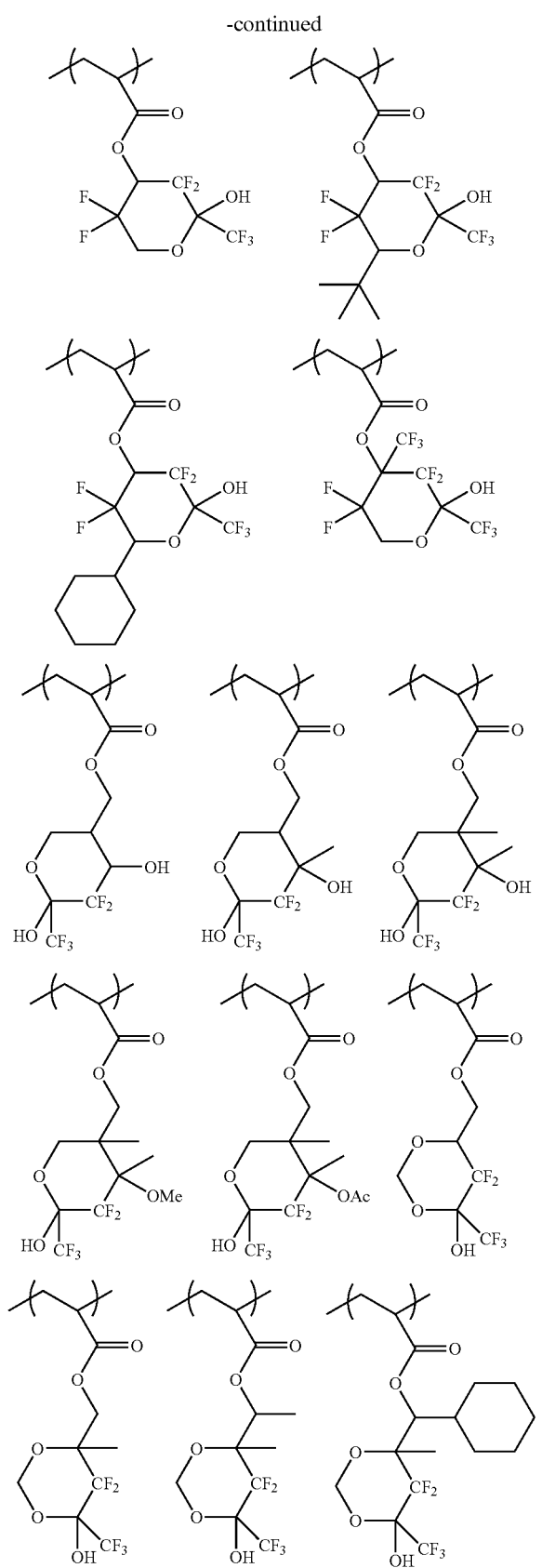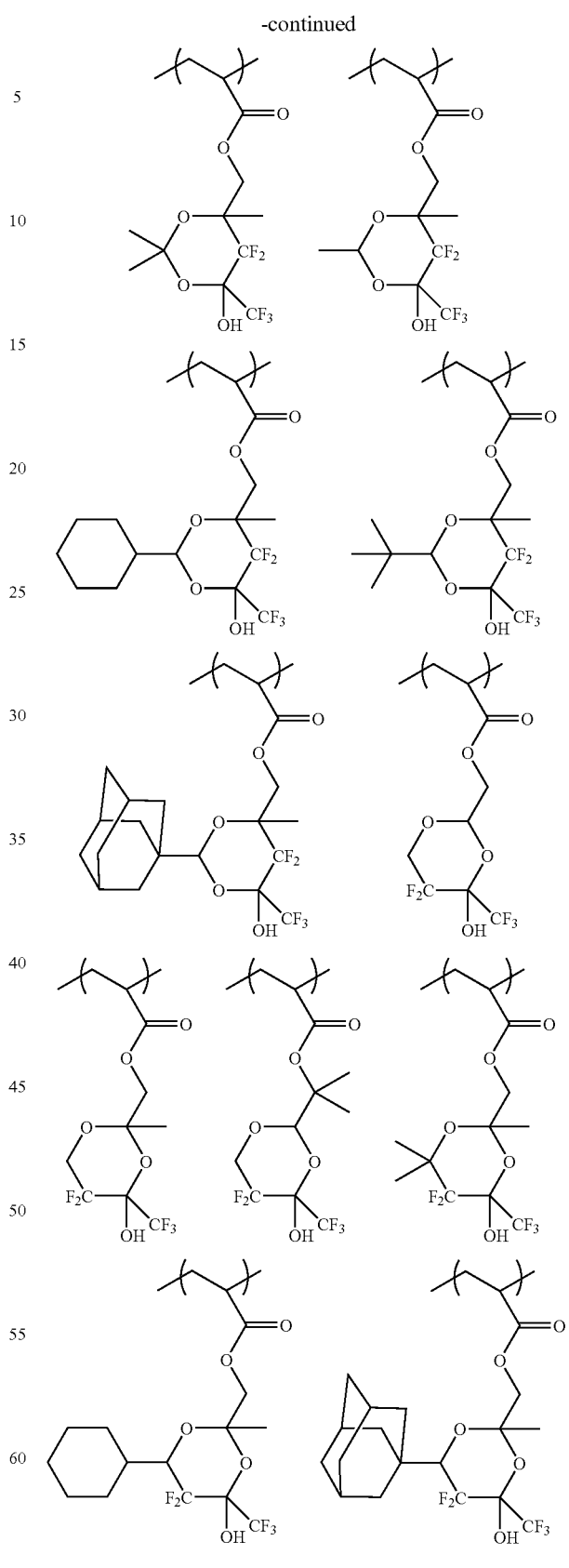

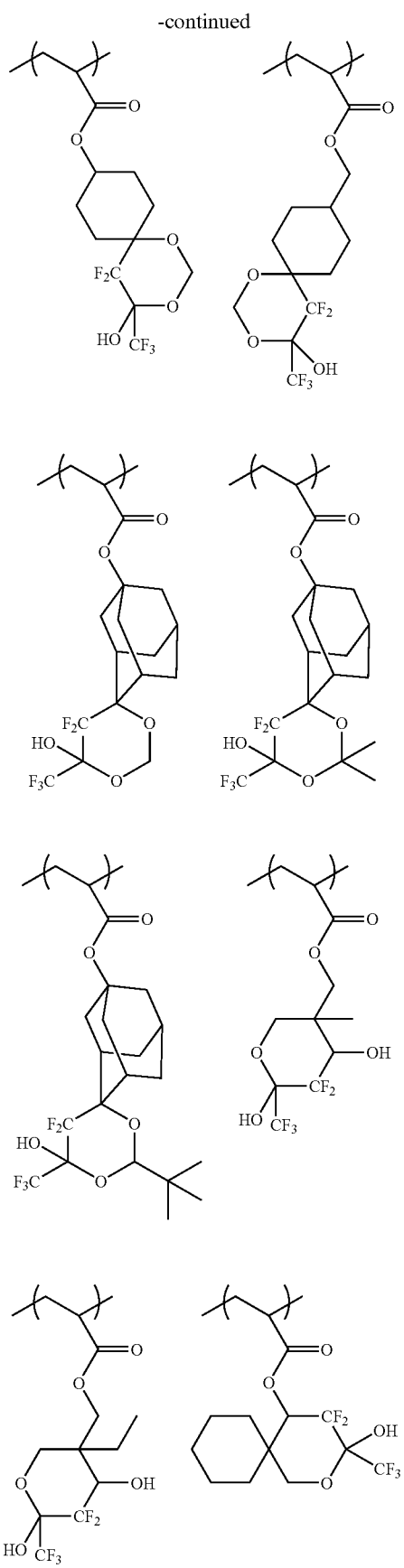
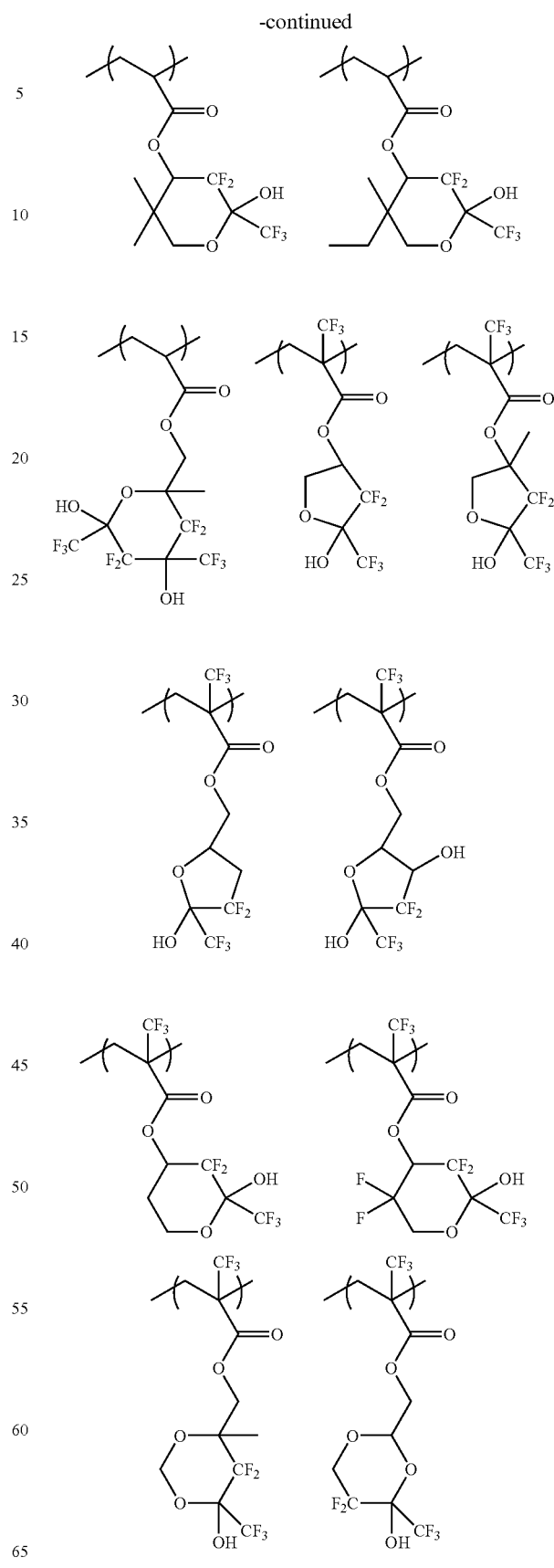

-continued
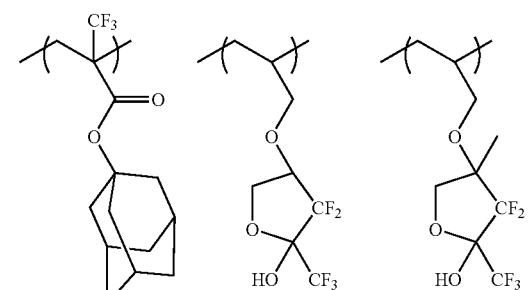
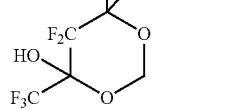
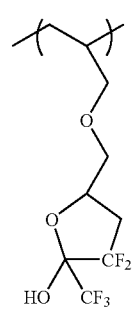
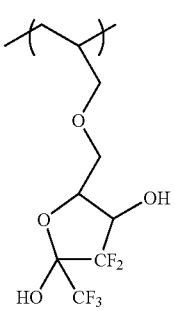
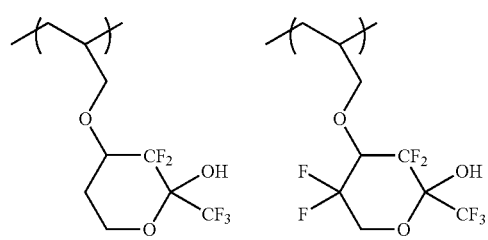
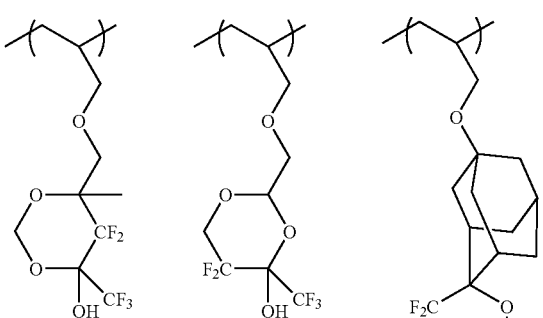
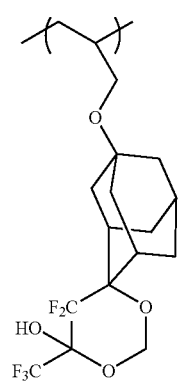
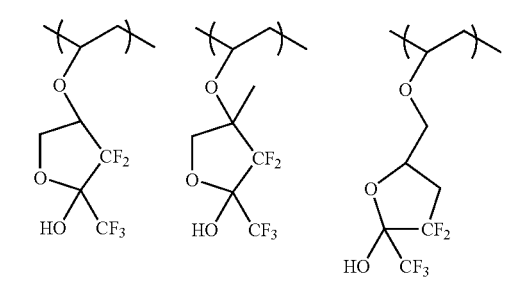
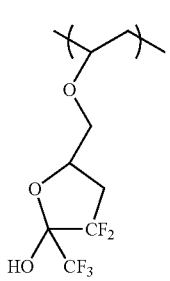
-continued
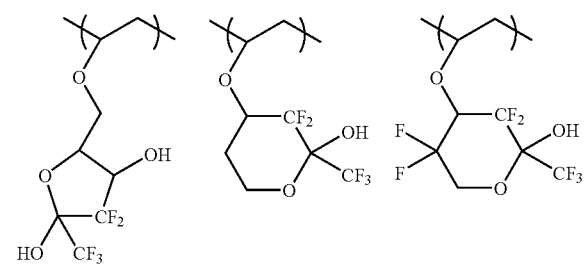
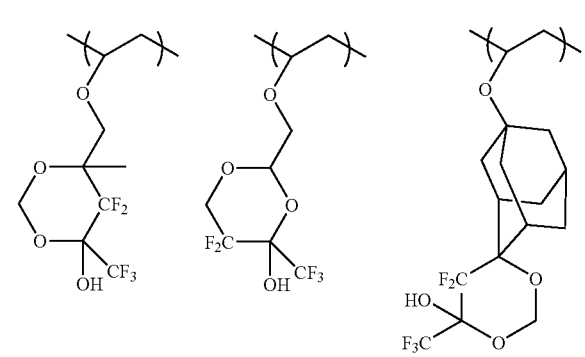
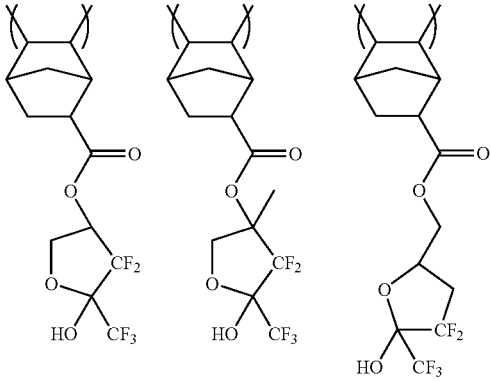
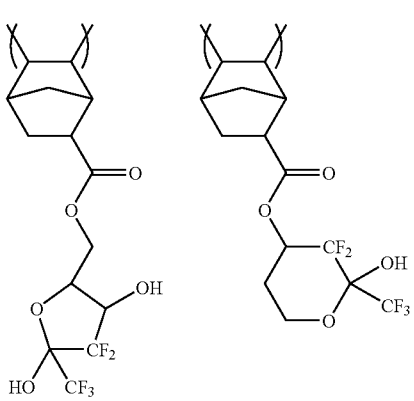

-continued
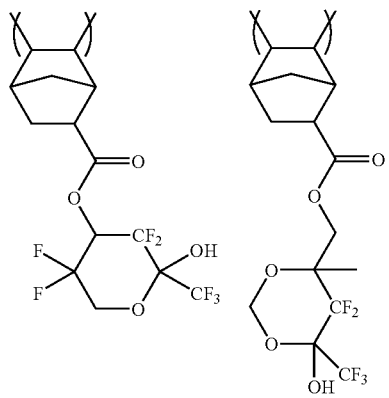
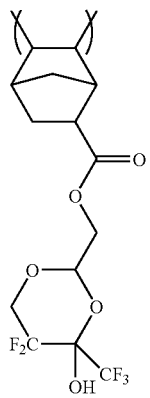
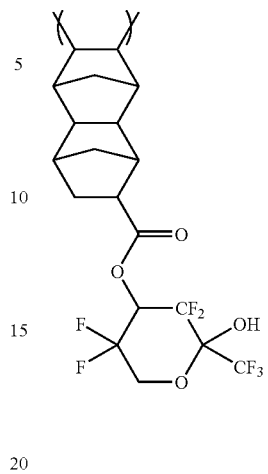
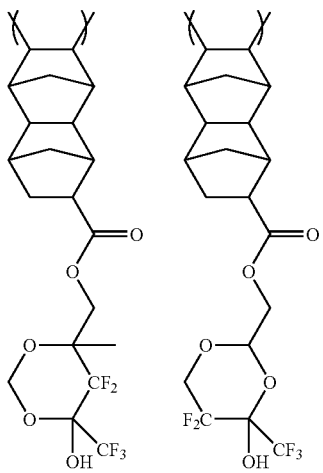
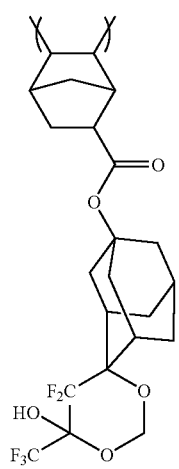
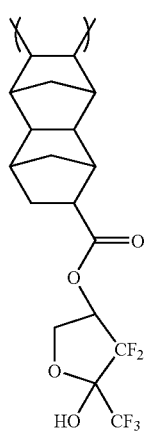
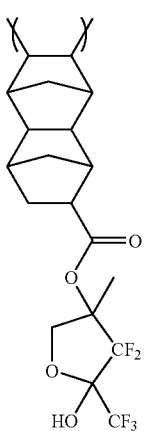
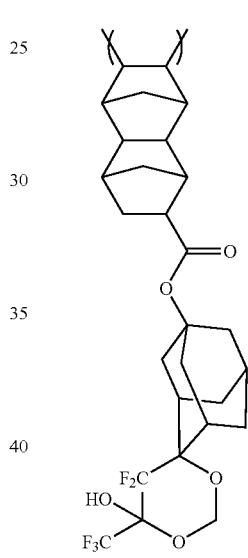
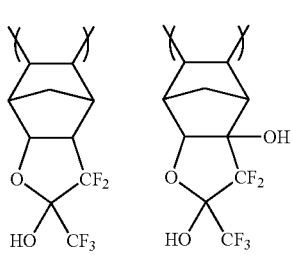
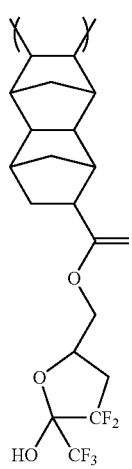
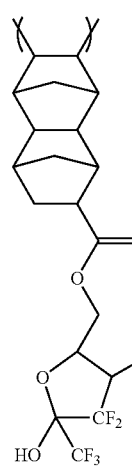
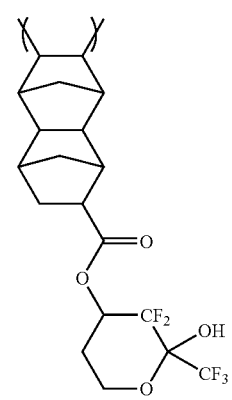
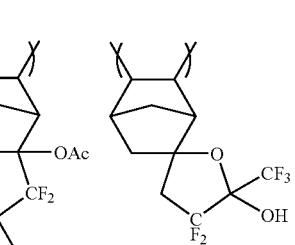
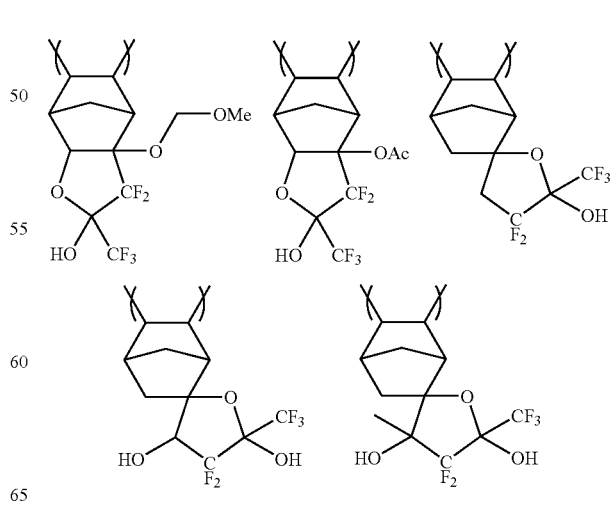
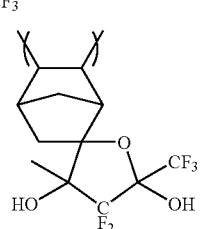

-continued
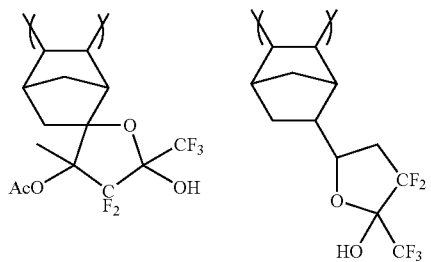
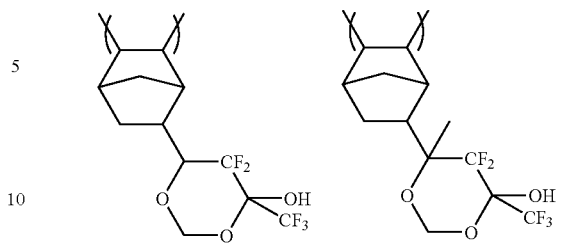
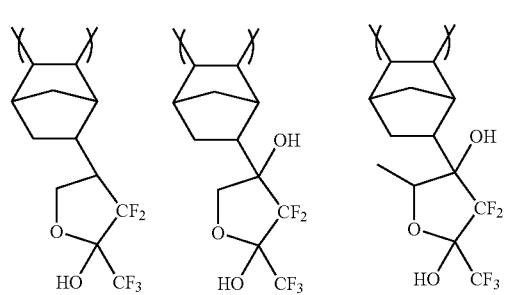
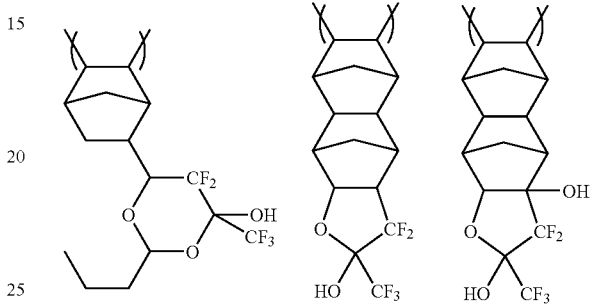
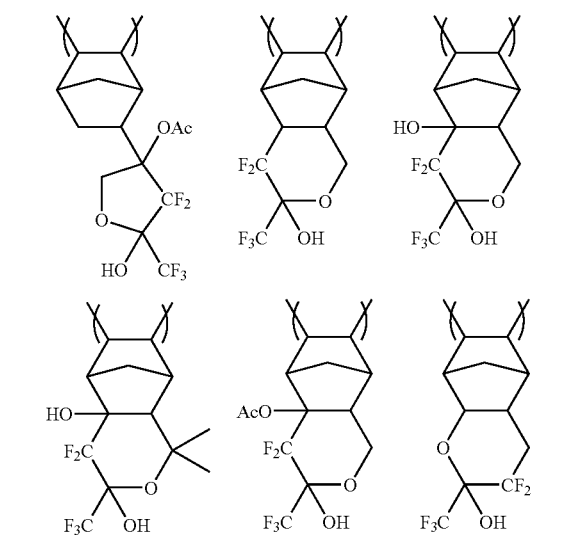
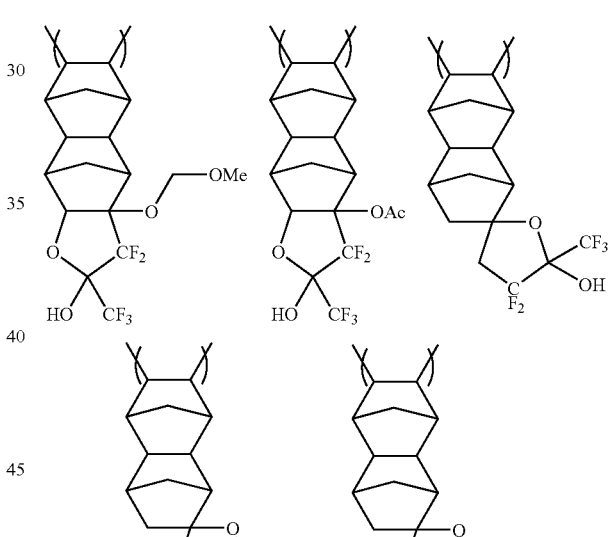
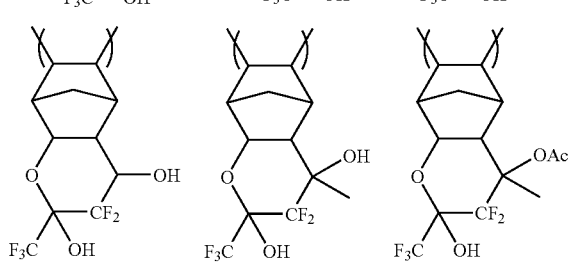
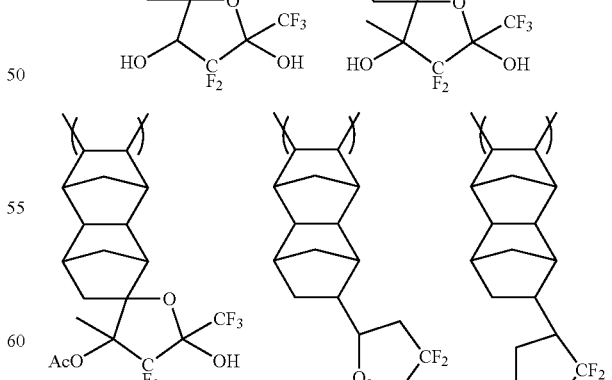
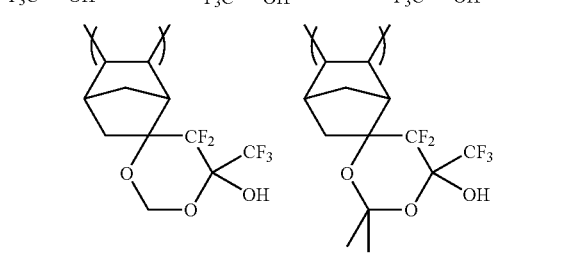
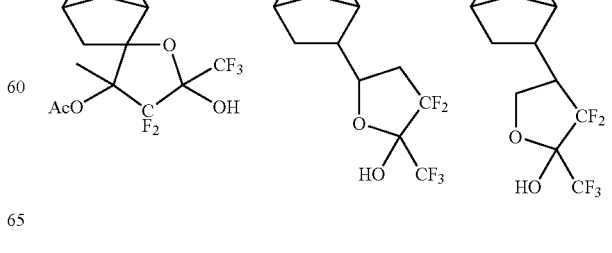

-continued
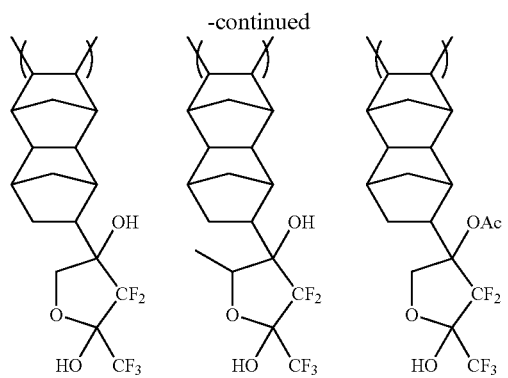
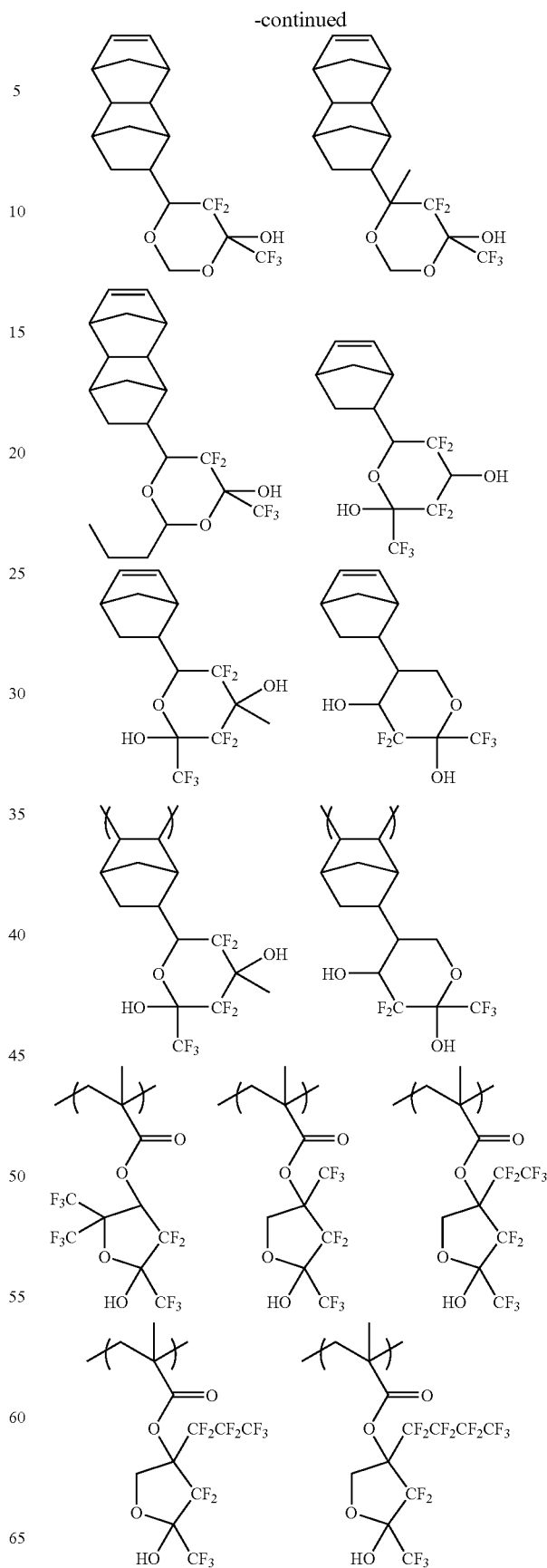

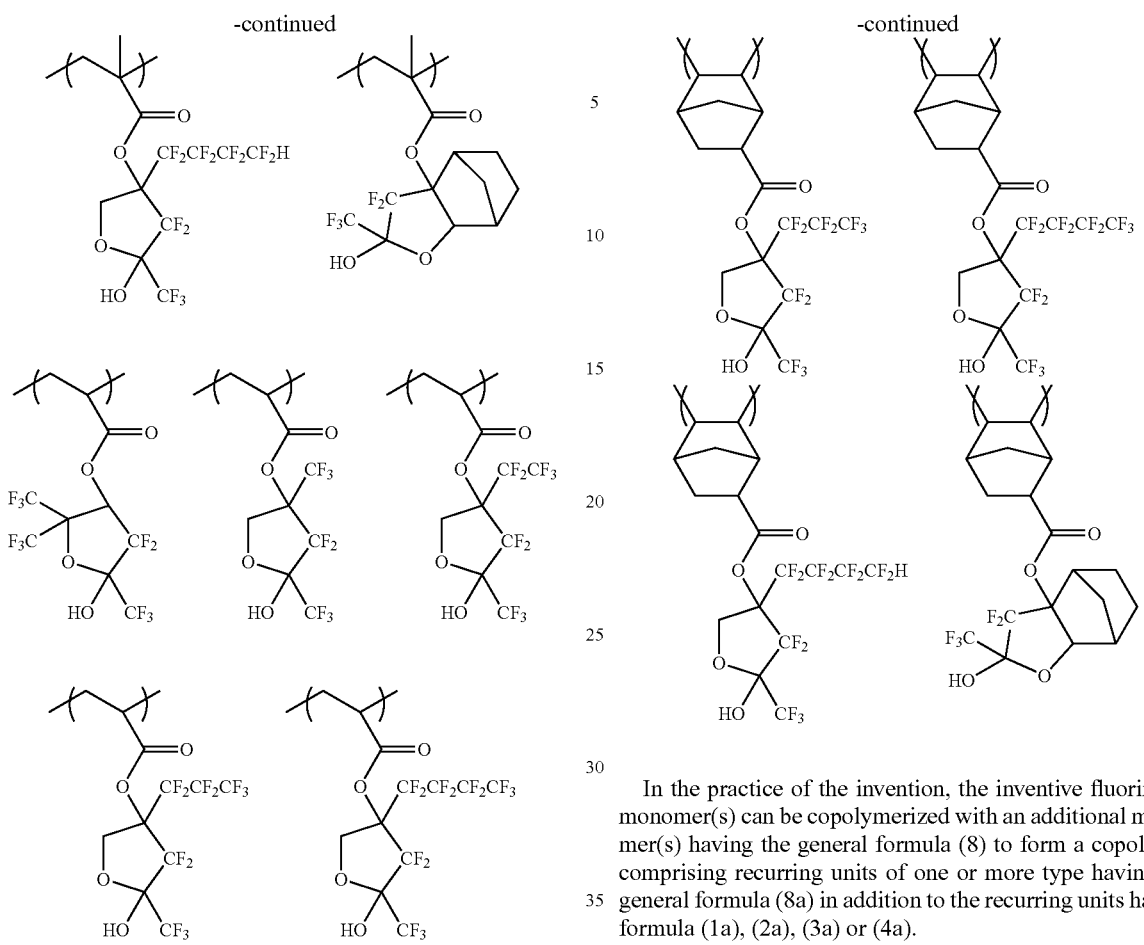

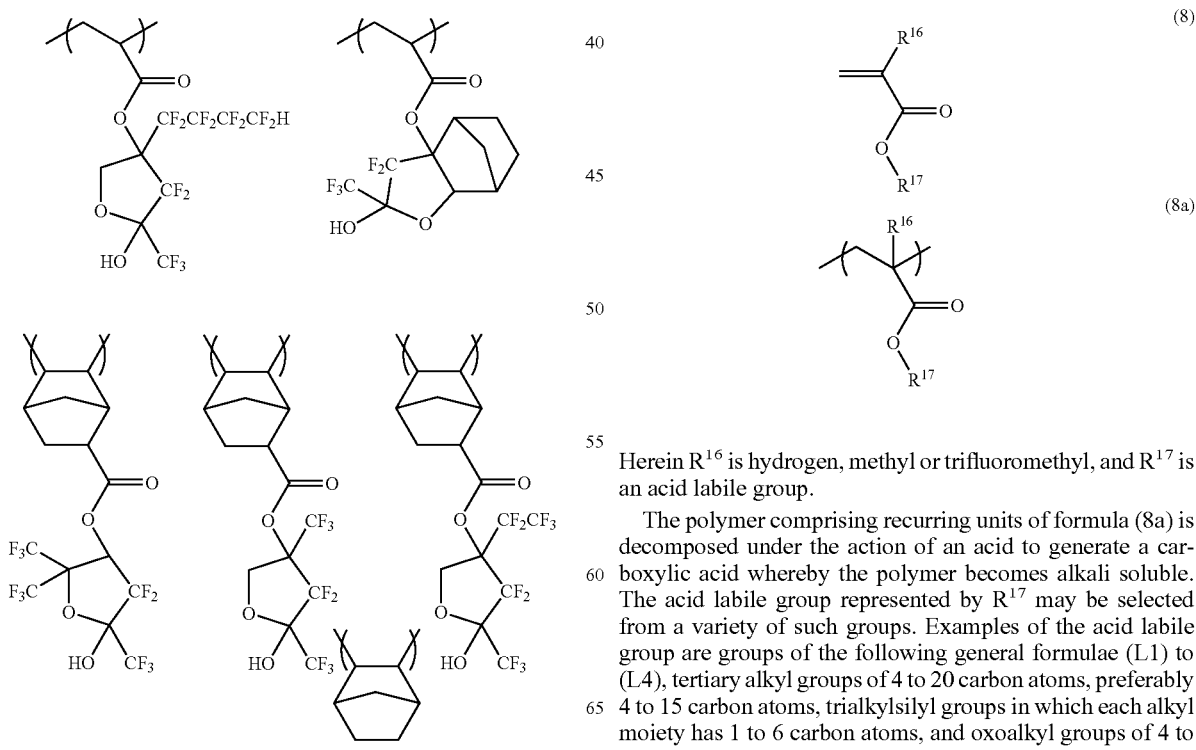

In the practice of the invention, the inventive fluorinated monomer(s) can be copolymerized with an additional monomer(s) having the general formula (8) to form a copolymer comprising recurring units of one or more type having the general formula (8a) in addition to the recurring units having formula (1a), (2a), (3a) or (4a).

Herein $R^{16}$ is hydrogen, methyl or trifluoromethyl, and $R^{17}$ is an acid labile group.

The polymer comprising recurring units of formula (8a) is decomposed under the action of an acid to generate a carboxylic acid whereby the polymer becomes alkali soluble. The acid labile group represented by $R^{17}$ may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

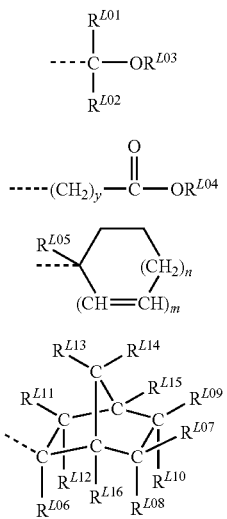

(L1)

(L2)

(L3)

(L4)

In these formulae and throughout the specification, the broken line denotes a valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, n-propyl, isopropyl, n-butyl, sec-butyl, tert-butyl, cyclopentyl, cyclohexyl, 2-ethylhexyl, and n-octyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like. Illustrative examples are the substituted alkyl groups shown below.

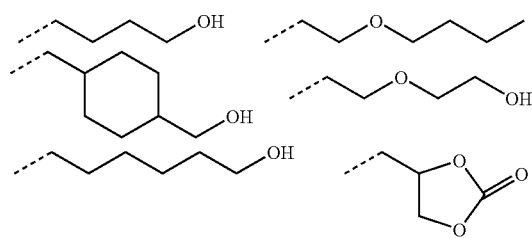

A pair of $R^{L01}$ and $R^{L02}$, $R^{L01}$ and $R^{L03}$, or $R^{L02}$ and $R^{L03}$ may form a ring with carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

In formula (L3), $R^{L05}$ is a monovalent hydrocarbon group of 1 to 8 carbon atoms or a substituted or unsubstituted aryl group of 6 to 20 carbon atoms. Examples of the monovalent hydrocarbon group include straight, branched or cyclic alkyl groups such as methyl, ethyl, n-propyl, isopropyl, n-butyl, sec-butyl, tert-butyl, tert-amyl, n-pentyl, n-hexyl, cyclopentyl, and cyclohexyl, and substituted forms of such groups in which some hydrogen atoms are substituted with hydroxyl, alkoxy, carboxy, alkoxycarbonyl, oxo, amino, alkylamino, cyano, mercapto, alkylthio, sulfo or other groups. Exemplary aryl groups are phenyl, methylphenyl, naphthyl, anthryl, phenanthryl, and pyrenyl. Letter m is equal to 0 or 1, n is equal to 0, 1, 2 or 3, and 2m+n is equal to 2 or 3.

In formula (L4), $R^{L06}$ is a monovalent hydrocarbon group of 1 to 8 carbon atoms or a substituted or unsubstituted aryl group of 6 to 20 carbon atoms. Examples of these groups are the same as exemplified for $R^{L05}$. $R^{L07}$ to $R^{L16}$ independently represent hydrogen or monovalent hydrocarbon groups of 1 to 15 carbon atoms. Exemplary hydrocarbon groups are straight, branched or cyclic alkyl groups such as methyl, ethyl, n-propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, $R^{L07}$ to $R^{L16}$, taken together, form a ring (for example, a pair of $R^{L07}$ and $R^{L08}$, $R^{L07}$ and $R^{L09}$, $R^{L08}$ and $R^{L10}$ $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to adjoining carbon atoms (for example, a pair of $R^{L07}$ and $R^{L09}$, $R^{L09}$ and $R^{L15}$, $R^{L13}$ and $R^{L15}$, or a similar pair) may bond together directly to form a double bond.

Of the acid labile groups of formula (L1), the straight and branched ones are exemplified by the following groups.

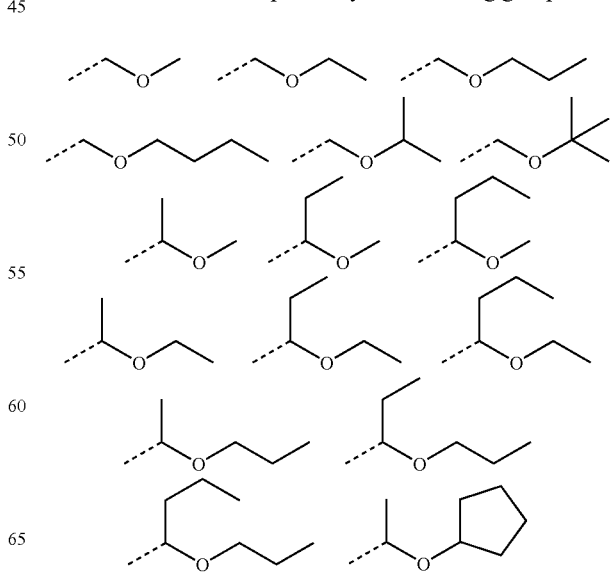

-continued

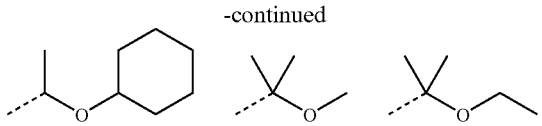

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Examples of the tertiary alkyl groups of 4 to 20 carbon atoms, trialkylsilyl groups in which each alkyl moiety has 1 to 6 carbon atoms, and oxoalkyl groups of 4 to 20 carbon atoms are as exemplified for $R^{L04}$.

In a further embodiment, an additional monomer(s) having the general formula (20) can be copolymerized with the inventive monomer(s) to form a copolymer further comprising recurring units of one or more type having the general formula (20a).

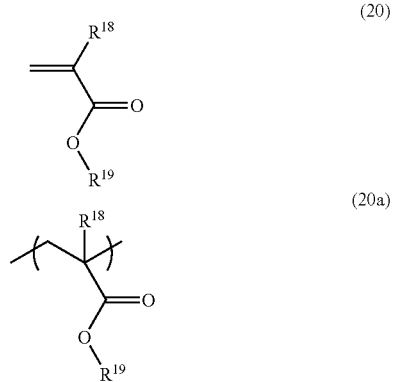

Herein $R^{18}$ is hydrogen, methyl or trifluoromethyl, and $R^{19}$ is an organic group of 2 to 20 carbon atoms containing one or more hydroxyl, carbonyl, ester (—COO—), ether (—O—) or cyano groups.

Examples of the organic group represented by $R^{19}$ include 2-hydroxyethyl, 2-cyanoethyl, 3-hydroxy-1-adamantyl, 3,5-dihydroxy-1-adamantyl, hydroxynorbornan-2-yl, 3-cyano-1-adamantyl, cyanonorbornan-2-yl, 2-oxo-3-tetrahydrofuranyl, 2-oxo-4-tetrahydrofuranyl, 4-oxα-5-oxotricyclo[5.2.1.0$^{2,6}$]decyl, 2,6-norbornanecarbolacton-3-ylmethyl, 2,6-norbornanecarbolacton-5-yl, 3-methoxycarbonyl-2,6-norbornanecarbolacton-5-yl, 7-oxa-2,6-norbornanecarbolacton-5-yl, 7-oxa-2,3-norbornanecarbolacton-5-yl, 7-oxa-2,3-norbornanecarbolacton-6-yl, spiro[norbornane-2,4'-(2-oxotetrahydrofuran)]-5-yl, spiro[norbornane-2,4'-(2-oxotetrahydrofuran)]-6-yl. By adjusting the type and amount of recurring units having formula (20a), the hydrophilic/hydrophobic balance of the polymer can be optimized.

In addition to the recurring units having formulae (1a), (2a), (3a), (4a), (5a), (8a) and (20a), the inventive polymer may further comprise recurring units "Q" derived from various monomers having a polymerizable carbon-to-carbon double bond for improving the resist performance.

Suitable such monomers include α,β-unsaturated carboxylic acids and esters thereof, α,β-unsaturated nitriles, α,β-unsaturated lactones, unsaturated carboxylic anhydrides, maleimides, norbornene derivatives, tetracyclo[4.4.0.1$^{2,5}$.1$^{7,10}$]dodecene derivatives, allyl ethers, vinyl ethers, vinyl esters, vinyl silanes, and vinyl siloxanes.

More particularly, suitable α,β-unsaturated carboxylic acids include (meth)acrylic acid, α-trifluoromethylacrylic acid, etc.; suitable α,β-unsaturated carboxylic esters include alkyl esters of α,β-unsaturated carboxylic acids such as (meth)acrylic acid, crotonic acid, maleic acid, α-trifluoromethylacrylic acid, etc. (wherein exemplary alkyl groups are straight, branched or cyclic $C_1$-$C_{20}$ alkyl groups); a typical α,β-unsaturated nitrile is acrylonitrile; suitable α,β-unsaturated lactones include 5,6-dihydro-2H-pyran-2-one and 2(5H)-furanone; suitable unsaturated carboxylic anhydrides include maleic anhydride and itaconic anhydride; suitable maleimides include maleimide and N-substituted maleimides; suitable norbornene derivatives include norbornene, 5-norbornene-2-carboxylic acid and ester derivatives thereof; suitable tetracyclo[4.4.0.1$^{2,5}$.1$^{7,10}$]dodecene derivatives include tetracyclo[4.4.0.1$^{2,5}$.1$^{7,10}$]dodec-8-ene-3-carboxylic acid and ester derivatives thereof, 3-methyltetracyclo[4.4.0.1$^{2,5}$.1$^{7,10}$]dodec-8-ene-3-carboxylic acid and ester derivatives thereof; a typical allyl ether is 2,5-dihydrofuran; suitable vinyl ethers include 2,3-dihydrofuran and 3,4-dihydro-2H-pyran; a typical vinyl ester is vinyl acetate; and suitable vinylsilanes and vinylsiloxanes include vinyltrimethylsilane, vinylpentamethylcyclotrisiloxane, vinylheptamethylcyclotetrasiloxane, vinylpentamethyldisiloxane, and bis(trimethylsilylmethyl)vinylmethylsilane.

In the polymer, the total of recurring units having formula (1a), (2a), (3a) or (4a) accounts for preferably 1 to 80 mol %, more preferably 3 to 50 mol % of the polymer, recurring units having formula (8a) account for preferably 1 to 80 mol %, more preferably 3 to 70 mol % of the polymer, and recurring units having formula (20a) account for preferably 0 to 70 mol %, more preferably 0 to 50 mol % of the polymer. Also, recurring units Q may be present in an amount of preferably 0 to 50 mol %, more preferably 0 to 40 mol % of the polymer.

The polymer of the invention should preferably have a weight average molecular weight (Mw) of about 2,000 to about 100,000 as determined by gel permeation chromatography (GPC) versus polystyrene standards. With a Mw of less than 2,000, film formation and resolution may be poor whereas a Mw of more than 100,000 can compromise resolution.

The polymers derived from the fluorinated monomers of the invention are fully transparent to radiation having a wavelength of up to 500 nm, especially up to 200 nm, exhibit improved development performance due to the inclusion of phenol-like acidic hydroxyl groups, and thus find best use as the base resin in radiation-sensitive resist compositions. Examples of the radiation having a wavelength of up to 300 nm include ArF laser (193 nm), $F_2$ laser (157 nm), $Ar_2$ laser (126 nm), and extreme ultraviolet (EUV, 13 nm). The exposure system may be either conventional dry exposure or immersion exposure. In the immersion lithography, the liquid fill between the wafer and the projection lens should have a higher refractive index and high transparency, with water having a refractive index of 1.44 at wavelength 193 nm being often used. For better resolution, liquids having a refractive index of 1.6 or higher such as phosphoric acid, ethylene glycol and trialkoxyaluminum may also be used.

Resist Composition

The present invention in the third aspect provides a photoresist composition comprising (A) the above-described polymer as a base resin, (B) a photoacid generator, (C) an organic solvent, and optionally (D) a nitrogen-containing organic compound.

Component B

The photoacid generator (B) may be any compound capable of generating an acid upon exposure to high energy radiation having a wavelength of up to 300 nm or electron beams as long as a resist composition comprising the photoacid generator, the inventive polymer and an organic solvent can be a homogeneous solution which is effectively applicable to form a uniform film.

Examples of the photoacid generator which can be used herein include:
(i) onium salts of the formula (P1a-1), (P1a-2) or (P1b),
(ii) diazomethane derivatives of the formula (P2),
(iii) glyoxime derivatives of the formula (P3),
(iv) bissulfone derivatives of the formula (P4),
(v) sulfonic acid esters of N-hydroxyimide compounds of the formula (P5),
(vi) β-ketosulfonic acid derivatives,
(vii) disulfone derivatives,
(viii) nitrobenzylsulfonate derivatives,
(ix) sulfonate derivatives, and
(x) oxime sulfonates.

These photoacid generators are described in detail.

(i) Onium Salts of Formula (P1a-1), (P1a-2) or (P1b):

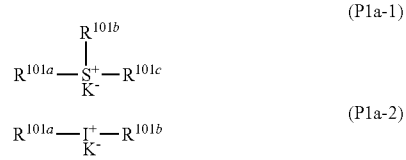

Herein, $R^{101a}$, $R^{101b}$, and $R^{101c}$ independently represent straight, branched or cyclic alkyl, alkenyl or oxoalkyl groups of 1 to 12 carbon atoms, aryl groups of 6 to 20 carbon atoms, or aralkyl or aryloxyalkyl groups of 7 to 12 carbon atoms, wherein some or all of the hydrogen atoms may be replaced by alkoxy or other groups. Also, $R^{101b}$ and $R^{101c}$, taken together, may form a ring. $R^{101b}$ and $R^{101c}$ each are alkylene groups of 1 to 6 carbon atoms when they form a ring. $K^-$ is a non-nucleophilic counter ion.

$R^{101a}$, $R^{101b}$, and $R^{101c}$ may be the same or different and are illustrated below. Exemplary alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Exemplary alkenyl groups include vinyl, allyl, propenyl, butenyl, hexenyl, and cyclohexenyl. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary aralkyl groups include benzyl, phenylethyl, and phenethyl. Exemplary aryloxyalkyl groups are 2-aryl-2-oxoethyl groups such as 2-phenyl-2-oxoethyl, 2-(1-naphthyl)-2-oxoethyl, and 2-(2-naphthyl)-2-oxoethyl. Examples of the non-nucleophilic counter ion represented by $K^-$ include halide ions such as chloride and bromide ions, fluoroalkylsulfonate ions such as triflate, 1,1,1-trifluoroethanesulfonate, and nonafluorobutanesulfonate, arylsulfonate ions such as tosylate, benzenesulfonate, 4-fluorobenzenesulfonate, and 1,2,3,4,5-pentafluorobenzenesulfonate, and alkylsulfonate ions such as mesylate and butanesulfonate.

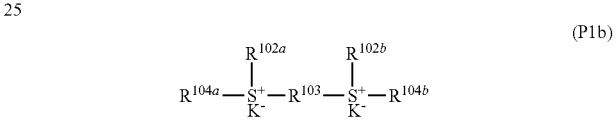

Herein, $R^{102a}$ and $R^{102b}$ independently represent straight, branched or cyclic alkyl groups of 1 to 8 carbon atoms. $R^{103}$ represents a straight, branched or cyclic alkylene group of 1 to 10 carbon atoms. $R^{104a}$ and $R^{104b}$ independently represent 2-oxoalkyl groups of 3 to 7 carbon atoms. $K^-$ is a non-nucleophilic counter ion.

Illustrative of the groups represented by $R^{102a}$ and $R^{102b}$ are methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl, and cyclohexylmethyl. Illustrative of the groups represented by $R^{103}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene. Illustrative of the groups represented by $R^{104a}$ and $R^{104b}$ are 2-oxopropyl, 2-oxocyclopentyl, 2-oxocyclohexyl, and 2-oxocycloheptyl. Illustrative examples of the counter ion represented by $K^-$ are the same as exemplified for formulae (P1a-1) and (P1a-2).

(ii) Diazomethane Derivatives of Formula (P2)

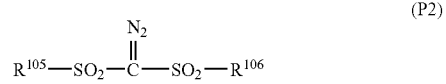

Herein, $R^{105}$ and $R^{106}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms.

Of the groups represented by $R^{105}$ and $R^{106}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime Derivatives of Formula (P3)

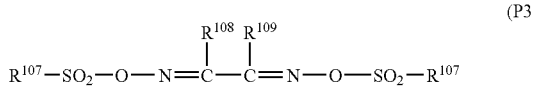

(P3)

Herein, $R^{107}$, $R^{108}$, and $R^{109}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms. Also, $R^{108}$ and $R^{109}$, taken together, may form a ring. $R^{108}$ and $R^{109}$ each are straight or branched alkylene groups of 1 to 6 carbon atoms when they form a ring.

Illustrative examples of the alkyl, halogenated alkyl, aryl, halogenated aryl, and aralkyl groups represented by $R^{107}$, $R^{108}$, and $R^{109}$ are the same as exemplified for $R^{105}$ and $R^{106}$. Examples of the alkylene groups represented by $R^{108}$ and $R^{109}$ include methylene, ethylene, propylene, butylene, and hexylene.

(iv) Bissulfone Derivatives of Formula (P4)

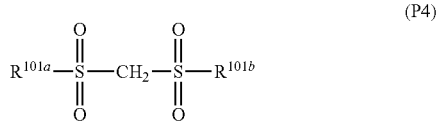

(P4)

Herein, $R^{101a}$ and $R^{101b}$ are as defined above.

(v) Sulfonic Acid Esters of N-hydroxyimide Compounds of Formula (P5)

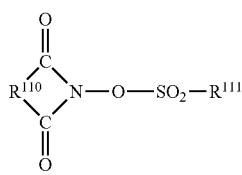

(P5)

Herein, $R^{101}$ is an arylene group of 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups. $R^{111}$ is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), heteroaromatic groups of 3 to 5 carbon atoms, or chlorine or fluorine atoms.

Of the groups represented by $R^{110}$, exemplary arylene groups include 1,2-phenylene and 1,8-naphthylene; exemplary alkylene groups include methylene, ethylene, trimethylene, tetramethylene, phenylethylene, and norbornane-2,3-diyl; and exemplary alkenylene groups include 1,2-vinylene, 1-phenyl-1,2-vinylene, and 5-norbornene-2,3-diyl. Of the groups represented by $R^{111}$, exemplary alkyl groups are as exemplified for $R^{101a}$ to $R^{101c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, propyl, isopropyl, n-butyl, isobutyl and tert-butyl; and the alkoxy groups of 1 to 4 carbon atoms include methoxy, ethoxy, propoxy, isopropoxy, n-butoxy, isobutoxy, and tert-butoxy. The phenyl groups which may have substituted thereon an alkyl or alkoxy of 1 to 4 carbon atoms, nitro, or acetyl group include phenyl, tolyl, p-tert-butoxyphenyl, p-acetylphenyl and p-nitrophenyl. The hetero-aromatic groups of 3 to 5 carbon atoms include pyridyl and furyl.

Illustrative examples of the photoacid generator include:
onium salts such as
diphenyliodonium trifluoromethanesulfonate,
(p-tert-butoxyphenyl)phenyliodonium trifluoromethanesulfonate,
diphenyliodonium p-toluenesulfonate,
(p-tert-butoxyphenyl)phenyliodonium p-toluenesulfonate,
triphenylsulfonium trifluoromethanesulfonate,
(p-tert-butoxyphenyl)diphenylsulfonium trifluoromethanesulfonate,
bis(p-tert-butoxyphenyl)phenylsulfonium trifluoromethanesulfonate,
tris(p-tert-butoxyphenyl)sulfonium trifluoromethanesulfonate,
triphenylsulfonium p-toluenesulfonate,
(p-tert-butoxyphenyl)diphenylsulfonium p-toluenesulfonate,
bis(p-tert-butoxyphenyl)phenylsulfonium p-toluenesulfonate,
tris(p-tert-butoxyphenyl)sulfonium p-toluenesulfonate,
triphenylsulfonium nonafluorobutanesulfonate,
triphenylsulfonium butanesulfonate,
trimethylsulfonium trifluoromethanesulfonate,
trimethylsulfonium p-toluenesulfonate,
cyclohexylmethyl(2-oxocyclohexyl)sulfonium trifluoromethanesulfonate,
cyclohexylmethyl(2-oxocyclohexyl)sulfonium p-toluenesulfonate,
dimethylphenylsulfonium trifluoromethanesulfonate,
dimethylphenylsulfonium p-toluenesulfonate,
dicyclohexylphenylsulfonium trifluoromethanesulfonate,
dicyclohexylphenylsulfonium p-toluenesulfonate,
trinaphthylsulfonium trifluoromethanesulfonate,
cyclohexylmethyl(2-oxocyclohexyl)sulfonium trifluoromethanesulfonate, (2-norbornyl)methyl(2-oxocyclohexyl)sulfonium trifluoromethanesulfonate,
ethylenebis[methyl(2-oxocyclopentyl)sulfonium trifluoromethanesulfonate], and
1,2'-naphthylcarbonylmethyltetrahydrothiophenium triflate; diazomethane derivatives such as
bis(benzenesulfonyl)diazomethane,
bis(p-toluenesulfonyl)diazomethane,
bis(xylenesulfonyl)diazomethane,
bis(cyclohexylsulfonyl)diazomethane,
bis(cyclopentylsulfonyl)diazomethane,
bis(n-butylsulfonyl)diazomethane,
bis(isobutylsulfonyl)diazomethane,
bis(sec-butylsulfonyl)diazomethane,
bis(n-propylsulfonyl)diazomethane,
bis(isopropylsulfonyl)diazomethane,
bis(tert-butylsulfonyl)diazomethane,
bis(n-amylsulfonyl)diazomethane,
bis(isoamylsulfonyl)diazomethane,
bis(sec-amylsulfonyl)diazomethane,
bis(tert-amylsulfonyl)diazomethane,
1-cyclohexylsulfonyl-1-(tert-butylsulfonyl)diazomethane,
1-cyclohexylsulfonyl-1-(tert-amylsulfonyl)diazomethane, and
1-tert-amylsulfonyl-1-(tert-butylsulfonyl)diazomethane; glyoxime derivatives such as
bis-O-(p-toluenesulfonyl)-α-dimethylglyoxime,
bis-O-(p-toluenesulfonyl)-α-diphenylglyoxime,
bis-O-(p-toluenesulfonyl)-α-dicyclohexylglyoxime,
bis-o-(p-toluenesulfonyl)-2,3-pentanedioneglyoxime,
bis-O-(p-toluenesulfonyl)-2-methyl-3,4-pentanedioneglyoxime,
bis-O-(n-butanesulfonyl)-α-dimethylglyoxime,
bis-O-(n-butanesulfonyl)-α-diphenylglyoxime,
bis-O-(n-butanesulfonyl)-α-dicyclohexylglyoxime,
bis-O-(n-butanesulfonyl)-2,3-pentanedioneglyoxime,
bis-O-(n-butanesulfonyl)-2-methyl-3,4-pentanedioneglyoxime,
bis-O-(methanesulfonyl)-α-dimethylglyoxime,
bis-O-(trifluoromethanesulfonyl)-α-dimethylglyoxime,
bis-O-(1,1,1-trifluoroethanesulfonyl)-α-dimethylglyoxime,
bis-O-(tert-butanesulfonyl)-α-dimethylglyoxime,
bis-O-(perfluorooctanesulfonyl)-α-dimethylglyoxime,
bis-O-(cyclohexanesulfonyl)-α-dimethylglyoxime,
bis-O-(benzenesulfonyl)-α-dimethylglyoxime,
bis-O-(p-fluorobenzenesulfonyl)-α-dimethylglyoxime,
bis-O-(p-tert-butylbenzenesulfonyl)-α-dimethylglyoxime,
bis-O-(xylenesulfonyl)-α-dimethylglyoxime, and
bis-O-(camphorsulfonyl)-α-dimethylglyoxime;
bissulfone derivatives such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane;
β-ketosulfone derivatives such as
2-cyclohexylcarbonyl-2-(p-toluenesulfonyl)propane and
2-isopropylcarbonyl-2-(p-toluenesulfonyl)propane;
nitrobenzyl sulfonate derivatives such as
2,6-dinitrobenzyl p-toluenesulfonate and
2,4-dinitrobenzyl p-toluenesulfonate;
sulfonic acid ester derivatives such as
1,2,3-tris(methanesulfonyloxy)benzene,
1,2,3-tris(trifluoromethanesulfonyloxy)benzene, and
1,2,3-tris(p-toluenesulfonyloxy)benzene; and
sulfonic acid esters of N-hydroxyimides such as
N-hydroxysuccinimide methanesulfonate,
N-hydroxysuccinimide trifluoromethanesulfonate,
N-hydroxysuccinimide ethanesulfonate,
N-hydroxysuccinimide 1-propanesulfonate,
N-hydroxysuccinimide 2-propanesulfonate,
N-hydroxysuccinimide 1-pentanesulfonate,
N-hydroxysuccinimide 1-octanesulfonate,
N-hydroxysuccinimide p-toluenesulfonate,
N-hydroxysuccinimide p-methoxybenzenesulfonate,
N-hydroxysuccinimide 2-chloroethanesulfonate,
N-hydroxysuccinimide benzenesulfonate,
N-hydroxysuccinimide 2,4,6-trimethylbenzenesulfonate,
N-hydroxysuccinimide 1-naphthalenesulfonate,
N-hydroxysuccinimide 2-naphthalenesulfonate,
N-hydroxy-2-phenylsuccinimide methanesulfonate,
N-hydroxymaleimide methanesulfonate,
N-hydroxymaleimide ethanesulfonate,
N-hydroxy-2-phenylmaleimide methanesulfonate,
N-hydroxyglutarimide methanesulfonate,
N-hydroxyglutarimide benzenesulfonate,
N-hydroxyphthalimide methanesulfonate,
N-hydroxyphthalimide benzenesulfonate,
N-hydroxyphthalimide trifluoromethanesulfonate,
N-hydroxyphthalimide p-toluenesulfonate,
N-hydroxynaphthalimide methanesulfonate,
N-hydroxynaphthalimide benzenesulfonate,
N-hydroxy-5-norbornene-2,3-dicarboxyimide methanesulfonate,
N-hydroxy-5-norbornene-2,3-dicarboxyimide trifluoromethanesulfonate, and
N-hydroxy-5-norbornene-2,3-dicarboxyimide p-toluenesulfonate.

Preferred among these photoacid generators are onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocylohexyl)sulfonium trifluoromethanesulfonate, and 1,2'-naphthylcarbonylmethyltetrahydrothiophenium triflate; diazomethane derivatives such as
bis(benzenesulfonyl)diazomethane,
bis(p-toluenesulfonyl)diazomethane,
bis(cyclohexylsulfonyl)diazomethane,
bis(n-butylsulfonyl)diazomethane,
bis(isobutylsulfonyl)diazomethane,
bis(sec-butylsulfonyl)diazomethane,
bis(n-propylsulfonyl)diazomethane,
bis(isopropylsulfonyl)diazomethane, and
bis(tert-butylsulfonyl)diazomethane;
glyoxime derivatives such as
bis-O-(p-toluenesulfonyl)-α-dimethylglyoxime and
bis-O-(n-butanesulfonyl)-α-dimethylglyoxime;
bissulfone derivatives such as bisnaphthylsulfonylmethane; and sulfonic acid esters of N-hydroxyimide compounds such as
N-hydroxysuccinimide methanesulfonate,
N-hydroxysuccinimide trifluoromethanesulfonate,
N-hydroxysuccinimide 1-propanesulfonate,
N-hydroxysuccinimide 2-propanesulfonate,
N-hydroxysuccinimide 1-pentanesulfonate,
N-hydroxysuccinimide p-toluenesulfonate,
N-hydroxynaphthalimide methanesulfonate, and
N-hydroxynaphthalimide benzenesulfonate.

Also included are the oxime sulfonates described in U.S. Pat. No. 6,004,724, for example,
(5-(4-toluenesulfonyl)oxyimino-5H-thiophen-2-ylidene)phenyl-acetonitrile,
(5-(10-camphorsulfonyl)oxyimino-5H-thiophen-2-ylidene)phenyl-acetonitrile,
(5-n-octanesulfonyloxyimino-5H-thiophen-2-ylidene)phenyl-acetonitrile,
(5-(4-toluenesulfonyl)oxyimino-5H-thiophen-2-ylidene)(2-methylphenyl)acetonitrile,
(5-(10-camphorsulfonyl)oxyimino-5H-thiophen-2-ylidene)(2-methylphenyl)acetonitrile,
(5-n-octanesulfonyloxyimino-5H-thiophen-2-ylidene)(2-methylphenyl)acetonitrile, etc.

Also included are the oxime sulfonates described in U.S. Pat. No. 6,261,738 and JP-A 2000-314956, for example, 2,2,2-trifluoro-1-phenyl-ethanone oxime-O-methylsulfonate; 2,2,2-trifluoro-1-phenyl-ethanone oxime-O-(10-camphorylsulfonate); 2,2,2-trifluoro-1-phenyl-ethanone oxime-O-(4-methoxyphenylsulfonate); 2,2,2-trifluoro-1-phenyl-ethanone oxime-O-(1-naphthylsulfonate); 2,2,2-trifluoro-1-phenylethanone oxime-O-(2-naphthylsulfonate); 2,2,2-trifluoro-1-phenyl-ethanone oxime-O-(2,4,6-trimethylphenylsulfonate); 2,2,2-trifluoro-1-(4-methylphenyl)-ethanone oxime-O-(10-camphorylsulfonate); 2,2,2-trifluoro-1-(4-methylphenyl)-ethanone oxime-O-(methylsulfonate); 2,2,2-trifluoro-1-(2-methylphenyl)-ethanone oxime-O-(10-camphorylsulfonate); 2,2,2-trifluoro-1-(2,4-dimethylphenyl)-ethanone oxime-O-(10-camphorylsulfonate); 2,2,2-trifluoro-1-(2,4-dimethylphenyl)-ethanone oxime-O-(1-naphthylsulfonate); 2,2,2-trifluoro-1-(2,4-dimethylphenyl)-ethanone oxime-O-(2-naphthylsulfonate); 2,2,2-trifluoro-1-(2,4,6-trimethylphenyl)-ethanone oxime-O-(10-camphorylsulfonate); 2,2,2-trifluoro-1-(2,4,6-trimethylphenyl)-ethanone oxime-O-(1-naphthylsulfonate); 2,2,2-trifluoro-1-(2,4,6-trimethylphenyl)-ethanone oxime-O-(2-naphthylsulfonate); 2,2,2-trifluoro-1-(4-methoxyphenyl)-ethanone oxime-O-methylsulfonate; 2,2,2-trifluoro-1-(4-methylthiophenyl)-ethanone oxime-O-methylsulfonate; 2,2,2-trifluoro-1-(3,4-dimethoxyphenyl)-ethanone oxime-O-methylsulfonate; 2,2,3,3,4,4,4-heptafluoro-1-phenyl-butanone oxime-O-(10-camphorylsulfonate); 2,2,2-trifluoro-1-(phenyl)-ethanone oxime-O-methylsulfonate; 2,2,2-trifluoro-1-(phenyl)-ethanone oxime-O-10-camphorylsulfonate; 2,2,2-trifluoro-1-(phenyl)-ethanone oxime-O-(4-methoxyphenyl)sulfonate; 2,2,2-trifluoro-1-(phenyl)-ethanone oxime-O-(1-naphthyl)sulfonate; 2,2,2-trifluoro-1-(phenyl)-ethanone oxime-O-(2-naphthyl)sulfonate; 2,2,2-trifluoro-1-(phenyl)-ethanone oxime-O-(2,4,6-trimethylphenyl)sulfonate; 2,2,2-trifluoro-1-(4-methylphenyl)-ethanone oxime-O-(10-camphoryl)sulfonate; 2,2,2-trifluoro-1-(4-methylphenyl)-ethanone oxime-O-methylsulfonate; 2,2,2-trifluoro-1-(2-methylphenyl)-ethanone oxime-O-(10-camphoryl)sulfonate; 2,2,2-trifluoro-1-(2,4-dimethylphenyl)-ethanone oxime-O-(1-naphthyl)sulfonate; 2,2,2-trifluoro-1-(2,4-dimethylphenyl)-ethanone oxime-O-(2-naphthyl)sulfonate; 2,2,2-trifluoro-1-(2,4,6-trimethylphenyl)-ethanone oxime-O-(10-camphoryl)sulfonate; 2,2,2-trifluoro-1-(2,4,6-trimethylphenyl)-ethanone oxime-O-(1-naphthyl)sulfonate; 2,2,2-trifluoro-1-(2,4,6-trimethylphenyl)-ethanone oxime-O-(2-naphthyl)sulfonate; 2,2,2-trifluoro-1-(4-methoxyphenyl)-ethanone oxime-O-methylsulfonate; 2,2,2-trifluoro-1-(4-thiomethylphenyl)-ethanone oxime-O-methylsulfonate; 2,2,2-trifluoro-1-(3,4-dimethoxyphenyl)-ethanone oxime-O-methylsulfonate; 2,2,2-trifluoro-1-(4-methoxyphenyl)-ethanone oxime-O-(4-methylphenyl)sulfonate; 2,2,2-trifluoro-1-(4-methoxyphenyl)-ethanone oxime-O-(4-methoxyphenyl)sulfonate; 2,2,2-trifluoro-1-(4-methoxyphenyl)-ethanone oxime-O-(4-dodecylphenyl)-sulfonate; 2,2,2-trifluoro-1-(4-methoxyphenyl)-ethanone oxime-O-octylsulfonate; 2,2,2-trifluoro-1-(4-thiomethyl-phenyl)-ethanone oxime-O-(4-methoxyphenyl)sulfonate; 2,2,2-trifluoro-1-(4-thiomethylphenyl)-ethanone oxime-O-(4-dodecylphenyl)sulfonate; 2,2,2-trifluoro-1-(4-thiomethyl-phenyl)-ethanone oxime-O-octylsulfonate; 2,2,2-trifluoro-1-(4-thiomethylphenyl)-ethanone oxime-O-(2-naphthyl)sulfonate; 2,2,2-trifluoro-1-(2-methylphenyl)-ethanone oxime-O-methylsulfonate; 2,2,2-trifluoro-1-(4-methylphenyl)ethanone oxime-O-phenylsulfonate; 2,2,2-trifluoro-1-(4-chlorophenyl)-ethanone oxime-O-phenylsulfonate; 2,2,3,3,4,4,4-heptafluoro-1-(phenyl)-butanone oxime-O-(10-camphoryl)sulfonate; 2,2,2-trifluoro-1-naphthyl-ethanone oxime-O-methylsulfonate; 2,2,2-trifluoro-2-naphthyl-ethanone oxime-O-methylsulfonate; 2,2,2-trifluoro-1-[4-benzylphenyl]-ethanone oxime-O-methylsulfonate; 2,2,2-trifluoro-1-[4-(phenyl-1,4-dioxa-but-1-yl)phenyl]-ethanone oxime-O-methylsulfonate; 2,2,2-trifluoro-1-naphthyl-ethanone oxime-O-propylsulfonate; 2,2,2-trifluoro-2-naphthyl-ethanone oxime-0-propylsulfonate; 2,2,2-trifluoro-1-[4-benzylphenyl]-ethanone oxime-O-propyl-sulfonate; 2,2,2-trifluoro-1-[4-methylsulfonylphenyl]-ethanone oxime-O-propylsulfonate; 1,3-bis[1-(4-phenoxyphenyl)-2,2,2-trifluoroethanone oxime-O-sulfonyl]phenyl; 2,2,2-trifluoro-1-[4-methylsulfonyl-oxyphenyl]-ethanone oxime-O-propylsulfonate; 2,2,2-trifluoro-1-[4-methylcarbonyloxyphenyl]-ethanone oxime-O-propylsulfonate; 2,2,2-trifluoro-1-[6H,7H-5,8-dioxonaphth-2-yl]-ethanone oxime-O-propylsulfonate; 2,2,2-trifluoro-1-[4-methoxycarbonylmethoxyphenyl]-ethanone oxime-O-propylsulfonate; 2,2,2-trifluoro-1-[4-(methoxycarbonyl)-(4-amino-1-oxa-pent-1-yl)-phenyl]-ethanone oxime-O-propylsulfonate; 2,2,2-trifluoro-1-[3,5-dimethyl-4-ethoxyphenyl]-ethanone oxime-O-propylsulfonate; 2,2,2-trifluoro-1-[4-benzyloxyphenyl]-ethanone oxime-O-propylsulfonate; 2,2,2-trifluoro-1-[2-thiophenyl]-ethanone oxime-O-propylsulfonate; and 2,2,2-trifluoro-1-[1-dioxathiophen-2-yl)]-ethanone oxime-O-propylsulfonate.

Also included are the oxime sulfonates described in JP-A 9-95479 and JP-A 9-230588 and the references cited therein, for example,
α-(p-toluenesulfonyloxyimino)-phenylacetonitrile,
α-(p-chlorobenzenesulfonyloxyimino)-phenylacetonitrile,
α-(4-nitrobenzenesulfonyloxyimino)-phenylacetonitrile,
α-(4-nitro-2-trifluoromethylbenzenesulfonyloxyimino)-phenylacetonitrile,
α-(benzenesulfonyloxyimino)-4-chlorophenylacetonitrile,
α-(benzenesulfonyloxyimino)-2,4-dichlorophenylacetonitrile,
α-(benzenesulfonyloxyimino)-2,6-dichlorophenylacetonitrile,
α-(benzenesulfonyloxyimino)-4-methoxyphenylacetonitrile,
α-(2-chlorobenzenesulfonyloxyimino)-4-methoxyphenylacetonitrile,
α-(benzenesulfonyloxyimino)-2-thienylacetonitrile,
α-(4-dodecylbenzenesulfonyloxyimino)-phenylacetonitrile,
α-[(4-toluenesulfonyloxyimino)-4-methoxyphenyl]acetonitrile,
α-[(dodecylbenzenesulfonyloxyimino)-4-methoxyphenyl]acetonitrile,
α-(tosyloxyimino)-3-thienylacetonitrile,
α-(methylsulfonyloxyimino)-1-cyclopentenylacetonitrile, α-(ethylsulfonylbxyimino)-1-cyclopentenylacetonitrile,
α-(isopropylsulfonyloxyimino)-1-cyclopentenylacetonitrile,
α-(n-butylsulfonyloxyimino)-1-cyclopentenylacetonitrile,
α-(ethylsulfonyloxyimino)-1-cyclohexenylacetonitrile,
α-(isopropylsulfonyloxyimino)-1-cyclohexenylacetonitrile, and
α-(n-butylsulfonyloxyimino)-1-cyclohexenylacetonitrile.

Suitable bisoxime sulfonates include those described in JP-A 9-208554, for example,
bis(α-(4-toluenesulfonyloxy)imino)-p-phenylenediacetonitrile,
bis(α-(benzenesulfonyloxy)imino)-p-phenylenediacetonitrile,
bis(α-(methanesulfonyloxy)imino)-p-phenylenediacetonitrile,
bis(α-(butanesulfonyloxy)imino)-p-phenylenediacetonitrile,
bis(α-(10-camphorsulfonyloxy)imino)-p-phenylenediacetonitrile,
bis(α-(4-toluenesulfonyloxy)imino)-p-phenylenediacetonitrile,
bis(α-(trifluoromethanesulfonyloxy)imino)-p-phenylenediacetonitrile,
bis(α-(4-methoxybenzenesulfonyloxy)imino)-p-phenylenediacetonitrile,
bis(α-(4-toluenesulfonyloxy)imino)-m-phenylenediacetonitrile,
bis(α-(benzenesulfonyloxy)imino)-m-phenylenediacetonitrile,
bis(α-(methanesulfonyloxy)imino)-m-phenylenediacetonitrile,
bis(α-(butanesulfonyloxy)imino)-m-phenylenediacetonitrile,
bis(α-(10-camphorsulfonyloxy)imino)-m-phenylenediacetonitrile,
bis(α-(4-toluenesulfonyloxy)imino)-m-phenylenediacetonitrile,
bis(α-(trifluoromethanesulfonyloxy)imino)-m-phenylenediacetonitrile,
bis(α-(4-methoxybenzenesulfonyloxy)imino)-m-phenylenediacetonitrile, etc.

These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is added in an amount of 0.1 to 50 parts, and especially 0.5 to 40 parts by weight, per 100 parts by weight of the base resin (all parts are by weight, hereinafter). Less than 0.1 part of the photoacid generator may generate a less amount of acid upon exposure, sometimes leading to a poor sensitivity and resolution whereas more than 50 parts of the photoacid generator may adversely affect the transmittance and resolution of resist.

Component C

The organic solvent (C) used herein may be any organic solvent in which the base resin, photoacid generator, and other components are soluble. Illustrative, non-limiting, examples of the organic solvent include ketones such as cyclohexanone and methyl isopentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, propylene glycol monomethyl ether acetate, cyclohexanone, or a mixture thereof because the photoacid generator is most soluble therein.

An appropriate amount of the organic solvent used is about 200 to 1,000 parts, especially about 400 to 800 parts by weight per 100 parts by weight of the base resin.

Component D

The nitrogen-containing organic compound (D) is preferably a compound capable of suppressing the rate of diffusion when the acid generated by the photoacid generator diffuses within the resist film. The inclusion of the nitrogen-containing organic compound holds down the rate of acid diffusion within the resist film, resulting in better resolution. In addition, it suppresses changes in sensitivity following exposure, thus reducing substrate and environment dependence, as well as improving the exposure latitude and the pattern profile.

Examples of suitable nitrogen-containing organic compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, imide derivatives, and carbamates.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine.

Examples of suitable secondary aliphatic amines include dimethylamine, diethylamine, di-n-propylamine, di-isopropylamine, di-n-butylamine, diusobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine.

Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine.

Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, and diaminonaphthalene; and pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds having carboxyl group include aminobenzoic acid, indolecarboxylic acid, and amino acid derivatives (e.g., nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine).

Examples of suitable nitrogen-containing compounds having sulfonyl group include 3-pyridinesulfonic acid and pyridinium p-toluenesulfonate.

Examples of suitable nitrogen-containing compounds having hydroxyl group, nitrogen-containing compounds having hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide.

Examples of suitable amide derivatives include formamide, N-methylformamide, N,N-dimethylformamide, acetamide, N-methylacetamide, N,N-dimethylacetamide, propionamide, benzamide, and 1-cyclohexylpyrrolidone. Suitable imide derivatives include phthalimide, succinimide, and maleimide. Suitable carbamates include N-t-butoxycarbonyl-N,N-dicyclohexylamine, N-t-butoxycarbonylbenzimidazole, and oxazolidinone.

In addition, nitrogen-containing organic compounds of the following general formula (B)-1 may also be included alone or in admixture.

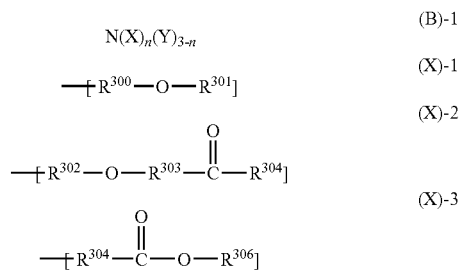

In the formulas, n is 1, 2 or 3. The side chain X may be the same or different and is represented by the formula (X)-1, (X)-2 or (X)-3. The side chain Y may be the same or different and stands for hydrogen or a straight, branched or cyclic alkyl group of 1 to 20 carbon atoms which may contain an ether or hydroxyl group. Two or three X's may bond together to form a ring. $R^{300}$, $R^{302}$ and $R^{305}$ are independently straight or branched alkylene groups of 1 to 4 carbon atoms; $R^{301}$ and $R^{304}$ are independently hydrogen or straight, branched or cyclic alkyl groups of 1 to 20 carbon atoms, which may contain at least one hydroxyl group, ether, ester or lactone ring; $R^{303}$ is a single bond or a straight or branched alkylene group of 1 to 4 carbon atoms; and $R^{306}$ is a straight, branched or cyclic alkyl group of 1 to 20 carbon atoms, which may contain at least one hydroxyl group, ether, ester or lactone ring.

Illustrative, non-limiting examples of the compounds of formula (B)-1 include
tris(2-methoxymethoxyethyl)amine,
tris{2-(2-methoxyethoxy)ethyl}amine,
tris{2-(2-methoxyethoxymethoxy)ethyl}amine,
tris{2-(1-methoxyethoxy)ethyl}amine,
tris{2-(1-ethoxyethoxy)ethyl}amine,
tris{2-(1-ethoxypropoxy)ethyl}amine,
tris[2-{2-(2-hydroxyethoxy)ethoxy}ethyl]amine,
4,7,13,16,21,24-hexaoxa-1,10-diazabicyclo[8.8.8]hexacosane,
4,7,13,18-tetraoxa-1,10-diazabicyclo[8.5.5]eicosane,
1,4,10,13-tetraoxa-7,16-diazabicyclooctadecane,
1-aza-12-crown-4, 1-aza-15-crown-5, 1-aza-18-crown-6,
tris(2-formyloxyethyl)amine, tris(2-acetoxyethyl)amine,
tris(2-propionyloxyethyl)amine, tris(2-butyryloxyethyl)amine,
tris(2-isobutyryloxyethyl)amine, tris(2-valeryloxyethyl)amine,
tris(2-pivaloyloxyethyl)amine,
N,N-bis(2-acetoxyethyl)-2-(acetoxyacetoxy)ethyl]amine,
tris(2-methoxycarbonyloxyethyl)amine,
tris(2-tert-butoxycarbonyloxyethyl)amine,
tris[2-(2-oxopropoxy)ethyl]amine,
tris[2-(methoxycarbonylmethyl)oxyethyl]amine,
tris[2-(tert-butoxycarbonylmethyloxy)ethyl]amine,
tris[2-(cyclohexyloxycarbonylmethyloxy)ethyl]amine,
tris(2-methoxycarbonylethyl)amine,
tris((2-ethoxycarbonylethyl)amine,
N,N-bis(2-hydroxyethyl)-2-(methoxycarbonyl)ethylamine,
N,N-bis(2-acetoxyethyl)-2-(methoxycarbonyl)ethylamine, N,N-bis(2-hydroxyethyl)-2-(ethoxycarbonyl)ethylamine,
N,N-bis(2-acetoxyethyl)-2-(ethoxycarbonyl)ethylamine,
N,N-bis(2-hydroxyethyl)-2-(2-methoxyethoxycarbonyl)ethylamine,
N,N-bis(2-acetoxyethyl)-2-(2-methoxyethoxycarbonyl)ethylamine,
N,N-bis(2-hydroxyethyl)-2-(2-hydroxyethoxycarbonyl)ethylamine,
N,N-bis(2-acetoxyethyl)-2-(2-acetoxyethoxycarbonyl)ethylamine,
N,N-bis(2-hydroxyethyl)-2-[(methoxycarbonyl)methoxycarbonyl]-ethylamine,
N,N-bis(2-acetoxyethyl)-2-[(methoxycarbonyl)methoxycarbonyl]-ethylamine,
N,N-bis(2-hydroxyethyl)-2-(2-oxopropoxycarbonyl)ethylamine,
N,N-bis(2-acetoxyethyl)-2-(2-oxopropoxycarbonyl)ethylamine,
N,N-bis(2-hydroxyethyl)-2-(tetrahydrofurfuryloxycarbonyl)-ethylamine,
N,N-bis(2-acetoxyethyl)-2-(tetrahydrofurfuryloxycarbonyl)-ethylamine,
N,N-bis(2-hydroxyethyl)-2-[(2-oxotetrahydrofuran-3-yl)oxy-carbonyl]ethylamine,
N,N-bis(2-acetoxyethyl)-2-[(2-oxotetrahydrofuran-3-yl)oxy-carbonyl]ethylamine,
N,N-bis(2-hydroxyethyl)-2-(4-hydroxybutoxycarbonyl)ethylamine,
N,N-bis(2-formyloxyethyl)-2-(4-formyloxybutoxycarbonyl)-ethylamine,
N,N-bis(2-formyloxyethyl)-2-(2-formyloxyethoxycarbonyl)-ethylamine,
N,N-bis(2-methoxyethyl)-2-(methoxycarbonyl)ethylamine,
N-(2-hydroxyethyl)-bis[2-(methoxycarbonyl)ethyl]amine,
N-(2-acetoxyethyl)-bis[2-(methoxycarbonyl)ethyl]amine,
N-(2-hydroxyethyl)-bis[2-(ethoxycarbonyl)ethyl]amine,
N-(2-acetoxyethyl)-bis[2-(ethoxycarbonyl)ethyl]amine,
N-(3-hydroxy-1-propyl)-bis[2-(methoxycarbonyl)ethyl]amine,
N-(3-acetoxy-1-propyl)-bis[2-(methoxycarbonyl)ethyl]amine,
N-(2-methoxyethyl)-bis[2-(methoxycarbonyl)ethyl]amine,
N-butyl-bis[2-(methoxycarbonyl)ethyl]amine,
N-butyl-bis[2-(2-methoxyethoxycarbonyl)ethyl]amine,
N-methyl-bis(2-acetoxyethyl)amine,
N-ethyl-bis(2-acetoxyethyl)amine,
N-methyl-bis(2-pivaloyloxyethyl)amine,
N-ethyl-bis[2-(methoxycarbonyloxy)ethyl]amine,
N-ethyl-bis[2-(tert-butoxycarbonyloxy)ethyl]amine,
tris(methoxycarbonylmethyl)amine,
tris(ethoxycarbonylmethyl)amine,
N-butyl-bis(methoxycarbonylmethyl)amine,
N-hexyl-bis(methoxycarbonylmethyl)amine, and
β-(diethylamino)-δ-valerolactone.

Also useful are one or more of nitrogen-containing organic cyclic structure compounds having the following general formula (B)-2.

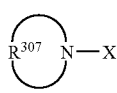

(B)-2

Herein X is as defined above, and $R^{307}$ is a straight or branched alkylene group of 2 to 20 carbon atoms which may contain one or more carbonyl, ether, ester or sulfide groups.

Illustrative examples of the compounds having formula (B)-2 include 1-[2-(methoxymethoxy)ethyl]pyrrolidine,
1-[2-(methoxymethoxy)ethyl]piperidine,
4-[2-(methoxymethoxy)ethyl]morpholine,
1-[2-[(2-methoxyethoxy)methoxy]ethyl]pyrrolidine,
1-[2-[(2-methoxyethoxy)methoxy]ethyl]piperidine,
4-[2-[(2-methoxyethoxy)methoxy]ethyl]morpholine,
2-(1-pyrrolidinyl)ethyl acetate, 2-piperidinoethyl acetate,
2-morpholinoethyl acetate, 2-(1-pyrrolidinyl)ethyl formate,
2-piperidinoethyl propionate,
2-morpholinoethyl acetoxyacetate,
2-(1-pyrrolidinyl)ethyl methoxyacetate,
4-[2-(methoxycarbonyloxy)ethyl]morpholine,
1-[2-(t-butoxycarbonyloxy)ethyl]piperidine,
4-[2-(2-methoxyethoxycarbonyloxy)ethyl]morpholine,
methyl 3-(1-pyrrolidinyl)propionate,
methyl 3-piperidinopropionate, methyl 3-morpholinopropionate,
methyl 3-(thiomorpholino)propionate,
methyl 2-methyl-3-(1-pyrrolidinyl)propionate,
ethyl 3-morpholinopropionate,
methoxycarbonylmethyl 3-piperidinopropionate,
2-hydroxyethyl 3-(1-pyrrolidinyl)propionate,
2-acetoxyethyl 3-morpholinopropionate,
2-oxotetrahydrofuran-3-yl 3-(1-pyrrolidinyl)propionate,
tetrahydrofurfuryl 3-morpholinopropionate,
glycidyl 3-piperidinopropionate,
2-methoxyethyl 3-morpholinopropionate,
2-(2-methoxyethoxy)ethyl 3-(1-pyrrolidinyl)propionate,
butyl 3-morpholinopropionate,
cyclohexyl 3-piperidinopropionate,
α-(1-pyrrolidinyl)methyl-γ-butyrolactone,
β-piperidino-γ-butyrolactone, β-morpholino-δ-valerolactone,
methyl 1-pyrrolidinylacetate, methyl piperidinoacetate,
methyl morpholinoacetate, methyl thiomorpholinoacetate,
ethyl 1-pyrrolidinylacetate, and
2-methoxyethyl morpholinoacetate.

Also, one or more of nitrogen-containing compounds having cyano represented by the following general formulae (B)-3 to (B)-6 may be blended.

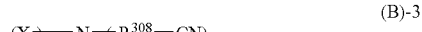

(B)-3

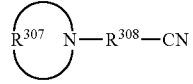

(B)-4

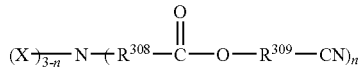

(B)-5

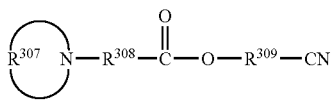

(B)-6

Herein, X, $R^{307}$ and n are as defined above, and $R^{308}$ and $R^{309}$ each are independently a straight or branched alkylene group of 1 to 4 carbon atoms.

Illustrative examples of the nitrogen-containing compounds having cyano as represented by formulae (B)-3 to (B)-6 include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl) aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

Also included are organic nitrogen-containing compounds having an imidazole skeleton and a polar functional group, represented by the general formula (B)-7.

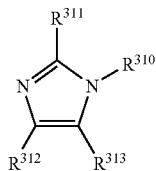

(B)-7

Herein, $R^{310}$ is a straight, branched or cyclic alkyl group of 2 to 20 carbon atoms bearing at least one polar functional group selected from among hydroxyl, carbonyl, ester, ether, sulfide, carbonate, cyano and acetal groups; $R^{311}$, $R^{312}$ and $R^{313}$ are each independently a hydrogen atom, a straight, branched or cyclic alkyl group, aryl group or aralkyl group having 1 to 10 carbon atoms.

Also included are organic nitrogen-containing compounds having a benzimidazole skeleton and a polar functional group, represented by the general formula (B)-8.

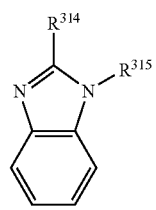

(B)-8

Herein, $R^{314}$ is a hydrogen atom, a straight, branched or cyclic alkyl group, aryl group or aralkyl group having 1 to carbon atoms. $R^{315}$ is a polar functional group-bearing, straight, branched or cyclic alkyl group of 1 to 20 carbon atoms, and the alkyl group contains as the polar functional group at least one group selected from among ester, acetal and cyano groups, and may additionally contain at least one group selected from among hydroxyl, carbonyl, ether, sulfide and carbonate groups.

Further included are heterocyclic nitrogen-containing compounds having a polar functional group, represented by the general formulae (B)-9 and (B)-10.

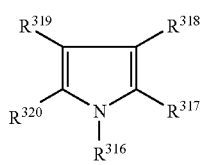

(B)-9

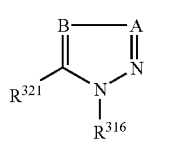

(B)-10

Herein, A is a nitrogen atom or =C—$R^{322}$, B is a nitrogen atom or =C—$R^{323}$, $R^{316}$ is a straight, branched or cyclic alkyl group of 2 to 20 carbon atoms bearing at least one polar functional group selected from among hydroxyl, carbonyl, ester, ether, sulfide, carbonate, cyano and acetal groups; $R^{317}$, $R^{318}$, $R^{319}$ and $R^{320}$ are each independently a hydrogen atom, a straight, branched or cyclic alkyl group or aryl group having 1 to 10 carbon atoms, or a pair of $R^{317}$ and $R^{318}$ and a pair of $R^{319}$ and $R^{320}$, taken together, may form a benzene, naphthalene or pyridine ring; $R^{321}$ is a hydrogen atom, a straight, branched or cyclic alkyl group or aryl group having 1 to 10 carbon atoms; $R^{322}$ and $R^{323}$ each are a hydrogen atom, a straight, branched or cyclic alkyl group or aryl group having 1 to 10 carbon atoms, or a pair of $R^{321}$ and $R^{323}$, taken together, may form a benzene or naphthalene ring.

Also included are nitrogen-containing organic compounds of aromatic carboxylic ester structure having the general formulae (B)-11 to (B)-14.

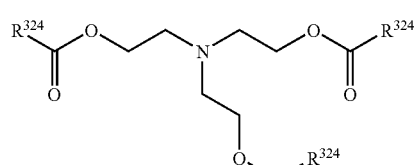
(B)-11

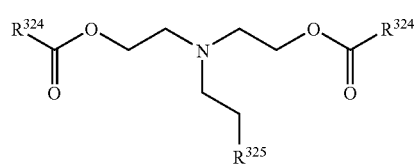
(B)-12

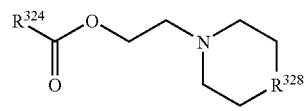
(B)-13

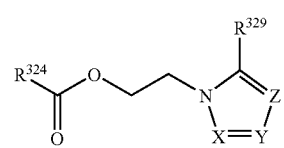
(B)-14

Herein $R^{324}$ is a $C_6$-$C_{20}$ aryl group or $C_4$-$C_{20}$ hetero-aromatic group, in which some or all of hydrogen atoms may be replaced by halogen atoms, straight, branched or cyclic $C_1$-$C_{20}$ alkyl groups, $C_6$-$C_{20}$ aryl groups, $C_7$-$C_{20}$ aralkyl groups, $C_1$-$C_{10}$ alkoxy groups, $C_1$-$C_{10}$ acyloxy groups or $C_1$-$C_{10}$ alkylthio groups. $R^{325}$ is $CO_2R^{326}$, $OR^{327}$ or cyano group. $R^{326}$ is a $C_1$-$C_{10}$ alkyl group, in which some methylene groups may be replaced by oxygen atoms. $R^{327}$ is a $C_1$-$C_{10}$ alkyl or acyl group, in which some methylene groups may be replaced by oxygen atoms. $R^{328}$ is a single bond, methylene, ethylene, sulfur atom or —O(CH$_2$CH$_2$O)$_n$— group wherein n is 0, 1, 2, 3 or 4. $R^{329}$ is hydrogen, methyl, ethyl or phenyl. X is a nitrogen atom or $CR^{330}$. Y is a nitrogen atom or $CR^{331}$. Z is a nitrogen atom or $CR^{332}$. $R^{330}$, $R^{331}$ and $R^{332}$ are each independently hydrogen, methyl or phenyl. Alternatively, a pair of $R^{330}$ and $R^{331}$ or a pair of $R^{331}$ and $R^{332}$ may bond together to form a $C_6$-$C_{20}$ aromatic ring or $C_2$-$C_{20}$ hetero-aromatic ring.

Further included are nitrogen-containing organic compounds of 7-oxanorbornane-2-carboxylic ester structure having the general formula (B)-15.

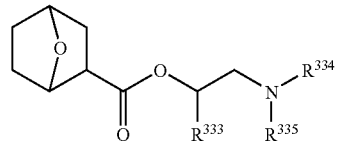
(B)-15

Herein $R^{333}$ is hydrogen or a straight, branched or cyclic $C_1$-$C_{10}$ alkyl group. $R^{334}$ and $R^{335}$ are each independently a $C_1$-$C_{20}$ alkyl group, $C_6$-$C_{20}$ aryl group or $C_7$-$C_{20}$ aralkyl group, which may contain one or more polar functional groups selected from among ether, carbonyl, ester, alcohol, sulfide, nitrile, amine, imine, and amide and in which some hydrogen atoms may be replaced by halogen atoms. $R^{334}$ and $R^{335}$, taken together, may form a heterocyclic or hetero-aromatic ring of 2 to 20 carbon atoms.

The organic nitrogen-containing compounds may be used alone or in admixture of two or more. The organic nitrogen-containing compound is preferably formulated in an amount of 0.001 to 2 parts, and especially 0.01 to 1 part by weight, per 100 parts by weight of the entire base resin. Less than 0.001 part of the nitrogen-containing compound achieves no or little addition effect whereas more than 2 parts would result in too low a sensitivity.

While the resist composition of the invention is basically composed of the inventive polymer, the photoacid generator, the organic solvent and optionally the nitrogen-containing organic compound as described above, it may further include any well-known components such as dissolution inhibitors, acidic compounds, stabilizers, dyes, and surfactants, if necessary.

Pattern formation using the resist composition of the invention may be carried out by a known lithographic technique. For example, the resist composition is applied onto a substrate such as a silicon wafer by spin coating or the like to form a resist film having a thickness of 0.3 to 2.0 μm, which is then pre-baked on a hot plate at 60 to 150° C. for 1 to 10 minutes, and preferably at 80 to 130° C. for 1 to 5 minutes. A patterning mask having the desired pattern is then placed over the resist film, and the film exposed through the mask to an electron beam or to high-energy radiation such as deep-UV rays, an excimer laser, or x-rays in a dose of about 1 to 200 mJ/cm$^2$, and preferably about 10 to 100 mJ/cm$^2$, then post-exposure baked (PEB) on a hot plate at 60 to 150° C. for 1 to 5 minutes, and preferably at 80 to 130° C. for 1 to 3 minutes. Finally, development is carried out using as the developer an aqueous alkali solution, such as a 0.1 to 5 wt % (preferably 2 to 3 wt %) aqueous solution of tetramethylammonium hydroxide (TMAH), this being done by a conventional technique such as dip, puddle, or spray technique for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV or excimer laser radiation having a wavelength of 248 to 157 nm, x-rays, or an electron beam. The desired pattern may not be obtainable outside the upper and lower limits of the above range.

EXAMPLE

Examples of the invention are given below by way of illustration and not by way of limitation.

Example 1

Synthesis of 4,4-difluoro-5-hydroxy-3-methyl-5-trifluoromethyloxolane-3-yl methacrylate (synthesis of oxolane hemiacetal monomer)

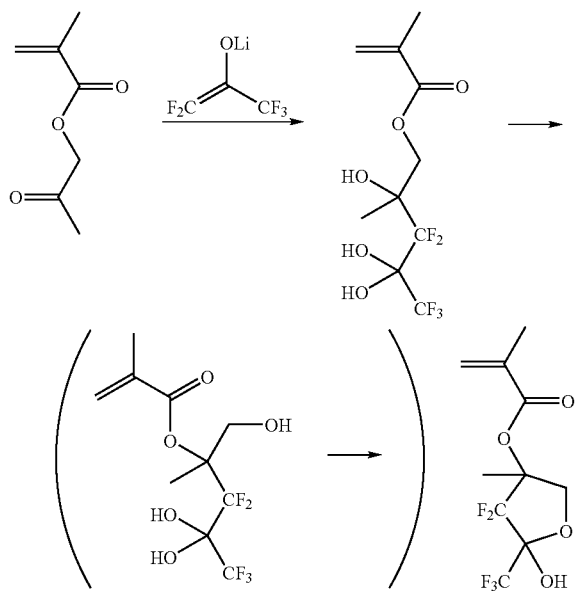

[1-1] Synthesis of 2-methyl-3,3,5,5,5-pentafluoro-2,4,4-trihydroxypentyl methacrylate In a nitrogen atmosphere at 5° C., 1290 ml of 1.6M butyllithium in hexane was added to a mixture of 168 g of 1,1,1,3,3,3-hexafluoro-2-propanol and 1200 g of tetrahydrofuran, followed by one hour of stirring at 5° C. Then 142 g of 2-oxopropyl methacrylate was added at 5° C. The mixture was stirred for 10 hours, after which dilute hydrochloric acid was added to quench the reaction and neutralize the reaction mixture. This was followed by conventional aqueous work-up and purification by silica gel column chromatography, collecting 253 g of the product (yield 82%).

2-methyl-3,3,5,5,5-pentafluoro-2,4,4-trihydroxypentyl methacrylate

Colorless solid
IR (KBr): ν=3380, 3006, 2970, 1697, 1639, 1471, 1457, 1394, 1382, 1363, 1330, 1307, 1274, 1209, 1172, 1116, 1089, 1020, 993, 973, 950, 904, 819, 744, 698 $cm^{-1}$
$^{1}$H-NMR (600 MHz in DMSO-d6): δ=1.37 (3H, s), 1.89 (3H, m), 4.27 (1H, d, J=11.3 Hz), 4.34 (1H, d, J=11.3 Hz), 5.70 (1H, m), 6.09 (1H, m), 6.34 (1H, s), 7.85 (1H, s), 7.99 (1H, s) ppm
$^{19}$F-NMR (565 MHz in DMSO-d6): δ=−121.7 (1F, dq, J=264.5, 13.4 Hz), -120.6 (1F, dq, J=264.5, 11.9 Hz), -80.6 (3F, dd, J=13.4, 11.9 Hz) ppm

[1-2] Synthesis of 4,4-difluoro-5-hydroxy-3-methyl-5-trifluoromethyloxolane-3-yl methacrylate via route 1 (cyclization of hemiacetal under basic conditions)

In a nitrogen atmosphere, a mixture of 30 g of the triol compound obtained in [1-1], 19.5 g of triethylamine and 150 g of toluene was stirred for 4 hours at 70° C. The reaction mixture was cooled to room temperature and neutralized with dilute hydrochloric acid, after which the organic layer was separated. Ordinary work-up including washing, drying and concentration yielded a crude product, which was distilled in vacuo, collecting 25.1 g of the product (yield 89%).

4,4-difluoro-5-hydroxy-3-methyl-5-trifluoromethyloxolane-3-yl methacrylate (mixture of ca. 60:40 diastereomers)

Viscous liquid
Boiling point 65° C./27 Pa
IR (KBr): ν=3399, 1712, 1637, 1454, 1332, 1203, 1164, 1064, 991 $cm^{-1}$
$^{1}$H-NMR (600 MHz in DMSO-d6): δ=1.60 (3×0.4H, d, J=3.8 Hz), 1.68 (3×0.6H, d, J=2.4 Hz), 1.86-1.85 (3H, m), 4.30 (0.6H, d, J=9.6 Hz), 4.31 (0.4H, dd, J=10.7, 1.7 Hz), 4.37 (0.6H, d, J=10.3 Hz), 4.41 (0.4H, d, J=10.7 Hz), 5.76-5.79 (1H, m), 6.06-6.08 (0.6H, m), 6.09-6.15 (0.4H, m), 8.73 (0.4H, OH, br.s), 8.92 (0.6H, OH, br.s) ppm
$^{1}$F-NMR (565 MHz in DMSO-d6, trifluoroacetic acid standard (same hereinafter)): δ=−125.1 (0.6F, dq, J=235.3, 17.3 Hz), −122.6 (0.4F, dq, J=235.3, 17.0 Hz), −122.2 (0.6F, d, J=239.6 Hz), −120.4 (0.4F, d, J=239.6 Hz), −80.1 (3×0.4F, d-like, J=16.3 Hz), −80.5 (2×0.6F, d-like, J=17.3 Hz) ppm It is presumed herein that under basic conditions, there is formed a triol compound in which the methacryloyl group has made transposition from a primary hydroxyl group to a tertiary hydroxyl group so that the primary hydroxyl group becomes free, that is, a hydrated derivative which is an equivalent of a keto-alcohol compound, which undergoes hemiacetal cyclization to form an oxolane hemiacetal compound.

[1-3] Synthesis of 4,4-difluoro-5-hydroxy-3-methyl-5-trifluoromethyloxolane-3-yl methacrylate via route 2 (cyclization of hemiacetal under acidic conditions)

In a nitrogen atmosphere, a catalytic amount of p-toluenesulfonic acid monohydrate was added to a mixture of 2.0 g of the triol compound obtained in [1-1] and 50 g of toluene, which was stirred for 24 hours at 70° C. The reaction mixture was cooled to room temperature. Ordinary work-up including washing, drying and concentration yielded a crude product, which was distilled in vacuo, collecting 1.34 g of the product (yield 71%). It was obtained as a mixture of ca. 55:45 diastereomers and its spectral data were identical with those of [1-2] except the isomer ratio.

Example 2

Synthesis of 2,6-dicyclohexyl-5,5-difluoro-4-trifluoromethyl-1,3-dioxan-4-ol (synthesis of dioxane hemiacetal)

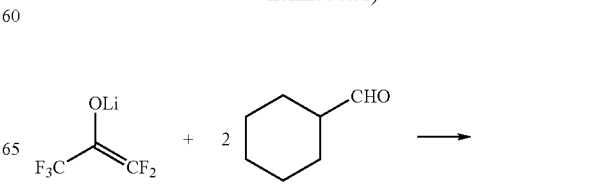

-continued

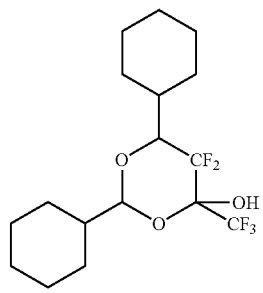

In a nitrogen atmosphere at 5° C., 80 ml of 2.59M n-butyllithium in hexane was added to a mixture of 16.8 g of 1,1,1,3,3,3-hexafluoro-2-propanol and 100 g of tetrahydrofuran, followed by 2 hours of stirring at 5° C. Then 25 g of cyclohexanecarboxaldehyde was added at 5° C. The mixture was stirred for 4 hours, after which dilute hydrochloric acid was added to quench the reaction and neutralize the reaction mixture. This was followed by conventional aqueous work-up and purification by silica gel column chromatography, collecting 28.6 g of the product (yield 77%).

2,6-dicyclohexyl-5,5-difluoro-4-trifluoromethyl-1,3-dioxan-4-ol

Viscous liquid

GC-MS (EI): (m/z)$^+$=55, 95, 113, 243, 289

GC-MS (CI, methane): (m/z)$^+$=95, 113, 243, 355, 373 [(M+H)$^+$]

GC-MS (CI, isobutane): (m/z)$^+$=95, 113, 243, 261, 355, 373 [(M+H)$^+$]

Example 3

Synthesis of 2,6-di(2-adamantyl)-5,5-difluoro-4-trifluoromethyl-1,3-dioxan-4-ol (synthesis of dioxane hemiacetal)

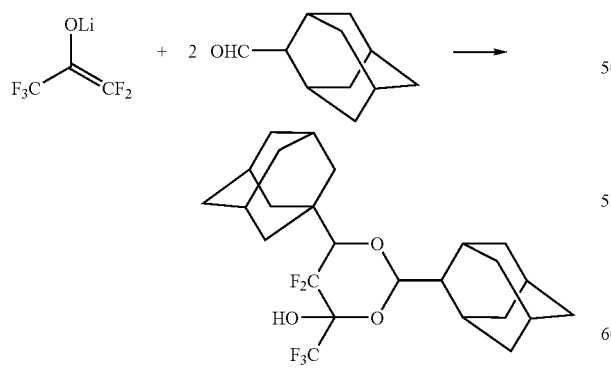

By following the same procedure as in Example 2 aside from using an equimolar amount of adamantane-2-carboxaldehyde instead of cyclohexanecarboxaldehyde, the product was obtained (yield 70%).

2,6-di(2-adamantyl)-5,5-difluoro-4-trifluoromethyl-1,3-dioxan-4-ol

Colorless solid

IR (KBr): ν=2919, 2852, 1710, 1454, 1213, 1099 cm$^{-1}$ $^1$H-NMR (600 MHz in DMSO-d6): δ=1.52-1.99 (29H, m), 2.17 (1H, d, J=10.0 Hz), 4.48 (1H, dd, J=10.3, 23.4 Hz), 5.48 (1H, d, J=8.6 Hz), 8.91 (1H, d-like, J=2.7 Hz) ppm $^{19}$F-NMR (565 MHz in DMSO-d6): δ=−133.7 (1F, ddq, J=22.8, 248.2, 9.7 Hz), −122.3 (1F, dd, J=5.4, 248.2 Hz), −80.3 (3F, dd, J=7.6, 15.2 Hz) ppm $^{13}$C-NMR (565 MHz in DMSO-d6): δ=26.85, 27.43, 27.45, 27.48, 27.62, 27.67, 27.83, 28.61, 28.66, 31.70, 32.18, 32.29, 32.33, 37.98, 38.03, 38.16, 38.28, 38.41, 38.49, 41.81, 46.65, 74.29 (dd, J=23.7, 27.3 Hz), 92.65 (tq-like, J=32.4, 24.5 Hz), 96.26, 133.75 (dd, J=259.8, 262.7 Hz), 120.90 (q, J=287.9 Hz) ppm Example 4

Synthesis of (5-cyclohexyl-4,4-difluoro-3-hydroxy-1-methyl-3-trifluoromethyl-1,3-dioxan-1-yl)methyl methacrylate (synthesis of dioxane hemiacetal monomer)

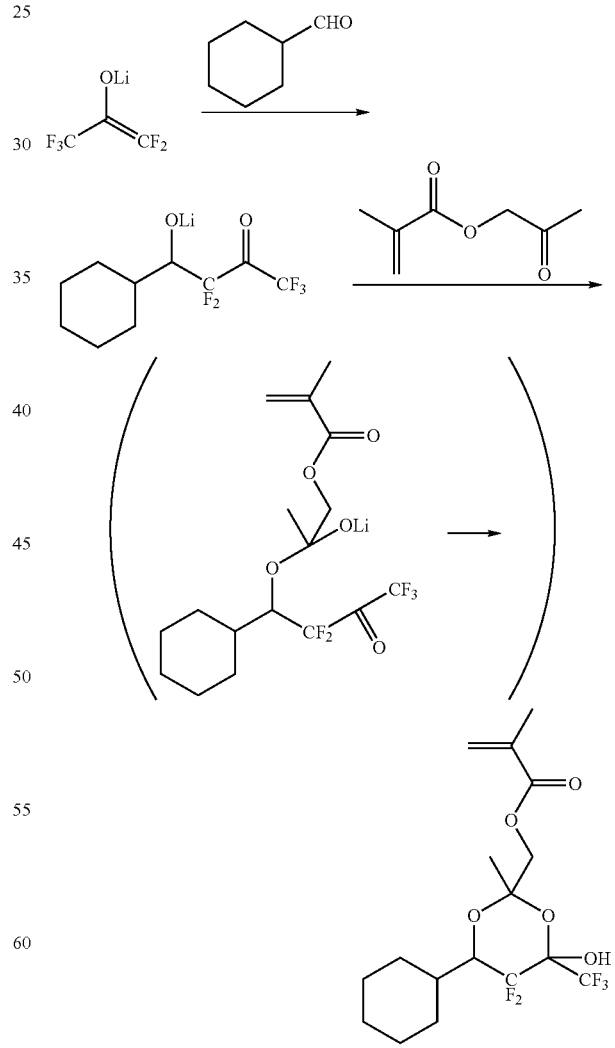

In a nitrogen atmosphere at 5° C., 80 ml of 2.59M n-butyllithium in hexane was added to a mixture of 16.8 g of 1,1,1, 3,3,3-hexafluoro-2-propanol and 80 ml of tetrahydrofuran, followed by 2 hours of stirring at 5° C. A mixture of 10 g of cyclohexanecarboxaldehyde and 50 ml of tetrahydrofuran was then added dropwise at 5° C. The mixture was stirred for 1 hour at the temperature, after which a mixture of 12.7 g of 2-oxopropyl methacrylate and 50 ml of tetrahydrofuran was added dropwise. The mixture was stirred for 18 hours at room temperature, after which dilute hydrochloric acid was added to quench the reaction and neutralize the reaction mixture. This was followed by conventional aqueous work-up and purification by silica gel column chromatography, collecting 16.8 g of the product (yield 42%).

(5-cyclohexyl-4,4-difluoro-3-hydroxy-1-methyl-3-trifluoromethyl-1,3-dioxan-1-yl)methyl methacrylate Viscous liquid
GC-MS (EI, main diastereomer): (m/z)$^+$=41, 69, 155, 185
GC-MS (CI, methane, main diastereomer): (m/z)$^+$=112, 143, 181, 199, 267, 285
GC-MS (CI, isobutane, main diastereomer): (m/z)$^+$=143, 181, 199, 267, 285, 323

It is presumed that in this Example, a fluoro enolate reacts with two carbonyl compounds sequentially to form a keto-alkoxide compound, that is, an equivalent of a keto-alcohol compound, which undergoes hemiacetal cyclization to form a dioxane hemiacetal compound.

Example 5

Synthesis of (5,5-difluoro-6-hydroxy-4-methyl-6-trifluoromethyl-1,3-dioxan-4-yl)methyl methacrylate (synthesis of dioxane hemiacetal monomer)

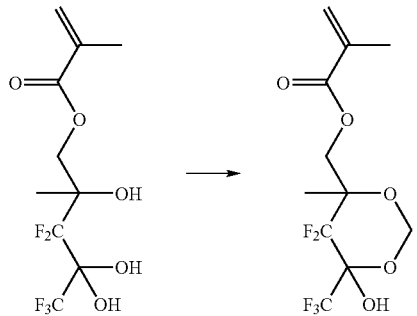

A mixture of 15.0 g of the triol compound, an equivalent of keto-alcohol compound, obtained in [1-1], 1.2 g of a cation-exchange resin (sulfonic acid type), 5.0 g of s-trioxane, and 60 g of toluene was stirred for 16 hours at 60° C. The reaction mixture was cooled down, after which the cation-exchange resin was filtered off. The solvent was distilled off, followed by vacuum distillation to collect 12.8 g of (5,5-difluoro-6-hydroxy-4-methyl-6-trifluoromethyl-1,3-dioxan-4-yl)methyl methacrylate (yield 82%).

(5,5-difluoro-6-hydroxy-4-methyl-6-trifluoromethyl-1,3-dioxan-4-yl)methyl methacrylate Colorless solid at room temperature
Boiling point 97-101° C./27 Pa
IR (KBr): ν=3328, 3028, 2997, 2972, 2922, 1698, 1637, 1469, 1392, 1338, 1326, 1305, 1213, 1168, 1122, 1089, 1079, 1041, 997, 964, 813, 746, 657 cm$^{-1}$ $^1$H-NMR (600 MHz in DMSO-d6): δ=1.36 (1.83H, d, J=2.8 Hz), 1.62 (1.17H, d, J=2.0 Hz), 1.88 (1.17H, m), 1.90 (1.83H, m), 4.02 (0.61H, dd, J=12.7, 2.8 Hz), 4.14 (0.39H, dd, J=11.3, 3.1 Hz), 4.30 (0.39H, d, J=11.3 Hz), 4.94 (0.61H, d, J=6.9 Hz), 5.02 (0.39H, d, J=6.9 Hz), 5.29 (0.39H, d, J=6.9 Hz), 5.32 (0.61H, d, J=6.9 Hz), 5.40 (0.61H, d, J=12.7 Hz), 5.72-5.75 (1H, m), 6.06 (0.39H, m), 6.08 (0.61H, m), 9.15 (0.39H, d, J=3.8 Hz), 9.42 (0.61H, d, J=4.1 Hz) ppm $^{13}$C-NMR (150 MHz in DMSO-d6): δ=16.15, 18.14 (d, J=10 Hz), 19.27, 19.37, 60.91, 66.39 (d, J=13 Hz), 78.11 (t, J=23 Hz), 78.94 (t, J=24 Hz), 82.25, 82.63, 93.0-93.5 (m×2), 113.61 (dd, J=266, 256 Hz), 114.12 (dd, J=269, 256 Hz), 122.53 (q×2, J=287 Hz), 128.05, 128.10, 136.79, 136.87, 167.28, 167.62 ppm $^{19}$F-NMR (565 MHz in DMSO-d6): δ=−128.33 (0.39F, dq, J=253, 17 Hz), −125.80 (0.61F, dd, J=258, 5 Hz), −124.06 (0.61F, dq, J=258, 16 Hz), −122.08 (0.39F, br.d, J=253 Hz), −80.71 (1.83F, dd, J=16, 6 Hz), −80.68 (1.17F, dd, J=17, 6 Hz) ppm Example 6

Synthesis of (2-t-butyl-5,5-difluoro-6-hydroxy-4-methyl-6-trifluoromethyl-1,3-dioxan-4-yl)methyl methacrylate (synthesis of dioxane hemiacetal monomer)

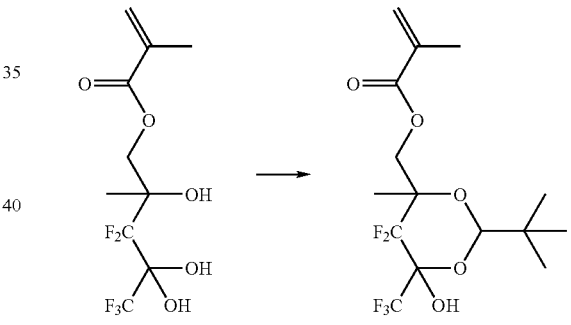

A mixture of 15.0 g of the triol compound, an equivalent of keto-alcohol compound, obtained in [1-1], 1.2 g of a cation-exchange resin (sulfonic acid type), 21.0 g of pivalaldehyde, and 60 g of toluene was stirred for 48 hours. The cation-exchange resin was filtered off and a low-boiling fraction distilled off. This was purified by silica gel column chromatography, leaving 11.9 g of (2-t-butyl-5,5-difluoro-6-hydroxy-4-methyl-6-trifluoromethyl-1,3-dioxan-4-yl)methyl methacrylate (yield 65%).

(2-t-butyl-5,5-difluoro-6-hydroxy-4-methyl-6-trifluoromethyl-1,3-dioxan-4-yl)methyl methacrylate GC-MS (EI, main diastereomer): (m/z)$^+$=41, 69, 87, 143, 233, 273, 319
GC-MS (CI, methane, main diastereomer): (m/z)$^+$=69, 87, 115, 205, 233, 271, 273, 291, 357, 359 [(M−OH)$^+$]
GC-MS (CI, isobutane, main diastereomer): (m/z)$^+$=69, 87, 143, 291, 346, 377 [(M+H)$^+$]

Example 7

Synthesis of 5,5-difluoro-6-(5-norbornen-2-yl)-4-trifluoromethyl-1,3-dioxan-4-ol (synthesis of dioxane hemiacetal monomer)

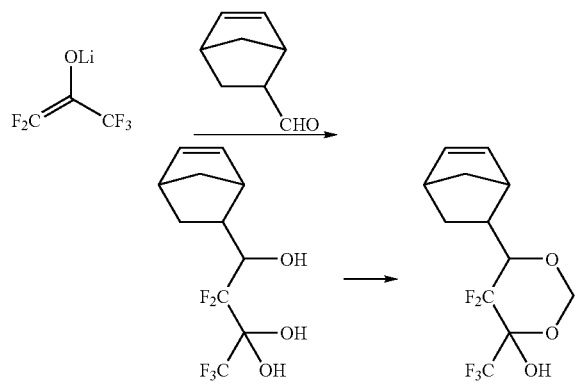

[7-1] Synthesis of 1-(5-norbornen-2-yl)-2,2,4,4,4-pentafluorobutane-1,3,3-triol In a nitrogen atmosphere at −70° C., 1290 ml of 1.6M n-butyllithium in hexane was added to a mixture of 168 g of 1,1,1,3,3,3-hexafluoro-2-propanol and 1200 g of tetrahydrofuran. The mixture was allowed to warm up slowly to 0° C. and stirred at the temperature for 30 minutes. Then 134 g of 5-norbornene-2-carboxaldehyde was added at 0° C. The mixture was stirred for 1 hour, after which dilute hydrochloric acid was added to quench the reaction and neutralize the reaction mixture. This was followed by conventional aqueous work-up and purification by silica gel column chromatography, collecting 230 g of 1-(5-norbornen-2-yl)-2,2,4,4,4-pentafluorobutane-1,3,3-triol (yield 80% based on the 1,1,1,3,3,3-hexafluoro-2-propanol).

1-(5-norbornen-2-yl)-2,2,4,4,4-pentafluorobutane-1,3,3-triol

Colorless solid
IR (KBr): ν=3409, 3288, 3062, 2979, 2946, 2923, 2879, 1486, 1454, 1423, 1338, 1311, 1255, 1241, 1207, 1172, 1153, 1112, 1076, 1025, 900, 842, 711 cm$^{-1}$
$^1$H-NMR (300 MHz in DMSO-d6, main diastereomer): δ=0.72 (1H, m), 1.18 (1H, br.d, J=8.0 Hz), 1.29 (1H, br.d, J=8.0 Hz), 1.74 (1H, ddd, J=12.0, 9.0, 3.7 Hz), 2.44 (1H, m), 2.77 (1H, m), 3.02 (1H, m), 3.52 (1H, ddd, J=22.0, 10.6, 7.4 Hz), 6.02 (1H, dd, J=5.7, 2.8 Hz), 6.19 (1H, dd, J=5.7, 3.0 Hz), 6.29 (1H, d, J=7.4 Hz), 7.37 (1H, s), 7.96 (1H, d, J=1.9 Hz) ppm
$^{19}$F-NMR (283 MHz in CDCl$_3$, main diastereomer): δ=−130.0 (1F), −120.6 (1F), −82.0 (3F) ppm

[7-2] Synthesis of 5,5-difluoro-6-(5-norbornen-2-yl)-4-trifluoromethyl-1,3-dioxan-4-ol A mixture of 40.0 g of the triol compound, an equivalent of keto-alcohol compound, obtained in [7-1], 3.4 g of a cation-exchange resin (sulfonic acid type), 15.0 g of s-trioxane, and 200 g of toluene was stirred for 24 hours at 60° C. The cation-exchange resin was filtered off, after which the reaction solution was directly purified by column chromatography, obtaining 32.1 g of 5,5-difluoro-6-(5-norbornen-2-yl)-4-trifluoromethyl-1,3-dioxan-4-ol (yield 76%).

5,5-difluoro-6-(5-norbornen-2-yl)-4-trifluoromethyl-1,3-dioxan-4-ol

Colorless solid
IR (KBr): ν=3396, 3061, 3034, 3001, 2978, 2954, 2931, 2902, 2881, 1351, 1340, 1330, 1245, 1222, 1209, 1178, 1141, 1103, 1072, 1062, 1041, 993, 914, 844, 835, 732, 719, 690, 671, 649 cm$^{-1}$
$^1$H-NMR (600 MHz in DMSO-d6, main diastereomer): δ=0.75 (1H, ddd, J=11.6, 6.9, 3.8 Hz), 1.19 (1H, d, J=8.2 Hz), 1.29 (1H, dd, J=8.2, 1.4 Hz), 1.78 (1H, ddd, J=11.6, 9.3, 3.8 Hz), 2.43 (1H, dddd, J=10.7, 9.3, 3.8, 3.7 Hz), 2.81 (1H, m), 2.96 (1H, m), 3.38 (1H, dd, J=22.7, 10.7 Hz), 5.02 (2H, s), 5.97 (1H, dd, J=5.5, 2.8 Hz), 6.23 (1H, dd, J=5.5, 3.1 Hz), 8.94 (1H, d, J=3.1 Hz) ppm
$^{13}$C-NMR (150 MHz in DMSO-d6, main diastereomer): δ=28.16 (d, J=5 Hz), 35.62, 41.84, 43.37, 47.35, 77.66 (dd, J=25, 22 Hz), 85.96, 91.77 (dquint-like, J=23, 31 Hz), 113.68 (dd, J=261, 255 Hz), 121.17 (q, J=287 Hz), 132.00, 138.06 ppm
$^{19}$F-NMR (565 MHz in DMSO-d6, main diastereomer): δ=−131.21 (1F, ddq, J=247, 24, 14 Hz), −122.51 (1F, dm, J=247 Hz), −80.40 (3F, dd, J=14, 7 Hz) ppm

Example 8

Synthesis of 5,5-difluoro-6-(5-norbornen-2-yl)-2-propyl-4-trifluoromethyl-1,3-dioxan-4-ol (synthesis of dioxane hemiacetal monomer)

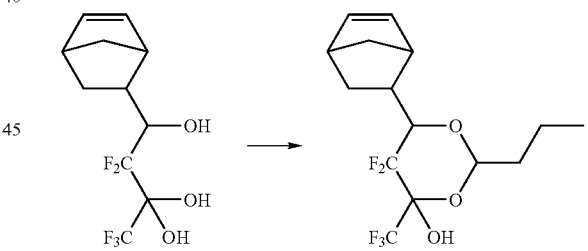

A mixture of 9.0 g of the triol compound, an equivalent of keto-alcohol compound, obtained in [7-1], 1.0 g of a cation-exchange resin (sulfonic acid type), 2.3 g of pivalaldehyde, and 50 g of toluene was stirred for 48 hours. The cation-exchange resin was filtered off and a low-boiling fraction distilled off. This was purified by silica gel column chromatography, leaving 6.6 g of 5,5-difluoro-6-(5-norbornen-2-yl)-2-propyl-4-trifluoromethyl-1,3-dioxan-4-ol (yield 62%).

5,5-difluoro-6-(5-norbornen-2-yl)-2-propyl-4-trifluoromethyl-1,3-dioxan-4-ol

GC-MS (EI): (m/z)$^+$=27, 43, 66, 91, 253, 270, 342 (M$^+$)
GC-MS (CI, methane): (m/z)$^+$=73, 95, 129, 149, 169, 205, 231, 251, 271, 325, 343 [(M+H)$^+$]

Example 9

Synthesis of spiro[adamantane-4,4'-5',5'-difluoro-6'-hydroxy-6'-trifluoromethyl-1',3'-dioxan]-1-yl methacrylate (synthesis of dioxane hemiacetal monomer)

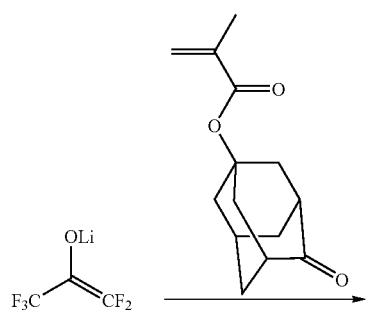

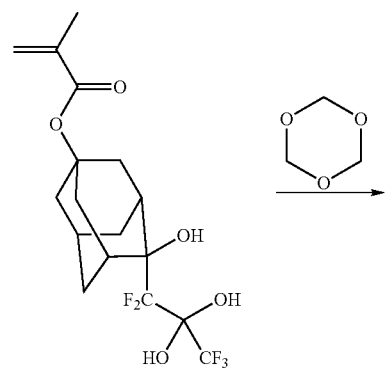

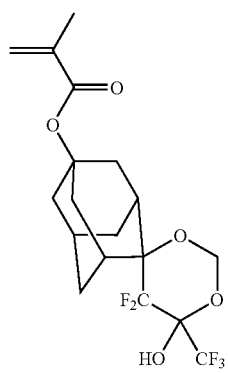

In a nitrogen atmosphere at 5° C., 80 ml of 2.59M n-butyllithium in hexane was added to a mixture of 16.8 g of 1,1,1,3,3,3-hexafluoro-2-propanol and 80 ml of tetrahydrofuran, followed by 2 hours of stirring at 5° C. A mixture of 23.0 g of 4-oxo-1-adamantyl methacrylate and 50 ml of tetrahydrofuran was then added dropwise at 5° C. The mixture was stirred at the temperature for 1 hour and at room temperature for 18 hours, after which dilute hydrochloric acid was added to quench the reaction and neutralize the reaction mixture. This was followed by conventional aqueous work-up, obtaining in crude form a triol compound which was an equivalent of keto-alcohol compound. The crude product was combined with 2 g of a cation-exchange resin (sulfonic acid type), 10.5 g of s-trioxane and 140 g of toluene. The mixture was stirred at 60° C. for 24 hours. The cation-exchange resin was filtered off, after which the reaction solution was directly purified by column chromatography, collecting 16.5 g of the compound (yield 40%).

spiro[adamantane-4,4'-5',5'-difluoro-6'-hydroxy-6'-trifluoromethyl-1',3'-dioxan]-1-yl methacrylate (mixture of ca. 80:20 diastereomers)

Colorless solid

IR (KBr): ν=3313, 1689, 1631, 1459, 1346, 1332, 1209, 1174, 1106, 1043, 989 cm$^{-1}$ $^{19}$F-NMR (565 MHz in DMSO-d6): δ=−123.86 (0.8F, dq, 16.3 Hz), −122.48 (0.2F, dq, J=255, 16.3 Hz), −112.71 (0.8F, d, J=255 Hz), −112.01 (0.2F, d, J=256 Hz), −80.33 (3×0.8F, dd, J=8.7, 15 Hz), −80.25 (2×0.2F, dd, J=8.7, 16 Hz) ppm

Example 10

Synthesis of [4,6-dihydroxy-3,3,5,5-tetrafluoro-4,6-bis(trifluoromethyl)-2-methyloxan-2-yl]methyl methacrylate (synthesis of oxane hemiacetal monomer)

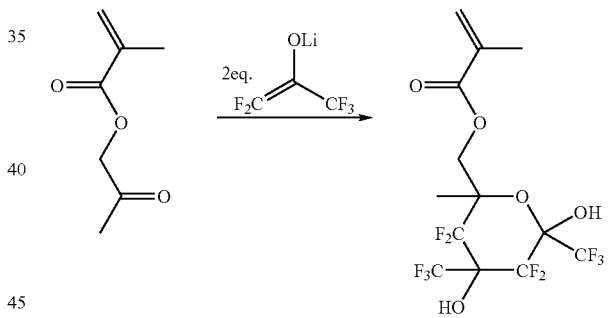

In a nitrogen atmosphere at 5° C., 258 ml of 1.6M butyllithium in hexane was added to a mixture of 33.6 g of 1,1,1,3,3,3-hexafluoro-2-propanol and 240 g of tetrahydrofuran, followed by one hour of stirring at 5° C. Then 14.2 g of 2-oxopropyl methacrylate was added at 5° C. Reaction took place, after which dilute hydrochloric acid was added for neutralization. This was followed by conventional aqueous work-up and purification by silica gel column chromatography, collecting 30.2 g of the compound (yield 69%).

[4,6-dihydroxy-3,3,5,5-tetrafluoro-4,6-bis(trifluoromethyl)-2-methyloxan-2-yl]methyl methacrylate GC-MS (EI): (m/z)$^+$=43, 69, 101, 169, 217, 248, 287, 356

GC-MS (CI, methane): (m/z)$^+$=75, 129, 169, 197, 217, 245, 291, 401, 421, 439 [(M+H)$^+$]

Example 11

Synthesis of poly(4,4-difluoro-5-hydroxy-3-methyl-5-trifluoromethyloxolane-3-yl methacrylate) (homopolymer)

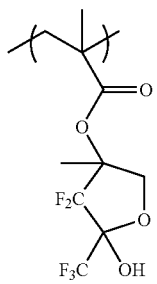

In a nitrogen atmosphere, a mixture of 5.00 g of 4,4-difluoro-5-hydroxy-3-methyl-5-trifluoromethylfuran-3-yl methacrylate, 23 mg of 2-mercaptoethanol, and 20.00 g of tetrahydrofuran was stirred at 600C, to which 47 mg of 2,2'-azobisisobutyronitrile was added. While keeping at 60° C., the mixture was stirred for a further 20 hours. The polymerization liquid was cooled to room temperature, and with vigorous stirring, added dropwise to 500 ml of n-hexane. The resulting solids were collected by filtration and vacuum dried at 50° C. for 15 hours, leaving 4.55 g of a polymer in white powder solid form (yield 91%). The polymer had a weight average molecular weight (Mw) of 18,600 as determined by GPC versus polystyrene standards.

A polymer solution was prepared by dissolving 1 g of the homopolymer in 10 g of propylene glycol monomethyl ether acetate (PGMEA) and passing through a filter with a pore size of 0.2 μm. It was spin coated onto a 8-inch diameter silicon wafer and baked on a hot plate at 110° C. for 60 seconds, forming a polymer film of 300 nm thick. Using a dissolution rate-measuring device Model RDA-790 (by Lithotec Japan Co., Ltd.), the dissolution rate of the polymer film in a 2.38 wt % tetramethylammonium hydroxide aqueous solution was measured. The dissolution rate was 26,000 angstrom/sec, indicating that the polymer performs well as an alkali-soluble resin.

Example 12

Synthesis of poly(3-ethyl-3-exo-tetracyclo[4.4.0.1$^{2,5}$.1$^{7,10}$]-dodecanyl methacrylate-co-3-hydroxy-1-adamantyl methacrylate-co-4,8-dioxatricyclo[4.2.1.0$^{3,7}$]nonan-5-on-2-yl methacrylate-co-4,4-difluoro-5-hydroxy-3-methyl-5-trifluoromethylfuran-3-yl methacrylate)

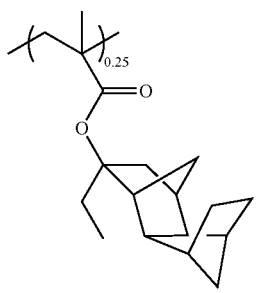 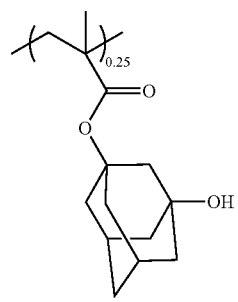

-continued

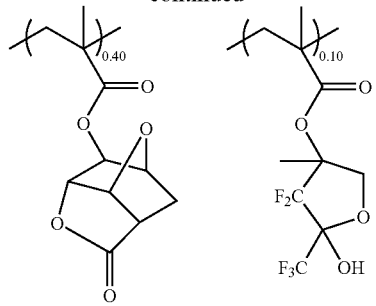

With stirring at 80° C. in a nitrogen atmosphere, a solution was added dropwise over 4 hours to 11.67 g of propylene glycol monomethyl ether acetate (PGMEA). The solution contained 5.50 g of 3-ethyl-3-exo-tetracyclo-[4.4.0.1$^{2,5}$.1$^{7,10}$]dodecanyl methacrylate, 4.69 g of 3-hydroxy-1-adamantyl methacrylate, 7.12 g of 4,8-dioxatricyclo-[4.2.1.0$^{3,7}$]nonan-5-on-2-yl methacrylate, 2.33 g of 4,4-difluoro-5-hydroxy-3-methyl-5-trifluoromethylfuran-3-yl methacrylate, 521 mg of 2,2'-azobisisobutyronitrile, and 93.0 mg of 2-mercaptoethanol in 35.0 g of PGMEA. The mixture was stirred at 80° C. for a further 2 hours. The reaction mixture was cooled to room temperature and with vigorous stirring, added dropwise to 1,000 ml of n-hexane. The resulting solids were collected by filtration and vacuum dried at 50° C. for 15 hours, leaving 17.3 g of a polymer in white powder solid form (yield 88%).

The polymer had a copolymerization ratio of approximately 25.3/23.2/42.2/9.3 as computed from an integration ratio of $^1$H-NMR spectrum and a weight average molecular weight (Mw) of 8,500 as measured by GPC versus polystyrene standards.

Resolution as Resist Material

A resist solution was prepared by mixing 80 parts by weight of the polymer of Example 12, 2.18 parts by weight of triphenylsulfonium nonafluorobutanesulfonate as a photo-acid generator, 0.472 part by weight of trismethoxymethoxyethylamine as a basic compound, and 640 parts by weight of PGMEA (containing 0.01 wt % of surfactant KH-20 by Asahi Glass Co., Ltd.) as a solvent and passing through a Teflone filter with a pore diameter of 0.2 μm.

The resist solution was spin-coated on a silicon wafer having an antireflective coating (ARC29A by Nissan Chemical Industries Ltd., 78 nm) coated thereon, and heat treated at 130° C. for 60 seconds to form a resist film of 300 nm thick. The resist film was exposed on an ArF excimer laser stepper (Nikon Corp., NA=0.68), heat treated at 105° C. for 60 seconds, and puddle-developed in a 2.38 wt % tetramethylammonium hydroxide aqueous solution for 60 seconds, forming a 1:1 line-and-space pattern. The developed wafer was cut, and the cross section was observed under a scanning electron microscope (SEM). The optimum dose (Eop, mJ/cm$^2$) is defined as the dose which provides a 1:1 resolution at the top and bottom of a 0.13 μm line-and-space pattern, and the resolution is defined as the minimum line width (μm) of the lines and spaces that separate at this dose. The resist showed an optimum dose of 25 mJ/cm$^2$, a minimum line width of 0.11 μm, and good pattern rectangularity. It was demonstrated that the resist material within the scope of the invention has a high resolution upon ArF excimer laser exposure.

Example 13

Synthesis of 3,3-difluoro-2-hydroxy-2-trifluoromethyl-2,3,3a,4,5,6,7,7a-octahydrobenzofuran-3a-yl methacrylate

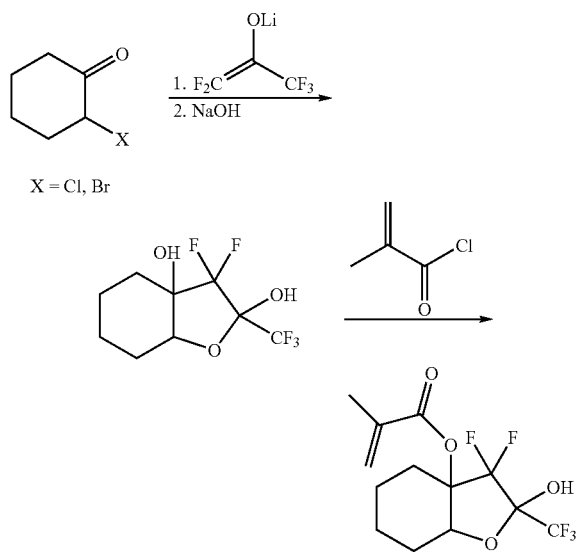

[13-1] One synthesis of 3,3-difluoro-2-trifluoromethyl-2,3,3a,4,5,6,7,7a-octahydrobenzofuran-2,3a-diol In a nitrogen atmosphere at −5° C., 1000 ml of 2.6M n-butyllithium in hexane was added to a mixture of 224 g of 1,1,1,3,3,3-hexafluoro-2-propanol and 1000 g of tetrahydrofuran, followed by one hour of stirring at 5° C. Then 164 g of 2-chlorocyclohexanone was added at 5° C. The mixture was stirred for 10 hours, after which dilute hydrochloric acid was added to quench the reaction and neutralize the reaction mixture. Then 1200 g of a 10% aqueous solution of sodium hydroxide was added to the reaction mixture, from which an aqueous layer was separated. It was made acidic by adding 560 g of 20% dilute hydrochloric acid and combined with 1000 g of toluene, after which an organic layer was separated. The organic layer thus separated was concentrated and purified by recrystallization from hexane, obtaining 201 g of the product (yield 63%).

[13-2] Another synthesis of 3,3-difluoro-2-trifluoromethyl-2,3,3a,4,5,6,7,7a-octahydrobenzofuran-2,3a-diol In a nitrogen atmosphere at −5° C., 260 ml of 2.6M n-butyllithium in hexane was added to a mixture of 58 g of 1,1,1,3,3,3-hexafluoro-2-propanol and 260 g of tetrahydrofuran, followed by one hour of stirring at 5° C. Then 59 g of 2-bromocyclohexanone was added at 5° C. The mixture was stirred for 10 hours, after which dilute hydrochloric acid was added to quench the reaction and neutralize the reaction mixture. Then 310 g of a 10% aqueous solution of sodium hydroxide was added to the reaction mixture, from which an aqueous layer was separated. It was made acidic by adding 150 g of 20% dilute hydrochloric acid and combined with 250 g of toluene, after which separatory operation was performed to separate an organic layer. The organic layer was concentrated and purified by recrystallization from hexane, obtaining 58 g of the product (yield 72%).

3,3-difluoro-2-trifluoromethyl-2,3,3a,4,5,6,7,7a-octahydrobenzofuran-2,3a-diol (mixture of 67:33 diastereomers as calculated in DMSO-d6)

Colorless solid
GC-MS (EI): (m/z)$^+$=27, 41, 55, 70, 97, 113, 130, 148, 175, 189, 205, 229, 244, 262 [M$^+$]
IR (KBr): ν=3450, 2947, 1384, 1324, 1274, 1255, 1207, 1191, 1178, 1106, 1066, 973, 916, 875, 836, 736, 705 cm$^{-1}$
$^1$H-NMR of main diasteredmer (600 MHz in DMSO-d6): δ=1.25-1.83 (8H, m), 3.88 (1H, s), 5.76 (1H, s), 8.56 (1H, s) ppm
$^{19}$F-NMR of main diastereomer (565 MHz in DMSO-d6, trifluoroacetic acid standard): δ=−129.4 (1F, d, J=235.1 Hz), −129.4 (1F, dq, J=235.1, 18.4 Hz), −81.2 (3F, d, J=18.4 Hz) ppm

[13-3] Synthesis of 3,3-difluoro-2-hydroxy-2-trifluoromethyl-2,3,3a,4,5,6,7,7a-octahydrobenzofuran-3a-yl 2-methacrylate To a mixture of 17 g of 3,3-difluoro-2-trifluoro-methyl-2,3,3a,4,5,6,7,7a-octahydrobenzofuran-2,3a-diol, 9 g of triethylamine, 0.8 g of N,N-dimethylaminopyridine, 16 mg of 2,2'-methylenebis(6-t-butyl-p-cresole) and 160 g of acetonitrile at 5° C. was added 7 g of methacryloyl chloride. The reaction solution was heated at 50° C. for 4 days, after which 150 g of water was added to quench the reaction. The reaction solution was combined with 150 g of toluene, after which an organic layer was separated. Then 80 g of 5% dilute hydrochloric acid was added to help remove the triethylamine. The reaction solution was subjected to conventional aqueous work-up and concentrated. The concentrate was purified by recrystallization from methylene chloride and hexane, obtaining 13 g of the end compound (yield 66%).

3,3-difluoro-2-hydroxy-2-trifluoromethyl-2,3,3a,4,5, 6,7,7a-octahydrobenzofuran-3a-yl methacrylate (mixture of ca. 50:50 diastereomers)

Colorless solid
GC-MS (EI): (m/z)$^+$=41, 69, 87, 147, 216, 244
GC-MS (CI, methane): (m/z)$^+$=69, 87, 245, 313, 331 [(M+H)$^+$]
IR (KBr): ν=3419, 2960, 1724, 1246, 1201, 1188, 1167, 1147, 1126, 1072, 1060, 1033, 983, 873, 740, 717, 538 cm$^{-1}$
$^1$H-NMR (600 MHz in DMSO-d6): δ=1.17-1.85 (6H, m), 1.88-1.89 (3H, m), 1.90-1.97 (1H, m), 2.35-2.42 (1H, m), 4.11 (0.5H, s), 4.29 (0.5H, s), 5.79 (1H, m), 6.13 (1H, m), 8.76 (0.5H, s), 8.97 (0.5H, s) ppm
$^{13}$C-NMR (150 MHz in DMSO-d6): δ=16.15, 18.14 (d, J=10 Hz), 19.27, 19.37, 60.91, 66.39 (d, J=13 Hz), 78.11 (t, J=23 Hz), 78.94 (t, J=24 Hz), 82.25, 82.63, 93.0-93.5 (m×2), 113.61 (dd, J=266, 256 Hz), 114.12 (dd, J=269, 256 Hz), 122.53 (q×2, J=287 Hz), 128.05, 128.10, 136.79, 136.87, 167.28, 167.62 ppm
$^{19}$F-NMR (565 MHz in DMSO-d6, trifluoroacetic acid standard): δ=−124.0 (0.5F, dq, J=239.7, 18.4 Hz), −121.9 (0.5F, dq, J=243.5, 16.3 Hz), −116.7 (0.5F, d, J=240.5 Hz), −111.4 (0.5F, d, J=243.8 Hz), −81.0 (3×0.5F, d, J=19.5 Hz), −80.8 (3×0.5F, d, J=16.2 Hz) ppm Example 14 and Comparative Example 1

[Preparation of Resins]

Resins as listed in Table 1 were prepared by the same procedure as in Example 12 aside from changing the type and ratio of monomers used. The type and ratio of units incorporated in each polymer and the weight average molecular weight (Mw) thereof are shown in Table 1 while the structure of units is shown in Tables 2 to 4.

TABLE 1

|  | Resin | Unit 1 (ratio) | Unit 2 (ratio) | Unit 3 (ratio) | Unit 4 (ratio) | Unit 5 (ratio) | Mw |
|---|---|---|---|---|---|---|---|
| Example 14-1 | P-01 | F-1M (0.10) | A-1M (0.25) | B-1M (0.25) | B-2M (0.40) | — | 6,800 |
| Example 14-2 | P-02 | F-2M (0.10) | A-1M (0.25) | B-1M (0.25) | B-2M (0.40) | — | 6,500 |
| Example 14-3 | P-03 | F-3M (0.10) | A-1M (0.25) | B-1M (0.25) | B-2M (0.40) | — | 6,700 |
| Example 14-4 | P-04 | F-4M (0.10) | A-1M (0.25) | B-1M (0.25) | B-2M (0.40) | — | 7,000 |
| Example 14-5 | P-05 | F-5M (0.10) | A-1M (0.25) | B-1M (0.25) | B-2M (0.40) | — | 6,900 |
| Example 14-6 | P-06 | F-6M (0.10) | A-1M (0.25) | B-1M (0.25) | B-2M (0.40) | — | 6,800 |
| Example 14-7 | P-07 | F-1M (0.05) | A-1M (0.25) | B-1M (0.25) | B-2M (0.45) | — | 7,000 |
| Example 14-8 | P-08 | F-1M (0.15) | A-1M (0.25) | B-1M (0.25) | B-2M (0.35) | — | 6,800 |
| Example 14-9 | P-09 | F-1M (0.20) | A-1M (0.25) | B-1M (0.25) | B-2M (0.30) | — | 6,700 |
| Example 14-10 | P-10 | F-1M (0.10) | A-1M (0.20) | B-1M (0.25) | B-2M (0.45) | — | 7,000 |
| Example 14-11 | P-11 | F-1M (0.10) | A-1M (0.30) | B-1M (0.25) | B-2M (0.35) | — | 6,500 |
| Example 14-12 | P-12 | F-1M (0.10) | A-2M (0.25) | B-1M (0.25) | B-2M (0.40) | — | 7,200 |
| Example 14-13 | P-13 | F-1M (0.10) | A-3M (0.25) | B-1M (0.25) | B-2M (0.40) | — | 6,600 |
| Example 14-14 | P-14 | F-1M (0.10) | A-4M (0.25) | B-1M (0.25) | B-2M (0.40) | — | 6,700 |
| Example 14-15 | P-15 | F-1M (0.10) | A-5M (0.25) | B-1M (0.25) | B-2M (0.40) | — | 6,500 |
| Example 14-16 | P-16 | F-1M (0.10) | A-6M (0.25) | B-1M (0.25) | B-2M (0.40) | — | 6,700 |
| Example 14-17 | P-17 | F-1M (0.10) | A-1M (0.25) | B-1M (0.25) | B-3M (0.40) | — | 6,700 |
| Example 14-18 | P-18 | F-1M (0.10) | A-1M (0.25) | B-1M (0.25) | B-4M (0.40) | — | 6,800 |
| Example 14-19 | P-19 | F-1M (0.10) | A-1M (0.25) | B-1M (0.25) | B-5M (0.40) | — | 6,500 |
| Example 14-20 | P-20 | F-1M (0.05) | A-1M (0.25) | B-1M (0.25) | B-2M (0.40) | B-6M (0.05) | 6,700 |
| Example 14-21 | P-21 | F-1M (0.05) | A-1M (0.25) | B-1M (0.25) | B-2M (0.35) | B-6M (0.10) | 6,600 |
| Example 14-22 | P-22 | F-1M (0.10) | A-1M (0.25) | B-1M (0.25) | B-2M (0.35) | B-6M (0.05) | 6,700 |
| Example 14-23 | P-23 | F-1M (0.10) | A-1M (0.25) | B-1M (0.25) | B-2M (0.30) | B-6M (0.10) | 6,500 |
| Example 14-24 | P-24 | F-1M (0.10) | A-1A (0.25) | B-1M (0.25) | B-2M (0.40) | — | 6,900 |
| Example 14-25 | P-25 | F-1M (0.10) | A-1M (0.25) | B-1A (0.25) | B-2M (0.40) | — | 6,800 |
| Example 14-26 | P-26 | F-1M (0.10) | A-1M (0.25) | B-1M (0.25) | B-2A (0.40) | — | 6,800 |
| Example 14-27 | P-27 | F-1M (0.10) | A-1M (0.25) | B-1A (0.25) | B-2A (0.40) | — | 6,900 |
| Example 14-28 | P-28 | F-1M (0.10) | A-1A (0.25) | B-1A (0.25) | B-2M (0.40) | — | 6,800 |
| Comparative Example 1-1 | P-29 | — | A-1M (0.30) | B-1M (0.25) | B-2M (0.45) | — | 7,200 |
| Comparative Example 1-2 | P-30 | — | A-1M (0.25) | B-1M (0.25) | B-2M (0.40) | B-6M (0.10) | 6,500 |

TABLE 2

| F-1M (R = CH₃) | F-2M (R = CH₃) | F-3M (R = CH₃) |
| F-1A (R = H)   | F-2A (R = H)   | F-3A (R = H)   |

| F-4M (R = CH₃) | F-5M (R = CH₃) | F-6M (R = CH₃) |
| F-4A (R = H)   | F-5A (R = H)   | F-6A (R = H)   |

TABLE 3

| A-1M (R = CH₃) | A-2M (R = CH₃) | A-3M (R = CH₃) | A-4M (R = CH₃) | A-5M (R = CH₃) | A-6M (R = CH₃) |
| A-1A (R = H)   | A-2A (R = H)   | A-3A (R = H)   | A-4A (R = H)   | A-5A (R = H)   | A-6A (R = H)   |

TABLE 4

| B-1M (R = CH₃) | B-2M (R = CH₃) | B-3M (R = CH₃) | B-4M (R = CH₃) | B-5M (R = CH₃) | B-6M (R = CH₃) |
|---|---|---|---|---|---|
| B-1A (R = H) | B-2A (R = H) | B-3A (R = H) | B-4A (R = H) | B-5A (R = H) | B-6A (R = H) |

Example 15 and Comparative Example 2

[Preparation of Resist Compositions]

Resist compositions were prepared by using one of the inventive resins (P-01 to 28) and comparative resins (P-29, 30), all prepared above, as a base resin, a photoacid generator, a basic compound and a solvent in the amounts shown in Tables 5 and 6, mixing and dissolving them, and passing through a Teflon® filter with a pore diameter of 0.2 μm. Note that the solvent contained 0.01 wt % of surfactant KH-20 (Asahi Glass Co., Ltd.).

TABLE 5

| | Resist | Resin (pbw) | Photoacid generator (pbw) | Base (pbw) | Solvent 1 (pbw) | Solvent 2 (pbw) |
|---|---|---|---|---|---|---|
| Example 15-1 | R-01 | P-01 (80) | PAG-1 (4.4) | Base-1 (0.94) | PGMEA (560) | CyHO (240) |
| Example 15-2 | R-02 | P-02 (80) | PAG-1 (4.4) | Base-1 (0.94) | PGMEA (560) | CyHO (240) |
| Example 15-3 | R-03 | P-03 (80) | PAG-1 (4.4) | Base-1 (0.94) | PGMEA (560) | CyHO (240) |
| Example 15-4 | R-04 | P-04 (80) | PAG-1 (4.4) | Base-1 (0.94) | PGMEA (560) | CyHO (240) |
| Example 15-5 | R-05 | P-05 (80) | PAG-1 (4.4) | Base-1 (0.94) | PGMEA (560) | CyHO (240) |
| Example 15-6 | R-06 | P-06 (80) | PAG-1 (4.4) | Base-1 (0.94) | PGMEA (560) | CyHO (240) |
| Example 15-7 | R-07 | P-01 (80) | PAG-2 (4.9) | Base-1 (0.94) | PGMEA (560) | CyHO (240) |
| Example 15-8 | R-08 | P-01 (80) | PAG-3 (4.8) | Base-1 (0.94) | PGMEA (560) | CyHO (240) |
| Example 15-9 | R-09 | P-01 (80) | PAG-4 (5.6) | Base-1 (0.94) | PGMEA (560) | CyHO (240) |
| Example 15-10 | R-10 | P-01 (80) | PAG-5 (4.5) | Base-1 (0.94) | PGMEA (560) | CyHO (240) |
| Example 15-11 | R-11 | P-01 (80) | PAG-6 (4.6) | Base-1 (0.94) | PGMEA (560) | CyHO (240) |
| Example 15-12 | R-12 | P-01 (80) | PAG-1 (3.3) PAG-7 (3.8) | Base-1 (0.94) | PGMEA (560) | CyHO (240) |
| Example 15-13 | R-13 | P-01 (80) | PAG-1 (4.4) | Base-2 (0.74) | PGMEA (560) | CyHO (240) |
| Example 15-14 | R-14 | P-01 (80) | PAG-1 (4.4) | Base-3 (0.64) | PGMEA (560) | CyHO (240) |
| Example 15-15 | R-15 | P-07 (80) | PAG-1 (4.4) | Base-2 (0.74) | PGMEA (560) | CyHO (240) |
| Example 15-16 | R-16 | P-08 (80) | PAG-1 (4.4) | Base-2 (0.74) | PGMEA (560) | CyHO (240) |
| Example 15-17 | R-17 | P-09 (80) | PAG-1 (4.4) | Base-2 (0.74) | PGMEA (560) | CyHO (240) |
| Example 15-18 | R-18 | P-10 (80) | PAG-1 (4.4) | Base-2 (0.74) | PGMEA (560) | CyHO (240) |
| Example 15-19 | R-19 | P-11 (80) | PAG-1 (4.4) | Base-2 (0.74) | PGMEA (560) | CyHO (240) |
| Example 15-20 | R-20 | P-12 (80) | PAG-1 (4.4) | Base-2 (0.74) | PGMEA (560) | CyHO (240) |
| Example 15-21 | R-21 | P-13 (80) | PAG-1 (4.4) | Base-2 (0.74) | PGMEA (560) | CyHO (240) |
| Example 15-22 | R-22 | P-14 (80) | PAG-1 (4.4) | Base-2 (0.74) | PGMEA (560) | CyHO (240) |
| Example 15-23 | R-23 | P-15 (80) | PAG-1 (4.4) | Base-2 (0.74) | PGMEA (560) | CyHO (240) |
| Example 15-24 | R-24 | P-16 (80) | PAG-1 (4.4) | Base-2 (0.74) | PGMEA (560) | CyHO (240) |
| Example 15-25 | R-25 | P-17 (80) | PAG-1 (4.4) | Base-2 (0.74) | PGMEA (560) | CyHO (240) |
| Example 15-26 | R-26 | P-18 (80) | PAG-1 (4.4) | Base-2 (0.74) | PGMEA (560) | CyHO (240) |
| Example 15-27 | R-27 | P-19 (80) | PAG-1 (4.4) | Base-2 (0.74) | PGMEA (560) | CyHO (240) |
| Example 15-28 | R-28 | P-20 (80) | PAG-1 (4.4) | Base-2 (0.74) | PGMEA (560) | CyHO (240) |
| Example 15-29 | R-29 | P-21 (80) | PAG-1 (4.4) | Base-2 (0.74) | PGMEA (560) | CyHO (240) |
| Example 15-30 | R-30 | P-22 (80) | PAG-1 (4.4) | Base-2 (0.74) | PGMEA (560) | CyHO (240) |
| Example 15-31 | R-31 | P-23 (80) | PAG-1 (4.4) | Base-2 (0.74) | PGMEA (560) | CyHO (240) |
| Example 15-32 | R-32 | P-24 (80) | PAG-1 (4.4) | Base-3 (0.64) | PGMEA (560) | CyHO (240) |
| Example 15-33 | R-33 | P-25 (80) | PAG-1 (4.4) | Base-3 (0.64) | PGMEA (560) | CyHO (240) |
| Example 15-34 | R-34 | P-26 (80) | PAG-1 (4.4) | Base-3 (0.64) | PGMEA (560) | CyHO (240) |
| Example 15-35 | R-35 | P-27 (80) | PAG-1 (4.4) | Base-3 (0.64) | PGMEA (560) | CyHO (240) |
| Example 15-36 | R-36 | P-28 (80) | PAG-1 (4.4) | Base-3 (0.64) | PGMEA (560) | CyHO (240) |

TABLE 6

| | Resist | Resin (pbw) | Photoacid generator (pbw) | Base (pbw) | Solvent 1 (pbw) | Solvent 2 (pbw) |
|---|---|---|---|---|---|---|
| Example 15-37 | R-37 | P-01 (80) | PAG-1 (4.4) | Base-4 (0.98) | PGMEA (560) | CyHO (240) |
| Example 15-38 | R-38 | P-12 (80) | PAG-1 (4.4) | Base-4 (0.98) | PGMEA (560) | CyHO (240) |
| Example 15-39 | R-39 | P-13 (80) | PAG-1 (4.4) | Base-4 (0.98) | PGMEA (560) | CyHO (240) |
| Example 15-40 | R-40 | P-14 (80) | PAG-1 (4.4) | Base-4 (0.98) | PGMEA (560) | CyHO (240) |
| Example 15-41 | R-41 | P-15 (80) | PAG-1 (4.4) | Base-4 (0.98) | PGMEA (560) | CyHO (240) |
| Example 15-42 | R-42 | P-16 (80) | PAG-1 (4.4) | Base-4 (0.98) | PGMEA (560) | CyHO (240) |
| Example 15-43 | R-43 | P-01 (80) | PAG-1 (4.4) | Base-5 (0.86) | PGMEA (560) | CyHO (240) |
| Example 15-44 | R-44 | P-12 (80) | PAG-1 (4.4) | Base-5 (0.86) | PGMEA (560) | CyHO (240) |
| Example 15-45 | R-45 | P-13 (80) | PAG-1 (4.4) | Base-5 (0.86) | PGMEA (560) | CyHO (240) |
| Example 15-46 | R-46 | P-14 (80) | PAG-1 (4.4) | Base-5 (0.86) | PGMEA (560) | CyHO (240) |
| Example 15-47 | R-47 | P-15 (80) | PAG-1 (4.4) | Base-5 (0.86) | PGMEA (560) | CyHO (240) |
| Example 15-48 | R-48 | P-16 (80) | PAG-1 (4.4) | Base-5 (0.86) | PGMEA (560) | CyHO (240) |
| Example 15-49 | R-49 | P-01 (80) | PAG-1 (4.4) | Base-6 (1.05) | PGMEA (560) | CyHO (240) |
| Example 15-50 | R-50 | P-12 (80) | PAG-1 (4.4) | Base-6 (1.05) | PGMEA (560) | CyHO (240) |
| Example 15-51 | R-51 | P-13 (80) | PAG-1 (4.4) | Base-6 (1.05) | PGMEA (560) | CyHO (240) |
| Example 15-52 | R-52 | P-14 (80) | PAG-1 (4.4) | Base-6 (1.05) | PGMEA (560) | CyHO (240) |
| Example 15-53 | R-53 | P-15 (80) | PAG-1 (4.4) | Base-6 (1.05) | PGMEA (560) | CyHO (240) |
| Example 15-54 | R-54 | P-16 (80) | PAG-1 (4.4) | Base-6 (1.05) | PGMEA (560) | CyHO (240) |
| Example 15-55 | R-55 | P-01 (80) | PAG-1 (4.4) | Base-7 (1.24) | PGMEA (560) | CyHO (240) |
| Example 15-56 | R-56 | P-12 (80) | PAG-1 (4.4) | Base-7 (1.24) | PGMEA (560) | CyHO (240) |
| Example 15-57 | R-57 | P-13 (80) | PAG-1 (4.4) | Base-7 (1.24) | PGMEA (560) | CyHO (240) |
| Example 15-58 | R-58 | P-14 (80) | PAG-1 (4.4) | Base-7 (1.24) | PGMEA (560) | CyHO (240) |
| Example 15-59 | R-59 | P-15 (80) | PAG-1 (4.4) | Base-7 (1.24) | PGMEA (560) | CyHO (240) |
| Example 15-60 | R-60 | P-16 (80) | PAG-1 (4.4) | Base-7 (1.24) | PGMEA (560) | CyHO (240) |
| Example 15-61 | R-61 | P-01 (80) | PAG-1 (4.4) | Base-8 (1.33) | PGMEA (560) | CyHO (240) |
| Example 15-62 | R-62 | P-12 (80) | PAG-1 (4.4) | Base-8 (1.33) | PGMEA (560) | CyHO (240) |
| Example 15-63 | R-63 | P-13 (80) | PAG-1 (4.4) | Base-8 (1.33) | PGMEA (560) | CyHO (240) |
| Example 15-64 | R-64 | P-14 (80) | PAG-1 (4.4) | Base-8 (1.33) | PGMEA (560) | CyHO (240) |
| Example 15-65 | R-65 | P-15 (80) | PAG-1 (4.4) | Base-8 (1.33) | PGMEA (560) | CyHO (240) |
| Example 15-66 | R-66 | P-16 (80) | PAG-1 (4.4) | Base-8 (1.33) | PGMEA (560) | CyHO (240) |
| Comparative Example 2-1 | R-67 | P-29 (80) | PAG-1 (4.4) | Base-2 (0.74) | PGMEA (560) | CyHO (240) |
| Comparative Example 2-2 | R-68 | P-30 (80) | PAG-1 (4.4) | Base-2 (0.74) | PGMEA (560) | CyHO (240) |

The abbreviations for photoacid generator, base and solvent used in Table 5 have the following meaning.

PAG-1: triphenylsulfonium nonafluorobutanesulfonate

PAG-2: 4-t-butoxyphenyldiphenylsulfonium nonafluorobutanesulfonate

PAG-3: 4-t-butylphenyldiphenylsulfonium nonafluorobutanesulfonate

PAG-4: triphenylsulfonium pentadecafluoro-4-ethylcyclohexanesulfonate

PAG-5: triphenylsulfonium 1,1,3,3,3-pentafluoro-2-t-butylcarboxypropanesulfonate PAG-6: triphenylsulfonium 1,1,3,3,3-pentafluoro-2-benzoyloxypropanesulfonate PAG-7: phenacyltetramethylenesulfonium nonafluorobutanesulfonate Base-1: tri(2-methoxymethoxyethyl)amine Base-2: 2-(2-methoxyethoxymethoxy)ethylmorpholine Base-3: N-(2-acetoxyethyl)benzimidazole Base-4: 2-morpholinoethyl 2-[2-(2-methoxyethoxy)ethoxy]acetate Base-5: 2-morpholinoethyl octanoate Base-6: 2-morpholinoethyl laurate Base-7: 2-morpholinoethyl palmitate Base-8: 2-morpholinoethyl stearate PGMEA: 1-methoxyisopropyl acetate CyHO: cyclohexanone Example 16 and Comparative Example 3

[Evaluation of Resist Compositions]

Each of the inventive resist compositions (R-01 to 66) and comparative resist compositions (R-67, 68) was spin-coated on a silicon wafer having an antireflective coating (ARC29A by Nissan Chemical Industries Ltd., 78 nm) coated thereon, and heat treated at 110° C. for 60 seconds to form a resist film of 170 nm thick. The resist film was exposed on an ArF excimer laser stepper (Nikon Corp., NA=0.68), heat treated (PEB) at a temperature for 60 seconds, and puddle-developed in a 2.38 wt % tetramethylammonium hydroxide aqueous solution for 30 seconds, forming a 1:1 line-and-space pattern. The PEB was performed at an optimum temperature for a particular resist composition used.

The developed wafer was observed under a top-down scanning electron microscope (SEM). The optimum dose (Eop, mJ/cm$^2$) is defined as the dose which provides a 1:1 resolution at the top and bottom of a 0.11 μm line-and-space (1:1) pattern. The threshold resolution is defined as the minimum size (in 0.01 μm scale unit) that is resolved separate at the optimum dose (the smaller the size, the better is the resolution). Testing of swell resistance was performed while the line pattern was gradually reduced in size with the dose of exposure kept deliberately excessive. The minimum size above which the profile was retained without collapse was determined, giving an assessment of swell resistance (the smaller the size, the better is the swell resistance).

Tables 7 and 8 show the test results (threshold resolution and swell resistance) of the resist compositions.

TABLE 7

| Resist | PEB temperature | Optimum dose | Threshold resolution | Swell resistance |
|---|---|---|---|---|
| Example 16-1 | R-01 | 110° C. | 42.0 mJ/cm² | 0.09 μm | <0.04 μm |
| Example 16-2 | R-02 | 110° C. | 43.0 mJ/cm² | 0.09 μm | <0.04 μm |
| Example 16-3 | R-03 | 110° C. | 41.0 mJ/cm² | 0.09 μm | <0.04 μm |
| Example 16-4 | R-04 | 110° C. | 42.0 mJ/cm² | 0.09 μm | <0.04 μm |
| Example 16-5 | R-05 | 110° C. | 44.0 mJ/cm² | 0.09 μm | <0.04 μm |
| Example 16-6 | R-06 | 110° C. | 40.0 mJ/cm² | 0.09 μm | <0.04 μm |
| Example 16-7 | R-07 | 110° C. | 48.0 mJ/cm² | 0.09 μm | <0.04 μm |
| Example 16-8 | R-08 | 110° C. | 46.0 mJ/cm² | 0.09 μm | <0.04 μm |
| Example 16-9 | R-09 | 110° C. | 50.0 mJ/cm² | 0.09 μm | <0.04 μm |
| Example 16-10 | R-10 | 110° C. | 43.0 mJ/cm² | 0.09 μm | <0.04 μm |
| Example 16-11 | R-11 | 110° C. | 41.0 mJ/cm² | 0.09 μm | <0.04 μm |
| Example 16-12 | R-12 | 110° C. | 39.0 mJ/cm² | 0.10 μm | <0.04 μm |
| Example 16-13 | R-13 | 110° C. | 42.0 mJ/cm² | 0.09 μm | <0.04 μm |
| Example 16-14 | R-14 | 110° C. | 44.0 mJ/cm² | 0.09 μm | <0.04 μm |
| Example 16-15 | R-15 | 110° C. | 44.0 mJ/cm² | 0.09 μm | <0.04 μm |
| Example 16-16 | R-16 | 110° C. | 42.0 mJ/cm² | 0.09 μm | <0.04 μm |
| Example 16-17 | R-17 | 110° C. | 41.0 mJ/cm² | 0.09 μm | <0.04 μm |
| Example 16-18 | R-18 | 110° C. | 45.0 mJ/cm² | 0.09 μm | <0.04 μm |
| Example 16-19 | R-19 | 110° C. | 40.0 mJ/cm² | 0.10 μm | <0.04 μm |
| Example 16-20 | R-20 | 125° C. | 40.0 mJ/cm² | 0.09 μm | <0.04 μm |
| Example 16-21 | R-21 | 115° C. | 42.0 mJ/cm² | 0.09 μm | <0.04 μm |
| Example 16-22 | R-22 | 125° C. | 40.0 mJ/cm² | 0.09 μm | <0.04 μm |
| Example 16-23 | R-23 | 115° C. | 43.0 mJ/cm² | 0.09 μm | <0.04 μm |
| Example 16-24 | R-24 | 110° C. | 44.0 mJ/cm² | 0.09 μm | <0.04 μm |
| Example 16-25 | R-25 | 110° C. | 41.0 mJ/cm² | 0.09 μm | <0.04 μm |
| Example 16-26 | R-26 | 110° C. | 42.0 mJ/cm² | 0.09 μm | <0.04 μm |
| Example 16-27 | R-27 | 110° C. | 38.0 mJ/cm² | 0.10 μm | <0.04 μm |
| Example 16-28 | R-28 | 110° C. | 42.0 mJ/cm² | 0.09 μm | <0.04 μm |
| Example 16-29 | R-29 | 110° C. | 41.0 mJ/cm² | 0.09 μm | <0.04 μm |
| Example 16-30 | R-30 | 110° C. | 41.0 mJ/cm² | 0.09 μm | <0.04 μm |
| Example 16-31 | R-31 | 110° C. | 39.0 mJ/cm² | 0.09 μm | <0.04 μm |
| Example 16-32 | R-32 | 105° C. | 40.0 mJ/cm² | 0.09 μm | <0.04 μm |
| Example 16-33 | R-33 | 105° C. | 41.0 mJ/cm² | 0.09 μm | <0.04 μm |
| Example 16-34 | R-34 | 105° C. | 40.0 mJ/cm² | 0.09 μm | <0.04 μm |
| Example 16-35 | R-35 | 105° C. | 38.0 mJ/cm² | 0.10 μm | <0.04 μm |
| Example 16-36 | R-36 | 105° C. | 38.0 mJ/cm² | 0.10 μm | <0.04 μm |

TABLE 8

| Resist | PEB temperature | Optimum dose | Threshold resolution | Swell resistance |
|---|---|---|---|---|
| Example 16-37 | R-37 | 110° C. | 43.0 mJ/cm² | 0.09 μm | <0.04 μm |
| Example 16-38 | R-38 | 125° C. | 40.0 mJ/cm² | 0.09 μm | <0.04 μm |
| Example 16-39 | R-39 | 115° C. | 43.0 mJ/cm² | 0.09 μm | <0.04 μm |
| Example 16-40 | R-40 | 125° C. | 40.0 mJ/cm² | 0.09 μm | <0.04 μm |
| Example 16-41 | R-41 | 115° C. | 43.0 mJ/cm² | 0.09 μm | <0.04 μm |
| Example 16-42 | R-42 | 110° C. | 44.0 mJ/cm² | 0.09 μm | <0.04 μm |
| Example 16-43 | R-43 | 110° C. | 41.0 mJ/cm² | 0.09 μm | <0.04 μm |
| Example 16-44 | R-44 | 125° C. | 40.0 mJ/cm² | 0.09 μm | <0.04 μm |
| Example 16-45 | R-45 | 115° C. | 42.0 mJ/cm² | 0.09 μm | <0.04 μm |
| Example 16-46 | R-46 | 125° C. | 40.0 mJ/cm² | 0.09 μm | <0.04 μm |
| Example 16-47 | R-47 | 115° C. | 42.0 mJ/cm² | 0.09 μm | <0.04 μm |
| Example 16-48 | R-48 | 110° C. | 43.0 mJ/cm² | 0.09 μm | <0.04 μm |
| Example 16-49 | R-49 | 110° C. | 42.0 mJ/cm² | 0.09 μm | <0.04 μm |
| Example 16-50 | R-50 | 125° C. | 40.0 mJ/cm² | 0.09 μm | <0.04 μm |
| Example 16-51 | R-51 | 115° C. | 41.0 mJ/cm² | 0.09 μm | <0.04 μm |
| Example 16-52 | R-52 | 125° C. | 40.0 mJ/cm² | 0.09 μm | <0.04 μm |
| Example 16-53 | R-53 | 115° C. | 43.0 mJ/cm² | 0.09 μm | <0.04 μm |
| Example 16-54 | R-54 | 110° C. | 43.0 mJ/cm² | 0.09 μm | <0.04 μm |
| Example 16-55 | R-55 | 110° C. | 43.0 mJ/cm² | 0.09 μm | <0.04 μm |
| Example 16-56 | R-56 | 125° C. | 41.0 mJ/cm² | 0.09 μm | <0.04 μm |
| Example 16-57 | R-57 | 115° C. | 43.0 mJ/cm² | 0.09 μm | <0.04 μm |
| Example 16-58 | R-58 | 125° C. | 42.0 mJ/cm² | 0.09 μm | <0.04 μm |
| Example 16-59 | R-59 | 115° C. | 44.0 mJ/cm² | 0.09 μm | <0.04 μm |
| Example 16-60 | R-60 | 110° C. | 44.0 mJ/cm² | 0.09 μm | <0.04 μm |
| Example 16-61 | R-61 | 110° C. | 43.0 mJ/cm² | 0.09 μm | <0.04 μm |
| Example 16-62 | R-62 | 125° C. | 42.0 mJ/cm² | 0.09 μm | <0.04 μm |
| Example 16-63 | R-63 | 115° C. | 43.0 mJ/cm² | 0.09 μm | <0.04 μm |
| Example 16-64 | R-64 | 125° C. | 42.0 mJ/cm² | 0.09 μm | <0.04 μm |
| Example 16-65 | R-65 | 115° C. | 43.0 mJ/cm² | 0.09 μm | <0.04 μm |

TABLE 8-continued

| Resist | PEB temperature | Optimum dose | Threshold resolution | Swell resistance |
|---|---|---|---|---|
| Example 16-66 | R-66 | 110° C. | 44.0 mJ/cm² | 0.09 μm | <0.04 μm |
| Comparative Example 3-1 | R-67 | 110° C. | 40.0 mJ/cm² | 0.10 μm | 0.05 μm |
| Comparative Example 3-2 | R-68 | 110° C. | 43.0 mJ/cm² | 0.09 μm | 0.05 μm |

It is seen from the data of Table 6 that the resist compositions within the scope of the invention are improved in resolution performance and dissolution.

Japanese Patent Application No. 2004-313762 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A fluorinated monomer having a cyclic structure represented by the general formula (1):

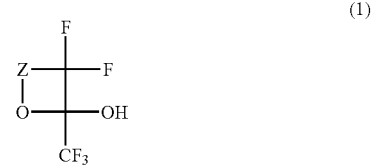

(1)

wherein Z is a divalent organic group containing a polymerizable unsaturated group, and the ring represented by

is a 5 or 6-membered ring.

2. A fluorinated monomer having a cyclic structure represented by the general formula (2), (3) or (4):

(2)

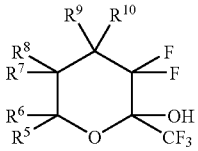

(3)

-continued

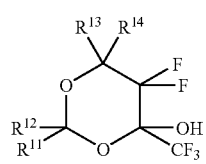
(4)

wherein $R^1$, $R^2$, $R^3$, and $R^4$ are each independently selected from among hydrogen, hydroxyl, halogen, and straight, branched or cyclic monovalent organic groups of 1 to 15 carbon atoms, at least one of $R^1$, $R^2$, $R^3$ and $R^4$ is a monovalent organic group containing a polymerizable unsaturated group, a combination of any, at least two of $R^1$, $R^2$, $R^3$ and $R^4$ may bond together to form a ring with the carbon atom or atoms to which they are attached, the ring contains a polymerizable unsaturated group unless the remaining group or groups which do not relate to the ring formation contain a polymerizable unsaturated group, $R^5$, $R^6$, $R^7$, $R^8$, $R^9$, and $R^{10}$ are each independently selected from among hydrogen, hydroxyl, halogen, and straight, branched or cyclic monovalent organic group of 1 to 15 carbon atoms, at least one of $R^5$, $R^6$, $R^7$, $R^8$, $R^9$, and $R^{10}$ is a monovalent organic group containing a polymerizable unsaturated group, a combination of any, at least two of $R^5$, $R^6$, $R^7$, $R^8$, $R^9$, and $R^{10}$ may bond together to form a ring with the carbon atom or atoms to which they are attached, the ring contains a polymerizable unsaturated group unless the remaining group or groups which do not relate to the ring formation contain a polymerizable unsaturated group, $R^{11}$, $R^{12}$, $R^{13}$, and $R^{14}$ are each independently selected from among hydrogen, hydroxyl, halogen, and straight, branched or cyclic monovalent organic groups of 1 to 15 carbon atoms, at least one of $R^{11}$, $R^{12}$, $R^{13}$ and $R^{14}$ is a monovalent organic group containing a polymerizable unsaturated group, a combination of any, at least two of $R^{11}$, $R^{12}$, $R^{13}$ and $R^{14}$ may bond together to form a ring with the carbon atom or atoms to which they are attached, the ring contains a polymerizable unsaturated group unless the remaining group or groups which do not relate to the ring formation contain a polymerizable unsaturated group.

3. The fluorinated monomer of claim 1 wherein the polymerizable unsaturated group is a group of acrylate, methacrylate or a-trifluoromethylacrylate structure having the general formula (5):

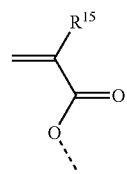
(5)

wherein $R^{15}$ is hydrogen, methyl or trifluoromethyl, and the broken line denotes a valence bond.

4. A fluorinated monomer having a cyclic structure represented by the general formula (1):

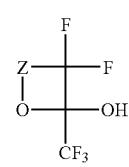
(1)

wherein Z is a divalent organic group containing a polymerizable unsaturated group, and the ring represented by

is a 5 or 6-membered ring, said polymerizable unsaturated group being a group of unsaturated hydrocarbon structure having the general formula (6) or (7):

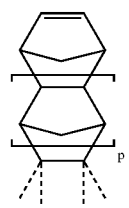
(6)

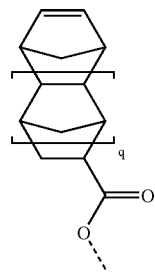
(7)

wherein p and q are each independently 1 or 0, and the broken line denotes a valence bond.

5. A polymer comprising recurring units having the general formula (1a), (2a), (3a) or (4a):

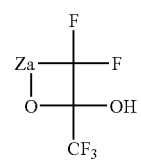
(1a)

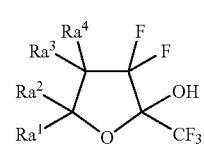
(2a)

-continued

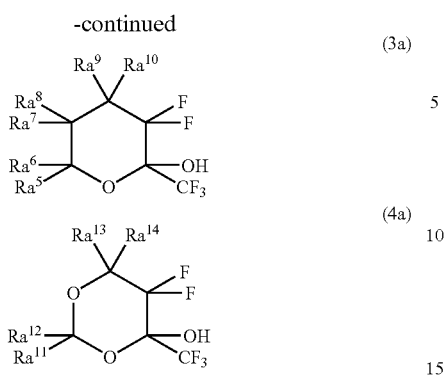

wherein Za is an organic group which is derived from a divalent organic group containing a polymerizable unsaturated group and the ring represented by

is a 5 or 6-membered ring, and which contains a polymeric main chain of recurring units in a polymer obtained through polymerization of said polymerizable unsaturated group, $Ra^1$, $Ra^2$, $Ra^3$, and $Ra^4$ are each independently selected from among hydrogen, hydroxyl, halogen, and straight, branched or cyclic monovalent organic groups of 1 to 15 carbon atoms, at least one of $Ra^1$, $Ra^2$, $Ra^3$, and $Ra^4$ is an organic group which is derived from a monovalent organic group containing a polymerizable unsaturated group, represented by at least one of $R^1$ to $R^4$, wherein $R^1$, $R^2$, $R^3$, and $R^4$ are each independently selected from among hydrogen, hydroxyl, halogen, and straight, branched or cyclic monovalent organic groups of 1 to 15 carbon atoms, at least one of $R^1$, $R^2$, $R^3$ and $R^4$ is a monovalent organic group containing a polymerizable unsaturated group, a combination of any at least two of $R^1$, $R^2$, $R^3$ and $R^4$ may bond together to form a ring with the carbon atom or atoms to which they are attached, and the ring contains a polymerizable unsaturated group unless the remaining group or groups which do not relate to the ring formation contain a polymerizable unsaturated group, and which contains a polymeric main chain of recurring units in a polymer obtained through polymerization of said polymerizable unsaturated group, a combination of any, at least two of $Ra^1$ to $Ra^4$ may bond together to form a ring with the carbon atom or atoms to which they are attached, the ring contains a polymeric main chain of recurring units in a polymer derived from a polymerizable unsaturated group and obtained through polymerization of said polymerizable unsaturated group, $Ra^5$, $Ra^6$, $Ra^7$, $Ra^8$, $Ra^9$ and $Ra^{10}$ are each independently selected from among hydrogen, hydroxyl, halogen, and straight, branched or cyclic monovalent organic groups of 1 to 15 carbon atoms, at least one of $Ra^5$ to $Ra^{10}$ is an organic group which is derived from a monovalent organic group containing a polymerizable unsaturated group, represented by at least one of $R^5$ to $R^{10}$, wherein $R^5$, $R^6$, $R^7$, $R^8$, $R^9$, and $R^{10}$ are each independently selected from among hydrogen, hydroxyl, halogen, and straight, branched or cyclic monovalent organic group of 1 to 15 carbon atoms, at least one of $R^5$, $R^6$, $R^7$, $R^8$, $R^9$, and $R^{10}$ is a monovalent organic group containing a polymerizable unsaturated group, a combination of any at least two of $R^5$, $R^6$, $R^7$, $R^8$, $R^9$, and $R^{10}$ may bond together to form a ring with the carbon atom or atoms to which they are attached, and the ring contains a polymerizable unsaturated group unless the remaining group or groups which do not relate to the ring formation contain a polymerizable unsaturated group, and which contains a polymeric main chain of recurring units in a polymer obtained through polymerization of said polymerizable unsaturated group, a combination of any, at least two of $Ra^5$ to $Ra^{10}$ may bond together to form a ring with the carbon atom or atoms to which they are attached, the ring contains a polymeric main chain of recurring units in a polymer derived from a polymerizable unsaturated group and obtained through polymerization of said polymerizable unsaturated group, $Ra^{11}$, $Ra^{12}$, $Ra^{13}$, and $Ra^{14}$ are each independently selected from among hydrogen, hydroxyl, halogen, and straight, branched or cyclic monovalent organic groups of 1 to 15 carbon atoms, at least one of $Ra^{11}$, $Ra^{12}$, $Ra^{13}$, and $Ra^{14}$ is an organic group which is derived from a monovalent organic group containing a polymerizable unsaturated group, represented by at least one of $R^{11}$ to $R^{14}$, wherein $R^{11}$, $R^{12}$, $R^{13}$, and $R^{14}$ are each independently selected from among hydrogen, hydroxyl, halogen, and straight, branched or cyclic monovalent organic groups of 1 to 15 carbon atoms, at least one of $R^{11}$, $R^{12}$, $R^{13}$ and $R^{14}$ is a monovalent organic group containing a polymerizable unsaturated group, a combination of any at least two of $R^{11}$, $R^{12}$, $R^{13}$ and $R^{14}$ may bond together to form a ring with the carbon atom or atoms to which they are attached, and the ring contains a polymerizable unsaturated group unless the remaining group or groups which do not relate to the ring formation contain a polymerizable unsaturated group, and which contains a polymeric main chain of recurring units in a polymer obtained through polymerization of said polymerizable unsaturated group, a combination of any, at least two of $Ra^{11}$ to $Ra^{14}$ may bond together to form a ring with the carbon atom or atoms to which they are attached, the ring contains a polymeric main chain of recurring units in a polymer derived from a polymerizable unsaturated group and obtained through polymerization of said polymerizable unsaturated group.

6. The polymer of claim 5, wherein the polymeric main chain of recurring units in a polymer obtained through polymerization of the polymerizable unsaturated group has an acrylate, methacrylate or c-trifluoromethylacrylate structure having the general formula (5a):

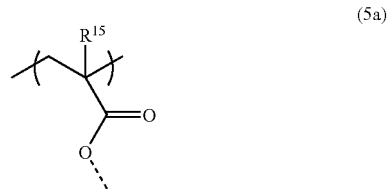

wherein $R^{15}$ is hydrogen, methyl or trifluoromethyl, and the broken line denotes a valence bond.

7. The polymer of claim 5, further comprising recurring units having the general formula (8a):

(8a)

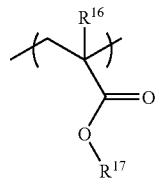

wherein $R^{16}$ is hydrogen, methyl or trifluoromethyl, and $R^{17}$ is an acid labile group, said polymer having a weight avenge molecular weight in the range of 2,000 to 100,000.

8. A photoresist composition comprising (A) the polymer of claim 5, (B) a photoacid generator, and (C) an organic solvent.

9. A process for forming a pattern, comprising the steps of (1) applying the photoresist composition of claim 8 onto a substrate to form a coating, (2) heat treating the coating and exposing it to high-energy radiation with a wavelength of up to 300 nm or electron beam through a photomask, and (3) optionally heat treating the coating and developing it with a developer.

10. A process for forming a pattern, comprising the steps of (1) applying the photoresist composition of claim 8 onto a substrate to form a coating, (2) heat treating the coated substrate, introducing a liquid between the coated substrate and a projection lens, and exposing the coating to high-energy radiation with a wavelength of up to 300 nm through a photomask, and (3) optionally heat treating the coating and developing it with a developer.

11. A method for preparing a fluorinated monomer, comprising cyclizing a keto-alcohol compound having the general formula (9), (10), (11) or (12) to form a hemiacetal compound having the general formula (13), (14), (15) or (16):

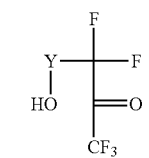
(9)

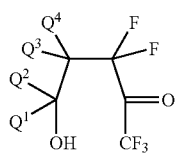
(10)

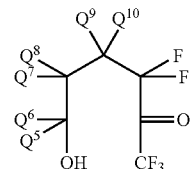
(11)

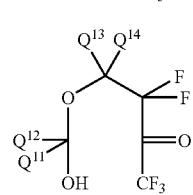
(12)

-continued

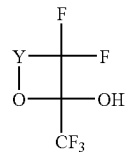
(13)

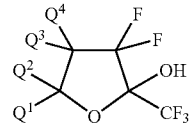
(14)

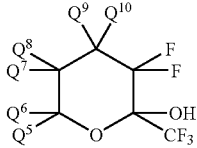
(15)

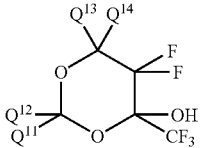
(16)

wherein Y is a divalent organic group containing a polymerizable unsaturated group or a divalent organic group having a functional group which can be converted to a polymerizable unsaturated group, the ring represented by

is a 5 or 6-membered ring, $Q^1$, $Q^2$, $Q^3$, and $Q^4$ are each independently selected from among hydrogen, hydroxyl, halogen, and straight, branched or cyclic monovalent organic groups of 1 to 15 carbon atoms, at least one of $Q^1$, $Q^2$, $Q^3$, and $Q^4$ is a monovalent organic group containing a polymerizable unsaturated group or a monovalent organic group having a functional group which can be convened to a polymerizable unsaturated group, a combination of any, at least two of $Q^1$ to $Q^4$ may bond together to form a ring with the carbon atom or atoms to which They are attached, the ring contains a polymerizable unsaturated group or a functional group which can be convened to a polymerizable unsaturated group unless The remaining group or groups which do not relate to the ring formation contain a polymerizable unsaturated group or a functional group which can be convened to a polymerizable unsaturated group, $Q^5$, $Q^6$, $Q^7$, $Q^8$, $Q^9$ and $Q^{10}$ are each independently selected from among hydrogen, hydroxyl, halogen, and straight, branched or cyclic monovalent organic groups of 1 to 15 carbon atoms, at least one of $Q^5$, $Q^6$, $Q^7$, $Q^8$, $Q^9$ and $Q^{10}$ is a monovalent organic group containing a polymerizable unsaturated group or a monovalent organic group having a functional group which can be convened to a polymerizable unsaturated group, a combination of any, at least two of $Q^5$ to $Q^{10}$ may bond together to form a ring with the carbon atom or atoms to which they are attached, the ring contains a polymerizable unsaturated group or a functional group which can be convened to a polymerizable unsaturated group unless the remaining group or groups which do not relate to The ring formation contain a polymerizable unsaturated group or a functional group which can be convened to a polymerizable unsaturated group, $Q^{11}$, $Q^{12}$, $Q^{13}$, and $Q^{14}$ are each independently selected from among hydrogen, hydroxyl, halogen, and straight, branched or cyclic monovalent organic groups of 1 to 15 carbon atoms, at least one of $Q^{11}$, $Q^{12}$, $Q^{13}$, and $Q^{14}$ is a monovalent organic group containing a polymerizable unsaturated group or a monovalent organic group having a functional group which can be convened to a polymerizable unsaturated group, a combination of any, at least two of $Q^{11}$ to $Q^{14}$ may bond together to form a ring with the carbon atom or atoms to which they are attached, the ring contains a polymerizable unsaturated group or a functional group which can be convened to a polymerizable unsaturated group unless The remaining group or groups which do not relate to the ring formation contain a polymerizable unsaturated group or a functional group which can be converted to a polymerizable unsaturated group.

12. The fluorinated monomer of claim 2 wherein the polymerizable unsaturated group is a group of acrylate, methacrylate or a-trifluoromethylacrylate structure having The general formula (5):

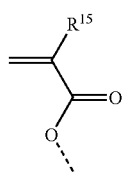
(5)

wherein $R^{15}$ is hydrogen, methyl or trifluoromethyl, and the broken line denotes a valence bond.

13. A fluorinated monomer having a cyclic structure represented by the general formula (2) (3) or (4):

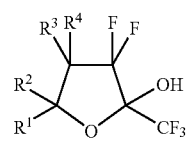
(2)

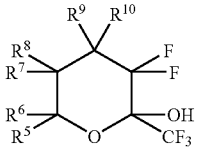
(3)

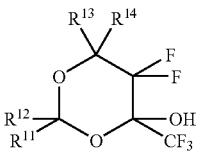
(4)

wherein $R^1$, $R^2$, $R^3$, and $R^4$ are each independently selected from among hydrogen, hydroxyl, halogen, and straight, branched or cyclic monovalent organic groups of 1 to 15 carbon atoms, at least one of $R^1$, $R^2$, $R^3$ and $R^4$ is a monovalent organic group containing a polymerizable unsaturated group, a combination of any, at least two of $R^1$, $R^2$, $R^3$ and $R^4$ may bond together to form a ring with the carbon atom or atoms to which they are attached, the ring contains a polymerizable unsaturated group unless the remaining group or groups which do not relate to the ring formation contain a polymerizable unsaturated group, $R^5$, $R^6$, $R^7$, $R^8$, $R^9$, and $R^{10}$ are each independently selected from among hydrogen, hydroxyl halogen and straight branched or cyclic monovalent organic group of 1 to 15 carbon atoms at least one of $R^5$, $R^6$, $R^7$, $R^8$, $R^9$, and $R^{10}$ is a monovalent organic group containing a polymerizable unsaturated group, a combination of any, at least two of $R^5$, $R^6$, $R^7$, $R^8$, $R^9$, and $R^{10}$ may bond together to form a ring with the carbon atom or atoms to which they are attached, the ring contains a polymerizable unsaturated group unless the remaining group or groups which do not relate to the ring formation contain a polymerizable unsaturated group, $R^{11}$, $R^{12}$, $R^{13}$, and $R^{14}$ are each independently selected from among hydrogen, hydroxyl, halogen, and straight, branched or cyclic monovalent organic groups of 1 to 15 carbon atoms, at least one of $R^{11}$, $R^{12}$, $R^{13}$ and $R^{14}$ is a monovalent organic group containing a polymerizable unsaturated group, a combination of any, at least two of $R^{11}$, $R^{12}$, $R^{13}$ and $R^{14}$ may bond together to form a ring with the carbon atom or atoms to which they are attached, the ring contains a polymerizable unsaturated group unless the remaining group or groups which do not relate to the ring formation contain a polymerizable unsaturated group, said polymerizable unsaturated group being a group of unsaturated hydrocarbon structure having the general formula (6) or (7):

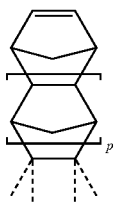
(6)

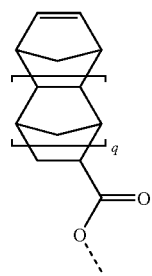
(7)

wherein p and q are each independently 1 or 0, and the broken line denotes a valence bond.

* * * * *